(12) United States Patent
Bierbach et al.

(10) Patent No.: US 9,090,640 B2
(45) Date of Patent: Jul. 28, 2015

(54) TARGETED DELIVERY AND PRODRUG DESIGNS FOR PLATINUM-ACRIDINE ANTI-CANCER COMPOUNDS AND METHODS THEREOF

(76) Inventors: Ulrich Bierbach, Winston-Salem, NC (US); Song Ding, Winston-Salem, NC (US)

( * ) Notice: Subject to any disclaimer, the term of this patent is extended or adjusted under 35 U.S.C. 154(b) by 0 days.

(21) Appl. No.: 14/241,900

(22) PCT Filed: Aug. 30, 2012

(86) PCT No.: PCT/US2012/053189
§ 371 (c)(1),
(2), (4) Date: Feb. 28, 2014

(87) PCT Pub. No.: WO2013/033430
PCT Pub. Date: Mar. 7, 2013

(65) Prior Publication Data
US 2014/0193334 A1    Jul. 10, 2014

Related U.S. Application Data

(60) Provisional application No. 61/530,746, filed on Sep. 2, 2011.

(51) Int. Cl.
*A61K 31/555* (2006.01)
*C07F 15/00* (2006.01)
*C07D 219/10* (2006.01)
*A61K 45/06* (2006.01)
*A61K 31/473* (2006.01)

(52) U.S. Cl.
CPC ........... *C07F 15/0093* (2013.01); *A61K 31/473* (2013.01); *A61K 31/555* (2013.01); *A61K 45/06* (2013.01); *C07D 219/10* (2013.01)

(58) Field of Classification Search
USPC ............................................. 514/185; 546/10
See application file for complete search history.

(56) References Cited

U.S. PATENT DOCUMENTS 8,906,896 B2 * 12/2014 Bierbach ....................... 514/185

* cited by examiner

*Primary Examiner* — Charanjit Aulakh
(74) *Attorney, Agent, or Firm* — Ben Schroeder Law PLLC

(57) ABSTRACT

Acridine containing cisplatin compounds have been disclosed that show greater efficacy against cancer than other cisplatin compounds. Methods of delivery of those more effective cisplatin compounds to the nucleus in cancer cells is disclosed using one or more amino acids, one or more sugars, one or more polymeric ethers, $C_{1-6}$alkylene-phenyl-NH—C(O)—$R_{15}$, folic acid, $\alpha_v\beta_3$ integrin RGD binding peptide, tamoxifen, endoxifen, epidermal growth factor receptor, antibody conjugates, kinase inhibitors, diazoles, triazoles, oxazoles, erlotinib, and/or mixtures thereof; wherein $R_{15}$ is a peptide.

24 Claims, 23 Drawing Sheets

A

B

A

B

C

A

B

A

B

TARGETED DELIVERY AND PRODRUG DESIGNS FOR PLATINUM-ACRIDINE ANTI-CANCER COMPOUNDS AND METHODS THEREOF

The present application claims priority under 35 USC 371 to PCT/US12/53189 filed Aug. 30, 2012, which in turn claims priority under 35 USC 119 to U.S. Provisional Patent Application No. 61/530,746 filed Sep. 2, 2011, both of which are hereby incorporated by reference in their entireties.

STATEMENT REGARDING FEDERALLY SPONSORED RESEARCH OR DEVELOPMENT

Some aspects of this invention described in this application were sponsored by R01 CA 101880 (NIH/NCI). Accordingly, the Federal Government has rights in this application.

FIELD OF THE INVENTION

The present invention relates to new platinum containing compounds that show increased potency and efficacy in vitro and in vivo against certain types of cancer and compounds, compositions containing said compounds, and methods of delivering those compounds to treat these certain types of cancer.

BACKGROUND OF THE INVENTION

Cisplatin is an inorganic platinum agent (cis-diamminedichloroplatinum or cis-DDP) with anti-neoplastic activity, which forms highly reactive, charged, platinum complexes which bind to nucleophilic groups such as GC-rich sites in DNA, inducing intrastrand and interstrand DNA cross-links, as well as DNA-protein cross-links. These cross-links result in apoptosis and cell growth inhibition.

Formation of any platinated coordination complex with DNA is not sufficient for cytotoxic (that is, cell-killing) activity. The corresponding trans isomer of cisplatin (namely, trans-DDP) also forms a coordination complex with DNA but unlike cisplatin, trans-DDP is not an effective chemotherapeutic agent.

Cisplatin has been shown effective against small-cell lung cancer (SCLC), testicular cancers, ovarian carcinomas, various head and neck cancers, and patients with lymphomas. However, better drugs are always desired that have greater potency and less toxicity. Moreover, there are certain types of cancer against which cisplatin is not effective.

Previously, health care workers have used cisplatin in combination therapies to treat cancer. However, despite the hope that the drugs will work together, producing a synergistic, or at least an additive effect, to cure the cancer has proved elusive. Moreover, not only has combination therapy with cisplatin failed to show additive effects, there often have been other deleterious side effects caused by the combination therapy. Even if the side effects present in combination therapy are minimized, the costs often times prove to be prohibitive.

Some combination therapies have proved to be somewhat effective against certain types of cancers. An example that has been used is the combination of cisplatin with 5-fluorouracil to treat terminally ill colon carcinoma patients. In one study, the tumors in three of nine patients decreased in size by more than 50% for varying lengths of time. However, cisplatin alone showed no effect on colon cancers in phase I clinical trials.

Resistance to platinum drugs, perhaps the most serious drawback, is multifactorial in nature, which complicates the design of compounds able to circumvent the underlying resistance mechanisms. While certain tumors tend to acquire resistance after treatment with platinum, other forms of the disease are inherently chemoresistant. Non-small cell lung cancer (NSCLC), for instance, a major cause of cancer-related mortality worldwide, is notoriously insensitive to treatment with classical cytotoxic agents, including the first generation of platinum-based drugs. Despite the poor clinical prognosis of the disease, dual-agent regimens containing cisplatin (or less toxic carboplatin) in combination with a non-platinum agent are currently the only treatment options for patients with advanced NSCLC. This sobering fact demonstrates the urgent need for novel chemotypes to combat this aggressive form of cancer.

Cellular Uptake of Cisplatin

Cisplatin generally is administered to cancer patients intravenously as a sterile sodium chloride saline solution. Once cisplatin is in the bloodstream, it is believed that cisplatin remains intact due the relatively high concentration of chloride ions (~130-150 mM). The neutral compound is thought to enter the cell either by passive diffusion or active uptake.

Inside the cell, the neutral cisplatin molecule undergoes hydrolysis, in which a chlorine ligand is replaced by a molecule of water, generating a positively charged species. Hydrolysis occurs inside the cell because the concentration of chloride ion is much lower, in the range of ~3-20 mM.

The following reactions are the postulated mechanism for the process that occurs in the cell:

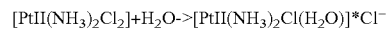

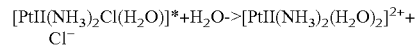

Cisplatin is thought to coordinate with DNA mainly through the N7 nitrogen on purine bases. Generally; these nitrogen atoms (specifically, the N7 atoms of purines) are free to coordinate to cisplatin because they do not form hydrogen bonds with any other DNA bases.

Many types of cisplatin-DNA coordination complexes, or adducts, can be formed. The most important of these appear to be the ones in which the two chlorine ligands of cisplatin are replaced by purine nitrogen atoms on adjacent bases on the same strand of DNA; these complexes are referred to as 1,2-intrastrand adducts. The purine bases most commonly involved in these adducts are guanines; however, adducts involving one guanine and one adenine are also believed to occur. Generally, the formation of these adducts causes the purines to become destacked and the DNA helix to become kinked.

It is postulated that binding affects both replication and transcription of DNA, as well as mechanisms of DNA repair. The effects of both cisplatin and trans platinum on DNA replication have been studied both in vitro (using cell extracts outside the host organism) and in vivo (inside the host organism). The mechanism is believed to invoke 1,2-intrastrand adducts between cisplatin and DNA, which stops all polymerases from processing (e.g., replicating and transcribing) DNA.

In order to overcome the problem of tumor resistance to known platinum compounds, other platinum compounds need to be developed that damage DNA radically differently than the classical cross-linkers. Novel types of cytotoxic lesions may evade the cellular DNA repair machinery and/or trigger cancer cell death by alternate mechanisms at the genomic level.

Unlike the clinical cross-linking agents, it would be desirable to develop compounds that damage DNA by a dual mechanism involving monofunctional platinum binding to guanine or adenine, and intercalation of certain moieties on compounds into the base pair step adjacent to the site of platination. Accordingly, it would also be desirable to develop compounds that do not mimic the action of cisplatin.

It would be desirable to develop compounds that show a strong cytotoxic effect in a broad range of solid tumors in vitro similar, or superior, to that of the presently available clinical drugs. It would be desirable to develop compounds that can be delivered to cells where the cytotoxic effect is needed and methods for their delivery including the ability to be delivered in spite of the body's defense mechanisms. It would also be desirable to develop compounds that prove effective against NSCLC cell lines of different genetic backgrounds.

The present invention discloses the groundbreaking discovery of alternative platinum based compounds that have a dramatic effect on the treatment of various types of cancer by employing unique biocoordination chemistry leading to heretofore unseen biological activity. Moreover, the compounds of the present invention can be delivered by various means to the cells where the cytotoxic effect is needed. Furthermore, the newly designed compounds of the present invention are the examples of hybrid agents that are able to slow progression of an inherently resistant form of cancer in vivo.

BRIEF SUMMARY OF THE INVENTION

The compounds of the present invention are dual platinating/intercalating DNA binders that, unlike clinical platinum agents, do not induce DNA cross-links. The compounds of the present invention lead to greatly enhanced cytotoxicity in several different types of cancers including effectiveness in NCI-H460 non-small cell lung cancer (NSCLC) cells, effectiveness against leukemia, and effective tumor growth inhibition in xenograft models. The compounds of the present invention are also designed so that they can be delivered to and/or sensitize cells that require the cytotoxic effect.

BRIEF DESCRIPTION OF THE SEVERAL VIEWS OF THE DRAWINGS

In FIG. 11A, the warhead compound is attached to an antibody that recognizes an eptitope on the cell surface of a tumor cell. Note that the linker region between the antibody and the warhead compound is enzymatically cleavable so that the warhead compound is free to perform its cytotoxic function.

FIG. 12A shows a kinase inhibitor compound linked to the warhead compound with a linker region that comprises a cleavable bond such as by a protease such as cathepsin B. FIG. 12B provides a schematic of the dual action therapy. Once the linker region between the kinase inhibitor and the warhead compound has been broken, the kinase inhibitor is free to impede the phosphorylation of a protein in a necessary cell process (such as signal transduction). The warhead at the same time is able to bind DNA providing two avenues for effectively targeting and killing a tumor cell. FIG. 12C shows an example of a cleavable ester-linked bifunctional conjugate featuring a platinum-acridine warhead and a kinase inhibitor.

FIG. 14A shows click activated chemistry of a 3+2 cycloaddition reaction wherein an alkyne group on the warhead compound (as shown by two of the compounds in FIG. 14B) reacts with an azide group that is attached to a fluorescent moiety to generate the 1,2,3 triazole 4-yl containing compound with the fluorescent probe. Alternatively, an azide group on the warhead compound (as shown by one of the compounds in 14B), which is attached to DNA (as shown in 14A) reacts with an alkyne-containing compound that has a fluorescent moiety attached to it to generate a 1,2,3-triazole-1-yl compound that still has the fluorescent moiety attached to it. A column or some other purification means might be used to isolate DNA, and the attached fluorescent probe containing the triazole containing compound will allow vizualization of the warhead compound as it is attached to DNA. This can potentially be used to quantitate the amount of warhead compound that is attached to DNA and monitor drug uptake and sub-cellular distribution.

DETAILED DESCRIPTION OF THE INVENTION

Figure 1:
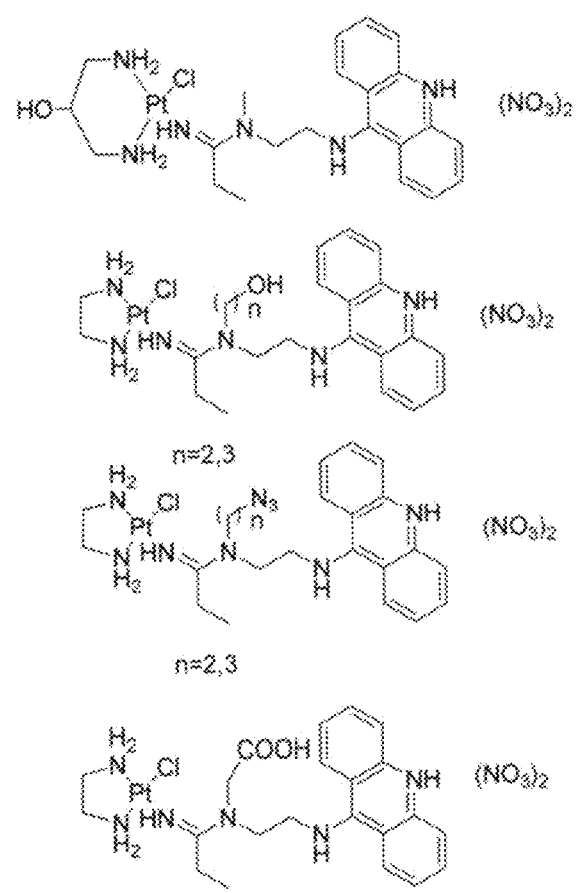
FIG. 1 shows several of the compounds of the present invention.

To overcome the problem of tumor resistance to platinum drugs, agents that damage DNA radically differently than the classical cross-linkers have been designed. The rationale behind the approach of the compounds described herein is that novel types of cytotoxic lesions may evade the cellular DNA repair machinery and/or trigger cancer cell death by alternate mechanisms at the genomic level. Platinum-acridinylthiourea conjugates, represented by the prototype, [PtCl(en)(ACRAMTU-S)]($NO_3$)$_2$ (1) ("PT-ACRAMTU"; en=ethylenediamine, ACRAMTU=1-[2-(acridin-9-ylamino)ethyl]-1,3-dimethylthiourea), are a class of cationic DNA-targeted hybrid agents designed toward this goal. Unlike clinical cross-linking agents (and without being bound by the proposed mechanism), the compounds of the present invention damage DNA by a dual mechanism involving monofunctional platinum binding to guanine or adenine, and intercalation of the acridine moiety into the base pair step adjacent to the site of platination. These adducts and the structural perturbations they produce in DNA do not mimic cisplatin's. Thus, the compounds of the present invention are effective against certain cancers that traditional cisplatin compounds are not. Thus, in an embodiment of the present invention it is contemplated and therefore within the scope of the invention that combination therapy can be used including using the compounds of the present invention along with compounds that act by a different mechanism such as more traditional first generation cisplatin compounds and their derivatives. Other combination therapies are contemplated by using those compounds known by those of skill in the art and/or those disclosed and discussed infra.

Despite its charged nature and inability to induce DNA cross-links, two features violating the classical chemical requirements for antitumor activity in cisplatin-type complexes, the compounds of the present invention show a strong cytotoxic effect in a broad range of solid tumors in vitro similar, or superior, to that of known clinical drugs. The thiourea derivative compound's cytotoxicity did not translate into inhibition of tumor growth in vivo. This discrepancy prompted several structure-activity relationship (SAR) studies with the ultimate goal of generating an analogue endowed with clinically useful antitumor activity. Modifications were made to the linker geometry, the spectator ligands on the metal center and the intercalating portion of the molecule. However, none of the derivatives showed a major advantage over the thiourea acridine compound and some of the modifications compromised the compounds' aqueous solubility. After diligent and laborious work, one chemical modification shows a dramatic effect on the biocoordination chemistry and biological activity of this type of conjugate: the replacement of the thiourea sulfur with an amidine nitrogen as the donor atom connecting the metal and intercalator moieties. The newly designed amidine compounds are the first example of this type of hybrid agent able to slow progression of an inherently resistant form of cancer in vivo.

In an embodiment, the present invention relates to compounds, methods, and processes of getting the compounds to the site wherein the compounds can demonstrate their cytotoxic activity. In a variation of the embodiment, the platinum containing compounds of the present invention are modified by inserting/incorporating a reactive group at a particular position of the platinum-containing compound to which a linker and various chemical moieties can be attached. In an embodiment, sometimes these chemical moieties will allow the platinum containing compound (i.e., the warhead compound) to get through the cell wall and into the nucleus. In other embodiments, these chemical moieties will sometimes act as anticancer agents themselves or sensitize the cells to the DNA-damaging effects of the platinum-acridine warheads. In a variation, these chemical moieties when acting as an anticancer agent will work by a different mechanism than that of the warhead compounds. In other embodiments, these chemical moieties will sometimes allow the addition of still other chemical moieties that can be used as identification means. In still other embodiments, the linker group may be a chemical moiety that allows it to be cleaved. For example, if the linker is a peptide, a protease that targets the particular peptide may be used to cleave the linker. Alternatively and/or additionally, the linker may be designed so that a rearrangement occurs that causes atoms to be lost from the warhead.

In an embodiment, the present invention also relates to a plurality of compounds that can be used to treat cancer. These acridine containing platinum compounds have been shown to be effective against particularly aggressive and chemoresistant forms of cancer that other platinum containing compounds are unable to treat.

In one embodiment, the compounds of the present invention are defined by Formula I.

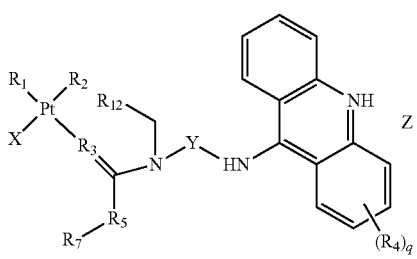

Formula I wherein X is halo, $OC(O)R_9$, nitrate or sulfate;

$R_1$ and $R_2$ are amino groups or together with the platinum atom to which they are attached, $R_1$ and $R_2$ form the ring $-NH_2-(CH_2)_v-NH_2-$ wherein v is 1, 2, 3, or 4 or $R_1$ and $R_2$ together can be any of the following groups a-h;

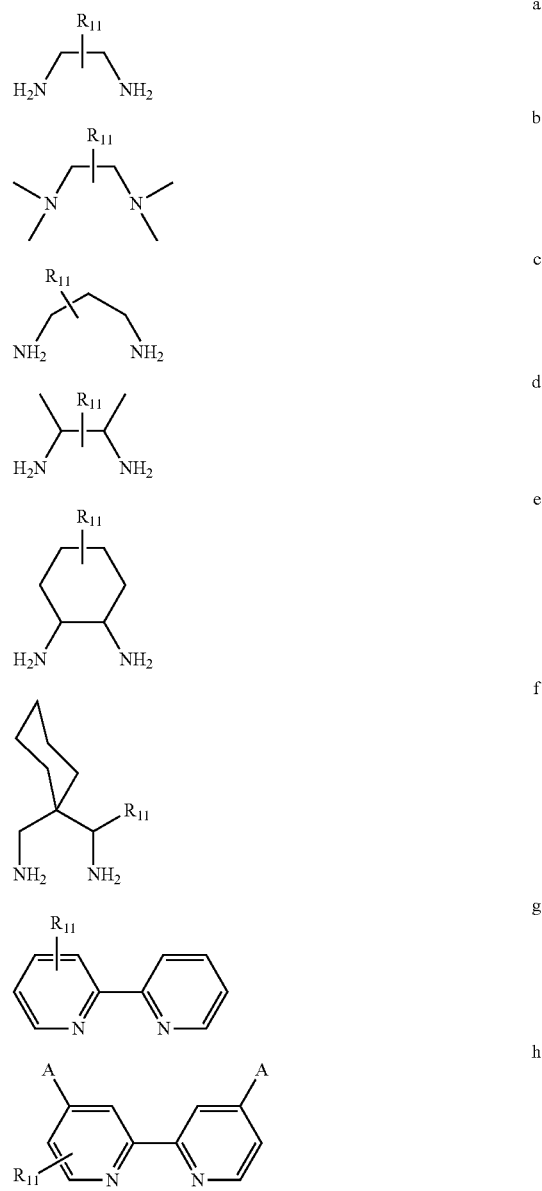

wherein A is H, $-CH_3$, $-OCH_3$, $CF_3$ or $NO_2$;

$R_3$ is $-N(R_6)-$; wherein $R_6$ is hydrogen or $C_1$-$C_6$alkyl;

$R_4$ is independently an amino, a nitro, $-NHC(O)(R_{10})$, $-NHC(O)O(R_{10})$, $-C(O)NHR_{10}$, $-OC(O)NHR_{10}$, or halo;

$R_{10}$ is hydrogen, $C_{1-6}$alkyl, phenyl, naphthyl, $C_{3-6}$cycloalkyl, norbornyl, or adamantyl;

q is 0, 1, or 2;

$R_5$ is a direct bond, $-NH-$ or $C_1$-$C_6$alkylene;

or $R_5$ and X together with the atoms to which they are attached form a 6- or 7-membered ring, wherein said 6- or 7-membered ring contains a linking group $-C(O)O-$ or $-OC(O)-$;

$R_7$ is hydrogen, methyl, or —C(O)O—$R_8$; wherein $R_8$ is hydrogen, $C_{1-6}$ alkyl, phenyl, naphthyl, $C_{3-6}$ cycloalkyl, norbornyl, adamantyl, a natural or unnatural amino acid or a peptide;

$R_9$ is hydrogen, $C_{1-6}$ alkyl, phenyl, naphthyl, $C_{3-6}$ cycloalkyl, norbornyl, adamantyl, a natural or unnatural amino acid or a peptide;

either or both of $R_{11}$ and $R_{12}$ contain a reactive group on to which a linker and/or one or more of compound W can be added; and if only one of $R_{11}$ and $R_{12}$ contains a reactive group, then the other of $R_{11}$ and $R_{12}$ is hydrogen;

Y is $C_1$-$C_6$ alkyl; and

Z is one or more counterions sufficient to balance the charge of the compound.

In an embodiment, $R_{11}$ and $R_{12}$ are —OH, —$N_3$, —COOH, —$CONH_2$, —CH=$CH_2$, —C≡CH, —$(CH_2)_{1-6}$—OH, —$(CH_2)_{1-6}$—$N_3$, —$(CH_2)_{1-6}$—COOH, —$(CH_2)_{1-6}$—CH=$CH_2$, —$(CH)_{1-6}$≡CH, —$(CH_2)_{0-1}$(—$OCH_2CH_2)_{1-6}$—OH, —$(CH_2)_{0-1}$(—$OCH_2CH_2)_{1-6}$—$N_3$, or —$(CH_2)_{0-1}$(—$OCH_2CH_2)_{1-6}$—COOH;

In an embodiment, $R_{11}$ and $R_{12}$ combined with the linker and compound W are —NH—$R_{13}$,

—O—$R_{13}$, —CH=CH—$R_{13}$, —C≡C—$R_{13}$,

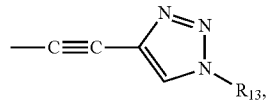

—$N_3$, —COOH, —$COOR_{14}$, —C(O)NH—$R_{13}$, —NHC(O)—$R_{13}$, —OC(O)NH—$R_{13}$, —OC(O)O—$R_{13}$, —$(CH_2)_{1-6}$—NH—$R_{13}$,

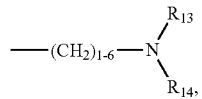

—$(CH_2)_{1-6}$—O—$R_{13}$, —$(CH_2)_{1-6}$—$N_3$, —$(CH)_{1-6}$—COOH, —$(CH_2)_{1-6}$—$COOR_{14}$ or —$(CH_2)_{1-6}$—CH=CH—$R_{13}$;

wherein $R_{13}$ and $R_{14}$ are independently selected from the group consisting of one or more amino acids, one or more sugars, polymeric ethers, PAMAM (Poly(amido amine)) Dendrimers such as carboxylate-modified PAMAM Dendrimers. PLGA (poly(lactic-co-glycolic acid)), -triazol-$R_{15}$, $C_{1-6}$alkylene-phenylene-NH—C(O)—$R_{15}$, folic acid, fatty acid, and polyunsaturated fatty acid (PUFA), $\alpha_\nu\beta_3$ integrin RGD binding peptide, tamoxifen, endoxifen, EGFR (epidermal growth factor receptor) antibody conjugates, kinase inhibitors, diazoles, triazoles, oxazoles, erlotinib, and mixtures thereof wherein $R_{15}$ is a peptide;

In an alternate embodiment, the compounds of the present invention include the compounds of Formula II:

Formula II

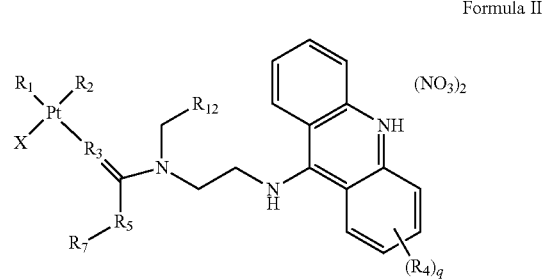

wherein X is halo, —OC(O)$R_9$, nitrate or sulfate;

$R_1$ and $R_2$ are amino groups or together with the platinum atom to which they are attached, $R_1$ and $R_2$ form the ring —$NH_2$—$(CH_2)_\nu$—$NH_2$— wherein v is 1, 2, 3, or 4 or $R_1$ and $R_2$ together can be any of the following groups a-h,

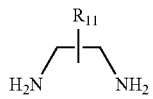
a

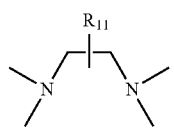
b

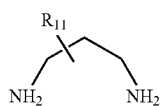
c

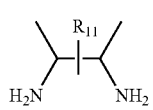
d

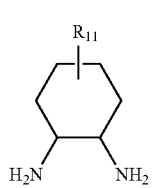
e

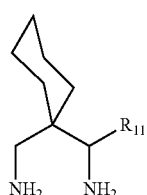
f

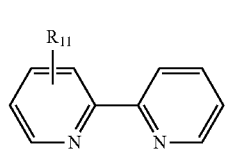
g

-continued

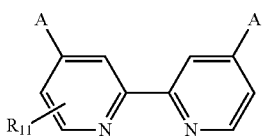

h

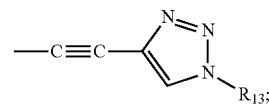

wherein A is H, —CH$_3$, —OCH$_3$, CF$_3$ or NO$_2$;

R$_3$ is —N(R$_6$)—, wherein R$_6$ is hydrogen or C$_1$-C$_6$alkyl;

R$_4$ is independently an amino, a nitro, —NHC(O)(R$_{10}$), —NHC(O)O(R$_{10}$), —C(O)NHR$_{10}$, —OC(O)NHR$_{10}$, or halo;

R$_{10}$ is hydrogen, C$_{1-6}$ alkyl, phenyl, naphthyl, C$_{3-6}$ cycloalkyl, norbornyl, or adamantyl;

q is 0, 1, or 2;

R$_5$ is a direct bond, —NH— or C$_1$-C$_6$alkylene;

or R$_5$ and X together with the atoms to which they are attached form a 6- or 7-membered ring, wherein said 6- or 7-membered ring contains a linking group —C(O)O— or —OC(O)—;

R$_7$ is hydrogen, methyl, or —C(O)O—R$_8$; wherein

R$_8$ is hydrogen, C$_{1-6}$ alkyl, phenyl, naphthyl, C$_{3-6}$ cycloalkyl, norbornyl, or adamnantyl, a natural or unnatural amino acid or a peptide;

R$_9$ is hydrogen, C$_{1-6}$ alkyl, phenyl, naphthyl, C$_{3-6}$ cycloalkyl, norbornyl, or adamantyl;

either or both of R$_{11}$ and R$_{12}$ contain a reactive group on to which a linker and/or one or more of compound W can be added; and if only one of R$_{11}$ and R$_{12}$ contains a reactive group, then the other of R$_{11}$ and R$_{12}$ is hydrogen.

In an embodiment, R$_{11}$ and R$_{12}$ are —OH, —N$_3$, —COOH, —CONH$_2$, —CH═CH$_2$, —C≡CH, —(CH$_2$)$_{1-6}$—OH, —(CH$_2$)$_{1-6}$—N$_3$, —(CH$_2$)$_{1-6}$—COOH, —(CH$_2$)$_{1-6}$—CH═CH$_2$, —(CH$_2$)$_{1-6}$—C≡CH, —(CH$_2$)$_{0-1}$(—OCH$_2$CH$_2$)$_{1-6}$—OH, —(CH$_2$)$_{0-1}$(—OCH$_2$CH$_2$)$_{1-6}$—N$_3$, or —(CH$_2$)$_{0-1}$(—OCH$_2$CH$_2$)$_{1-6}$—COOH;

In an embodiment, R$_{11}$ and R$_{12}$ in combination with the linker and compound W are —NH—R$_{13}$,

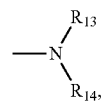

—O—R$_{13}$, —CH═CH—R$_{13}$, —C≡C—R$_{13}$, —N$_3$, —COOH, —COOR$_{14}$, —CONH$_2$, —C(O)NH—R$_{13}$, —NHC(O)—R$_{13}$, —OC(O)NH—R$_{13}$, —OC(O)O—R$_{13}$, —(CH$_2$)$_{1-6}$—NH—R$_{13}$,

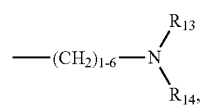

—(CH$_2$)$_{1-6}$—O—R$_{13}$, —(CH$_2$)$_{1-6}$—N$_3$, —(CH$_2$)$_{1-6}$—COOH, —(CH$_2$)$_{1-6}$—COOR$_{14}$ or —(CH$_2$)$_{1-6}$—CH═CH—R$_{13}$, wherein R$_{13}$ and R$_{14}$ are independently selected from the group consisting of one or more amino acids, one or more sugars, polymeric ethers, PAMAM (Poly(amido amine)) Dendrimers, PLGA (poly(lactic-co-glycolic acid)), -triazol-R$_{15}$, C$_{1-6}$alkylene-phenyl-NH—C(O)—R$_{15}$, folic acid, fatty acids, PUFAs, α$_v$β$_3$ integrin RGD binding peptide, tamoxifen, endoxifen. EGFR (epidermal growth factor receptor) antibody conjugates, kinase inhibitors, diazoles, triazoles, oxazoles, erlotinib, and mixtures thereof wherein R$_1$, is a peptide;

In a further embodiment, the present invention is directed to compounds of Formula III:

Formula III

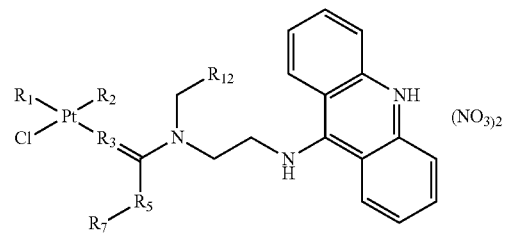

wherein

R$_1$ and R$_2$ are amino groups or together with the platinum atom to which they are attached, R$_1$ and R$_2$ form the ring —NH—(CH$_2$)$_v$—NH$_2$— wherein v is 1,2,3, or 4 or R$_1$ and R$_2$ together can be any of the following groups a-h;

a

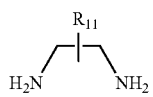

b

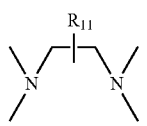

c

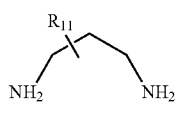

d

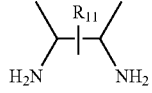

e

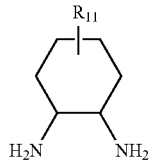

-continued

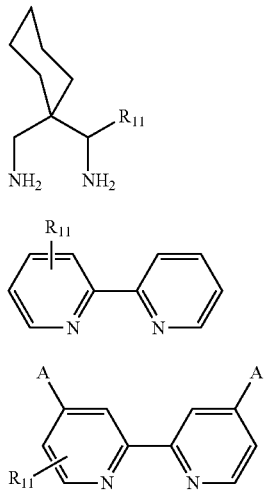

wherein

A is H, —CH₃, —OCH₃, CF₃ or NO₂;

R₃ is —N(R₆)—, wherein R₆ is hydrogen or $C_1$-$C_6$alkyl;

R₄ is independently an amino, a nitro, —NHC(O)(R₁₀), —NHC(O)O(R₁₀), —C(O)NHR₁₀, —OC(O)NHR₁₀, or halo;

R₁₀ is hydrogen, $C_{1-6}$ alkyl, phenyl, naphthyl, $C_{3-6}$ cycloalkyl, norbornyl, or adamantyl;

q is 0, 1, or 2;

R₅ is a direct bond, —NH— or $C_1$-$C_6$alkylene;

or R₅ and X together with the atoms to which they are attached form a 6- or 7-membered ring, wherein said 6- or 7-membered ring contains a linking group —C(O)O— or —OC(O)—;

R₇ is hydrogen, methyl, or —C(O)O—R₈; wherein

R₈ is hydrogen, $C_{1-6}$ alkyl, phenyl, naphthyl, $C_{3-6}$ cycloalkyl, norbornyl, or adamantyl, a natural or unnatural amino acid or a peptide;

R₉ is hydrogen, $C_{1-6}$ alkyl, phenyl, naphthyl, $C_{1-6}$ cycloalkyl, norbornyl, or adamantyl;

either or both of R₁₁ and R₁₂ contain a reactive group on to which a linker and/or one or more of compound W can be added; and if only one of R₁₁ and R₁₂ contains a reactive group, then the other of R₁₁ and R₁₂ is hydrogen.

In an embodiment, R₁₁ and R₁₂ are —OH, —N₃, —COOH, —CONH₂, —CH=CH₂, —C≡CH, —(CH₂)₁₋₆—OH, —(CH₂)₁₋₆—N₃, —(CH)₁₋₆—COOH, —(CH₂)₁₋₆—CH=CH₂, —(CH₂)₁₋₆—C≡CH, —(CH₂)₀₋₁(—OCH₂CH₂)₁₋₆—OH, —(CH₂)₀₋₁(—OCH₂CH₂)₁₋₆—N₃, or —(CH₂)₀₋₁(—OCH₂CH₂)₁₋₆—COOH;

In an embodiment, R₁₁ and R₁₂ in combination with the linker and compound W are —NH—R₃,

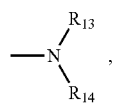

—O—R₁₃, —CH=CH—R₁₃, —C≡C—R₁₃, —N₃, —COOH, —COOR₁₄, —C(O)NH—R₁₃, —NHC(O)—R₁₃, —OC(O)NH—R₁₃, —OC(O)O—R₁₃, —(CH₂)₁₋₆—NH—R₁₃,

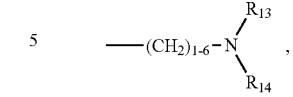

—(CH₂)₁₋₆—O—R₁₃, —(CH₂)₁₋₆—N₃, —(CH₂)₁₋₆—COOH, —(CH₂)₁₋₆—COOR₁₄, —(CH₂)₁₋₆—CH=CH—R₁₃ or

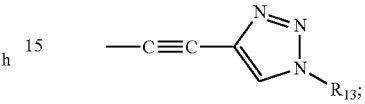

wherein R₁₃ and R₁₄ are independently selected from the group consisting of one or more amino acids, one or more sugars, polymeric ethers, PAMAM (Poly(amido amine)) Dendrimers, PLGA (poly(lactic-co-glycolic acid)), -triazol-R₁₅, $C_{1-6}$alkylene-phenyl-NH—C(O)—R₁₅, folic acid, fatty acids, PUFAs, $α_vβ_3$ integrin RGD binding peptide, tamoxifen, endoxifen, EGFR (epidermal growth factor receptor) antibody conjugates, kinase inhibitors, diazoles, triazoles, oxazoles, erlotinib, and mixtures thereof wherein R₁₅ is a peptide.

In an embodiment, when R₁₂ is not hydrogen, in addition to the above moieties a-h, R₁₁ may also be NH₃, NH₂(R₁₃), NH(R₁₃)₂, or N(R₁₃)₃ wherein R₁₃ is independently $C_1$-$C_6$alkyl.

In the present invention, "warhead compound" means a compound that contains a platinum atom and an acridine moiety.

$C_1$-$C_6$alkylene means both straight chain and branched alkylene moieties. For example $C_1$-$C_6$alkylene and $C_1$-$C_6$alkyl respectively include but are not limited to methylene, methyl, ethylene, ethyl, propylene, propyl, isopropylene, isopropyl, butylene, butyl, isobutylene, isobutyl, t-butylene, t-butyl, and other similar functionalities. Moreover, in all Formula that have an R₅ as part of the Formula, R₅ and the R₇ group that is attached to it can form any straight chain or branched alkyl group that has between 1 and 7 carbon atoms, such as methyl, ethyl, propyl, isopropyl, butyl, isobutyl, t-butyl, and the other similar moieties.

Fatty acids include both the C12-C22 saturated fatty acid, such as Lauric acid. Tridecylic acid, Myristic acid. Pentadecylic acid. Palmitic acid, Margaric acid and Stearic acid and so on, and poly unsaturated fatty acid (PUFC). For example, Palmitoleic acid, Oleic acid, Linoleic acid, Docosahexaenoic acid and other similar moieties.

Natural and unnatural amino acids include the twenty one amino acids that are coded for naturally as well as derivatives of those amino acids. These include alanine, cysteine, asparic acid, asparagine, glutamic acid, glutamine, phenylalanine, glycine, histidine, isoleucine, lysine, leucine, methionine, arginine, proline, serine, threonine, selenocysteine, valine, tryptophan, tyrosine, dimethyl glycine, ornithine, S-adenosylmethionine, canavanine, mimosine, 5-hydroxytryptophan, L-dihydroxyphenylalanine, Eflornithine, 2-aminoisobutyric acid, lanthionine, pyrrolysine. In an embodiment, the natural and unnatural amino acids include dimethyl glycine, alanine, phenylalaine and proline.

A peptide means a 2 to 10 mer of any combination of the amino acids listed above including any duplicates, triplicates, etc.

The natural and unnatural amino acids can be bonded either by the amino functionality or the carboxylate moiety.

It is contemplated and therefore within the scope of the invention that other zwitterionic functionalities can be used in place of the amino acids listed above.

In a variation of the embodiment, compounds of the present invention include Example 1 (note that this is the same compound as compound 14b).

Example 1

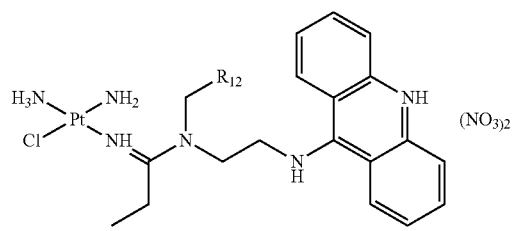

(NO$_3$)$_2$ wherein $R_{12}$ is as defined above.

In a variation of the embodiment, compounds of the present invention include Example 2.

Example 2

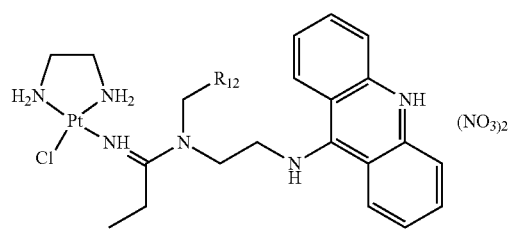

(NO$_3$)$_2$ wherein $R_{12}$ is as defined above.

General Preparative Method:

N-(acridin-9-yl)-N'-methylethane-1,2-diamine ("9-acridine-amine") is a common precursor that can be used to make the compounds of the present invention.

"9-acridine-amine"

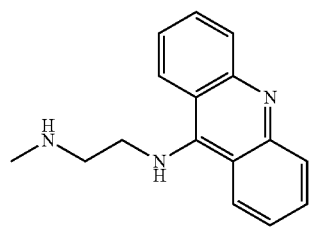

Chloro ligand(s) in platinum precursors can be substituted with propionitrile (EtCN). Subsequently, one equivalent of 9-acridine-amine is added to the intermediate to yield a platinum-amidine conjugate through an addition reaction to a metal-activated CN triple bond. For the synthesis of PT-ACRAMTU analogues, another equivalent of nitric acid can be added to the monocationic nitrate salts to mimic the PT-ACRAMTU dinitrate salt.

A general synthetic methodology and a generic procedure for making the compounds of the present invention are shown in the below schemes 1-8. The modified acridine amine moieties with various functional groups can be synthesized according to schemes 1-8 shown below.

Scheme 1 Alkyne analog of Acridine-Amine

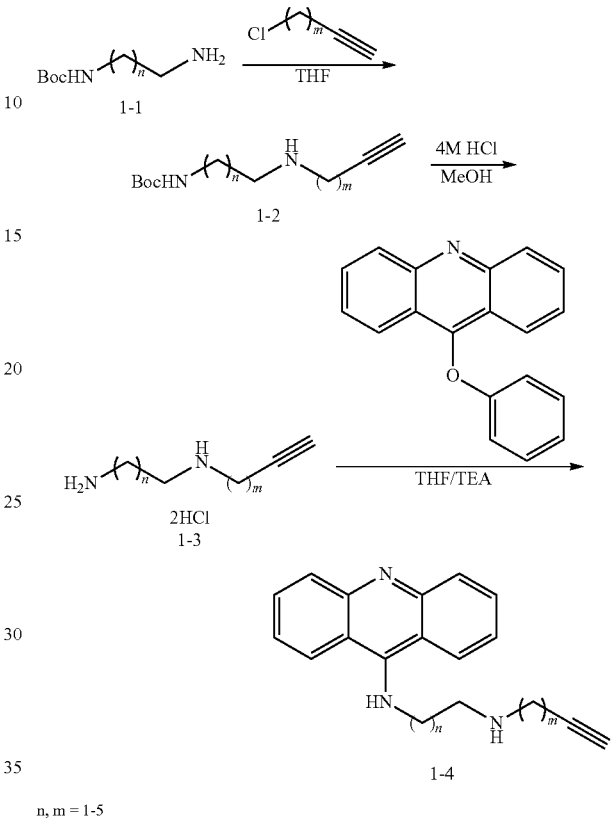

n, m = 1-5

Scheme 2 Hydroxyl analog of Acridine-Amine

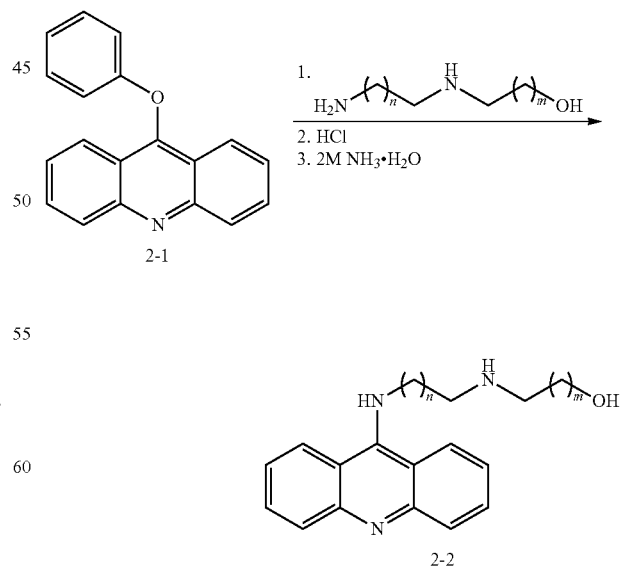

n, m = 1-5

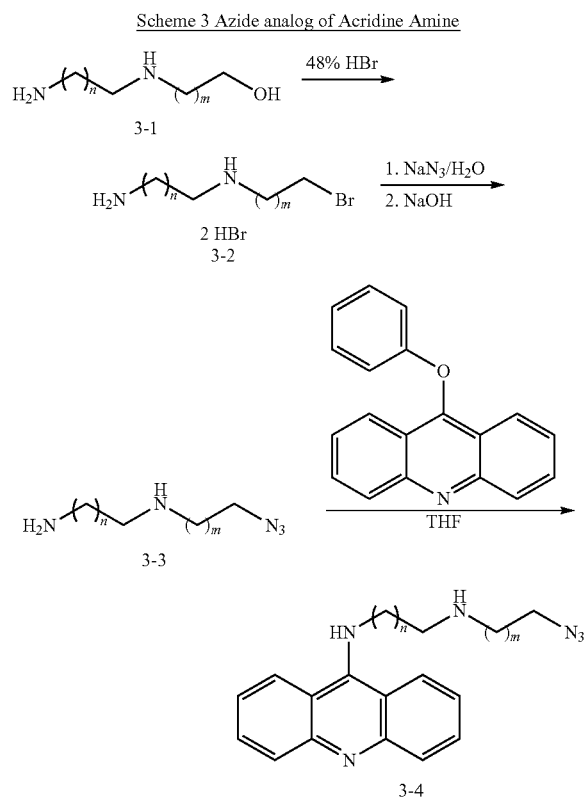
Scheme 3 Azide analog of Acridine Amine
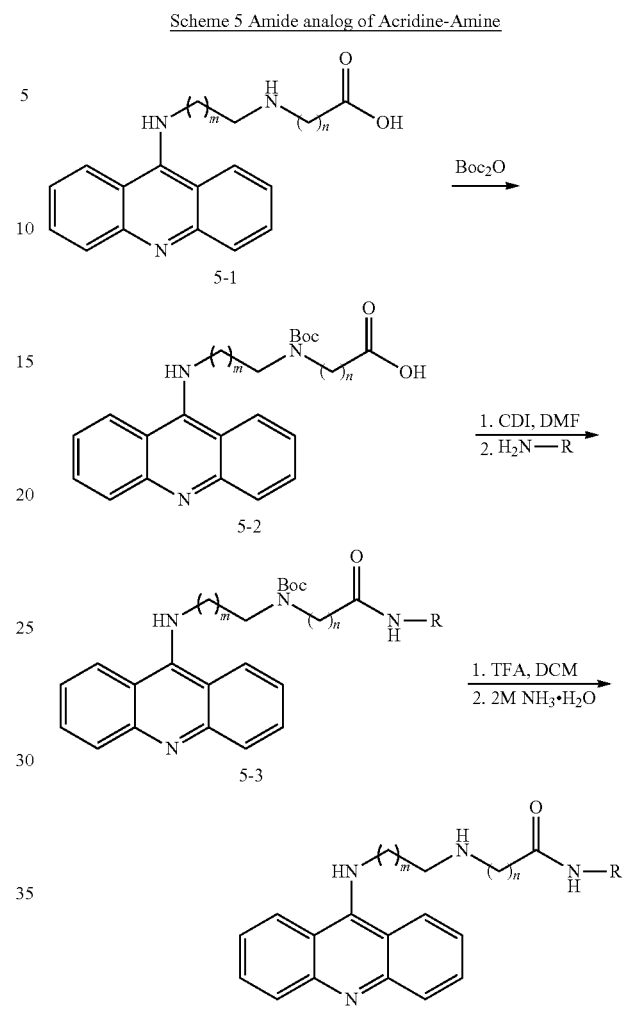
Scheme 5 Amide analog of Acridine-Amine
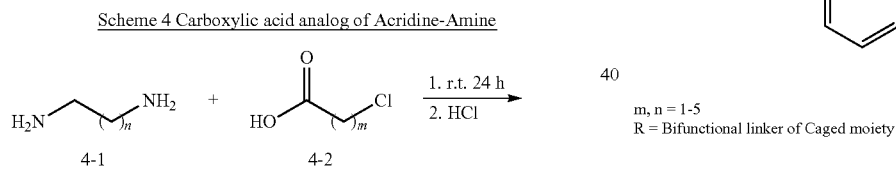
Scheme 4 Carboxylic acid analog of Acridine-Amine
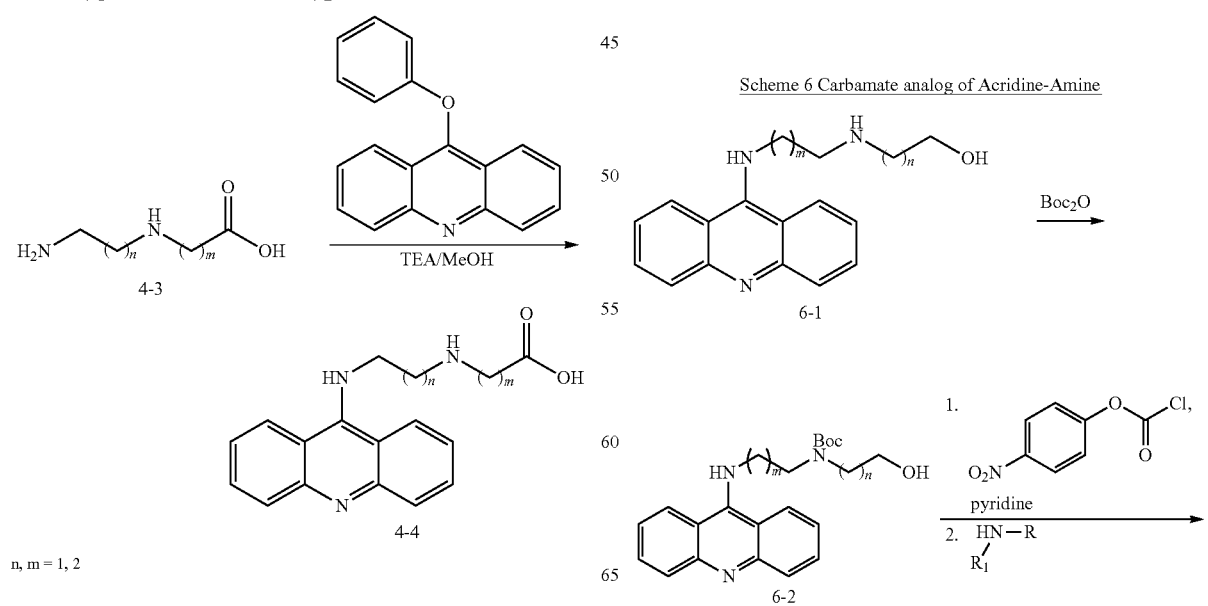
Scheme 6 Carbamate analog of Acridine-Amine
n, m = 1-5
m, n = 1-5
R = Bifunctional linker of Caged moiety
n, m = 1, 2

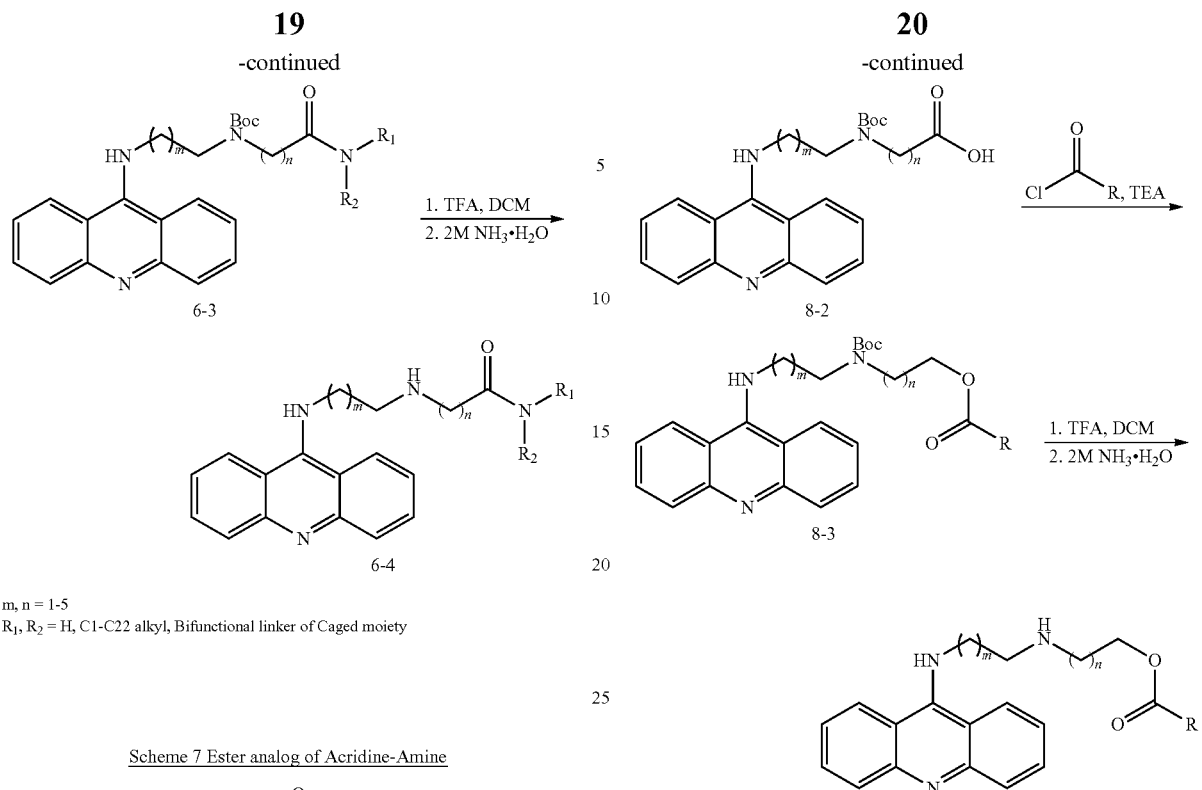
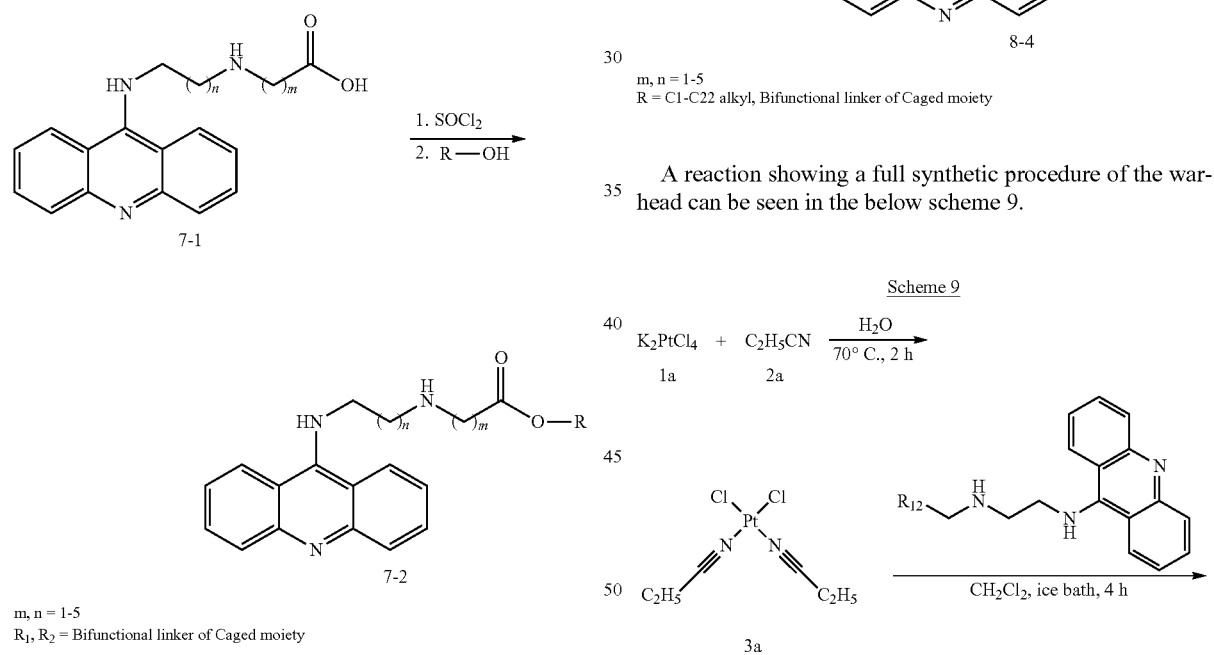
A reaction showing a full synthetic procedure of the warhead can be seen in the below scheme 9.
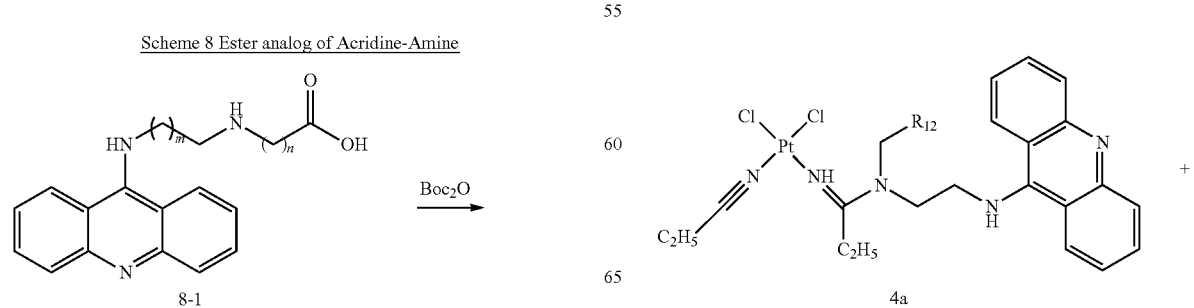

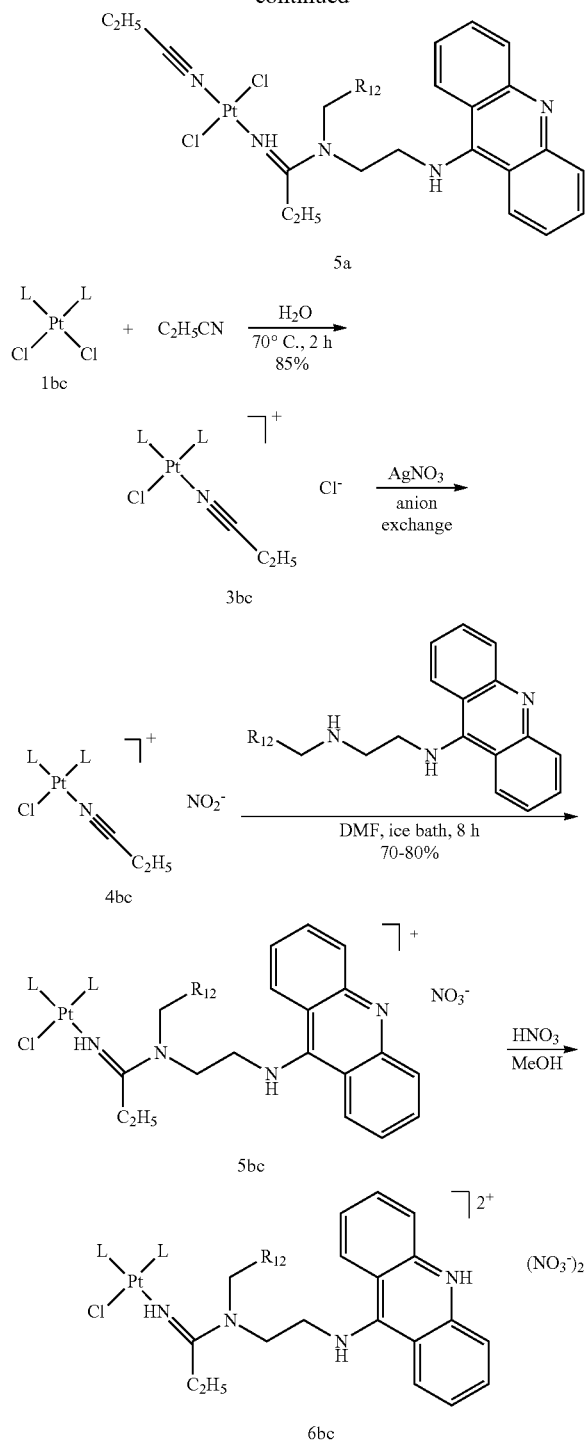
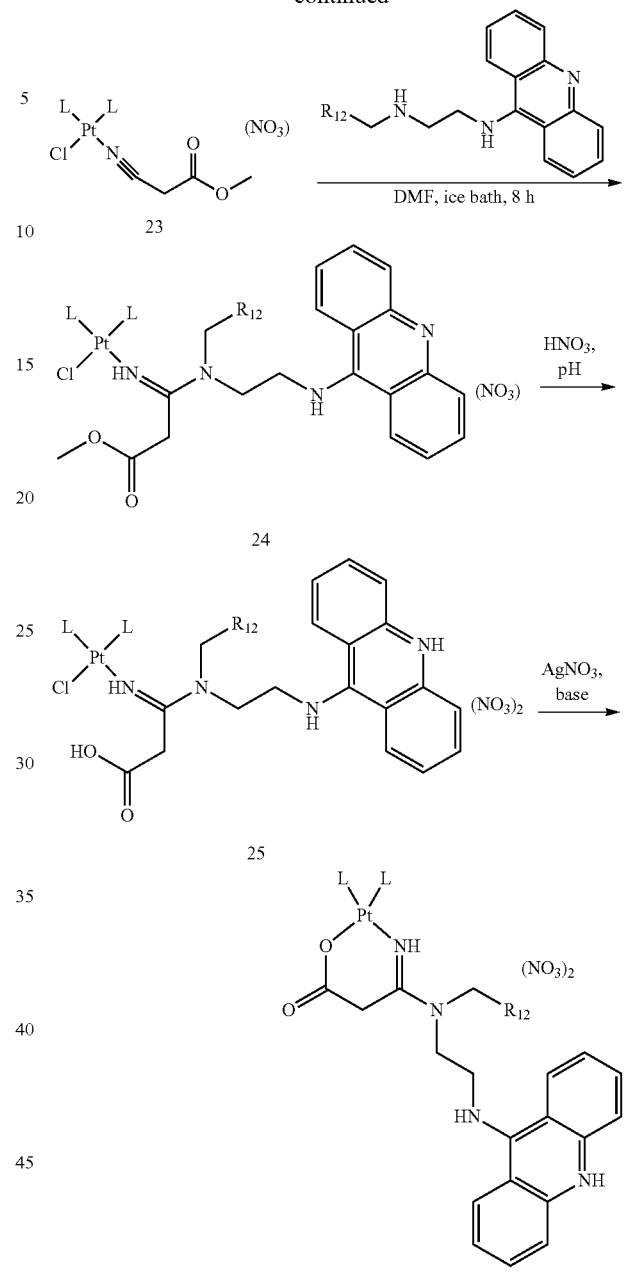

b: L₂ = en; c: L = NH₃

Scheme 10

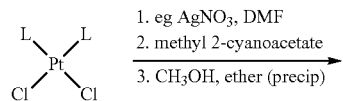

1. eg AgNO₃, DMF
2. methyl 2-cyanoacetate
3. CH₃OH, ether (precip)

The upper part of scheme 9 shows the methodology development for a synthetic scheme to generate mixtures of the cis and trans isomers of the acridinyl platinum compound. The lower synthetic scheme 10 shows a synthetic methodology combining the acridinyl moiety to the platinum moiety to generate as the principal product the cis isomer of the acridinyl platinum compound.

In the upper synthetic process of scheme 9, the tetrachloro platinum compound 1a is treated with ethyl nitrile to generate the bis cis-chloro bis N-linked propynyl compound 3a. Treatment with an acridinyl substituent generates a mixture of the trans and cis (bis chloro) isomers of the acridinyl platinum compound (compounds 4a and 5a).

Alternatively, in the lower synthetic scheme of scheme 9, the starting material is the bis cis chloro platinum compound that has alternative ligands that allow synthesis of the cis platinum acridinyl compound 6bc. In this synthetic process, the bis-cis-dichoroplatinum starting compound 1bc is reacted with the propionitrile compound 2bc to generate the cis-monochloro mono-N-linked propionitrile compound 4bc. Compound 4bc is subsequently reacted with an acridinyl compound to generate the acridinyl platinum 5bc, which when done in the presence of nitrous acid results in the cis acridinyl platinum salt represented by compound 6bc.

It should be noted that because $R_{12}$ contains a reactive functionality, this reactive functionality may need to have a protecting group added to it so that it does not react when making the acridinyl platinum salt. After the salt is made, the protecting group can be removed allowing the reactive functionality in $R_{12}$ to have the linker and/or compound W added to it. Protecting groups are well known to those of skill in the art. For example, the book Protecting Groups, Kocienski, P., $3^{rd}$ edition, publisher Geor Thieme Verlag, 2003 describes the protecting and deprotecting process. This book is incorporated by reference in its entirety.

Alternatively, a precursor functionality that will become the reactive group on $R_{12}$ can be used. Subsequent to the formation of the acridinyl platinum salt, this precursor functionality can be converted to the desired reactive group that is a part of $R_{12}$. For example, if an amine functionality is the reactive functionality that is a part of $R_{12}$, one might first incorporate a precursor that is an alkyl halide. The acridinyl platinum salt containing the alkyl halide can subsequently be converted into an azide (for example by the addition of $NaN_3$ in ethanol) and subsequently be reduced to the amine (using a reducing agent like $LiAlH_4$).

In scheme 10, it is shown how one can make a 6- or 7-membered compound 26. In scheme 10, one starts with bis cis chloro platinum compound and one uses one equivalent to generate the mono nitrile ester compound 23. To the mono nitrile ester compound 23, one adds the diamino acridine group to generate compound 24. Treatment with acid yields the corresponding acid functionality as shown in compound 25. Finally, cyclization occurs to generate the 6-membered lactone ring as shown in compound 26.

The above synthetic schemes can generally be followed to generate the compounds of the present invention. In one embodiment, the synthetic schemes can be used to generate the compounds of Formula II:

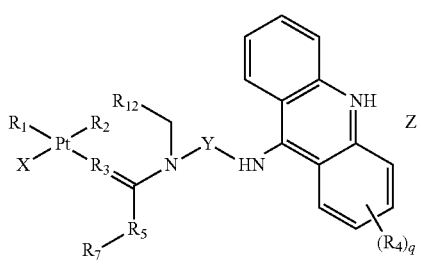

Formula I wherein X is halo, —OC(O)$R_9$, nitrate or sulfate;

$R_1$ and $R_2$ are amino groups or together with the platinum atom to which they are attached, $R_1$ and $R_2$ form the ring —$NH_2$—$(CH_2)_v$—$NH_2$— wherein v is 1, 2, 3, or 4 or $R_1$ and $R_2$ together can be any of the following groups a-h;

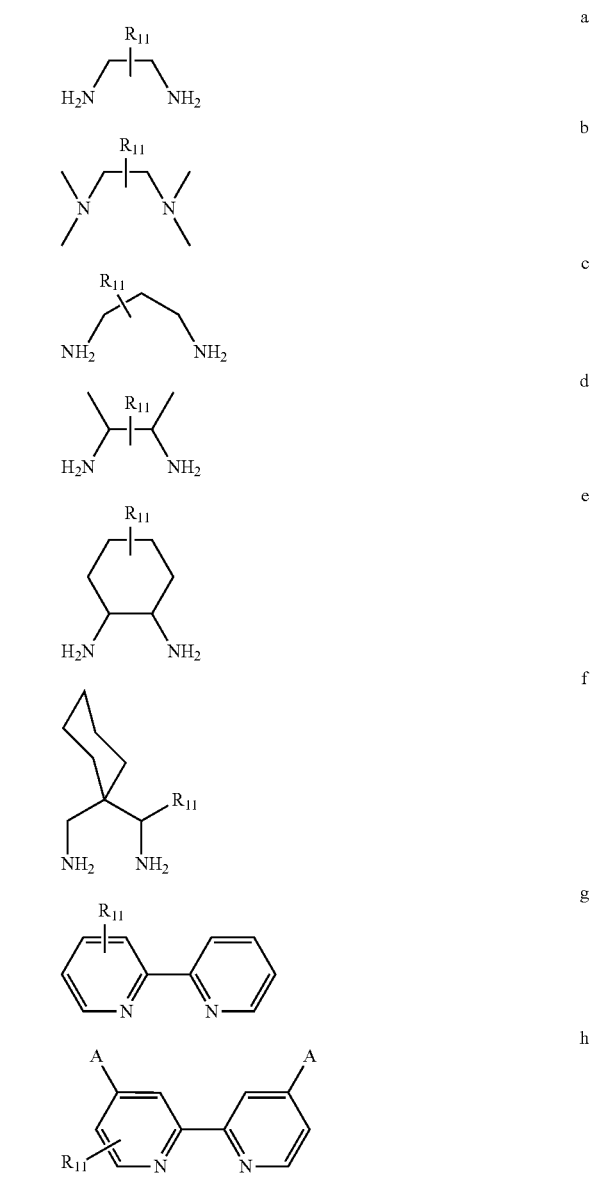

wherein A is H, —$CH_3$, —$OCH_3$, $CF_3$ or $NO_2$;
$R_3$ is —N($R_6$)—, wherein $R_6$ is hydrogen or $C_1$-$C_6$alkyl;
$R_4$ is independently an amino, a nitro, —NHC(O)($R_{10}$), —NHC(O)O($R_{10}$), —C(O)NH$R_{10}$, —OC(O)NH$R_{10}$, or halo;
$R_{10}$ is hydrogen, $C_{1-6}$ alkyl, phenyl, naphthyl, $C_{3-6}$ cycloalkyl, norbornyl, or adamantyl;
q is 0, 1, or 2;
$R_5$ is a direct bond, —NH— or $C_1$-$C_6$alkylene;
or $R_3$ and X together with the atoms to which they are attached form a 6- or 7-membered ring, wherein said 6- or 7-membered ring contains a linking group —C(O)O— or —OC(O)—;
$R_7$ is hydrogen, methyl, or —C(O)O—$R_8$; wherein
$R_8$ is hydrogen, $C_{1-6}$, alkyl, phenyl, naphthyl, $C_{3-6}$ cycloalkyl, norbornyl, or adamantyl, a natural or unnatural amino acid or a peptide;
$R_9$ is hydrogen, $C_{1-6}$ alkyl, phenyl, naphthyl, $C_{3-6}$ cycloalkyl, norbornyl, or adamantyl;
Y is $C_1$-$C_6$alkyl; and Z is one or more counterions sufficient to balance the charge of the compound;

either or both of $R_{11}$ and $R_{12}$ contain a reactive group on to which a linker and/or one or more of compound W can be added; and if only one of $R_{11}$ and $R_{12}$ contains a reactive group, then the other of $R_{11}$ and $R_{12}$ is hydrogen.

In an embodiment, $R_{11}$ and $R_{12}$ are —OH, —N$_3$, —COOH, —CONH$_2$, —CH=CH$_2$, —C≡CH, —(CH$_2$)$_{1-6}$—OH, —(CH$_2$)$_{1-6}$—N$_3$, —(CH)$_{1-6}$—COOH, —(CH$_2$)$_{1-6}$—CH=CH, —(CH$_2$)$_{1-6}$—C≡CH, —(CH$_2$)$_{0-1}$(—OCH$_2$CH$_2$)$_{1-6}$—OH, —(CH$_2$)$_{0-1}$(—OCH$_2$CH$_2$)$_{1-6}$—N$_3$, or —(CH$_2$)$_{0-1}$(—OCH$_2$CH$_2$)$_{1-6}$—COOH;

In an embodiment, $R_{11}$ and $R_{12}$ in combination with the linker and compound W are —NH—$R_{13}$,

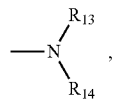

—O—$R_{13}$, —CH=CH—$R_{13}$, —C≡C—$R_{13}$, —N$_3$, —COOH, —COOR$_{14}$, —C(O)NH—$R_{13}$, —NHC(O)—$R_{13}$, —OC(O)NH—$R_{13}$, —OC(O)O—$R_{13}$, —(CH$_2$)$_{1-6}$—NH—$R_{13}$,

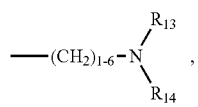

—(CH$_2$)$_{1-6}$, —O—$R_{13}$, —(CH$_2$)$_{1-6}$—N$_3$, —(CH$_2$)$_{1-6}$—COOH, —(CH$_2$)$_{1-6}$—COOR$_{14}$ or —(CH$_2$)$_{1-6}$—CH=CH—$R_{13}$, or

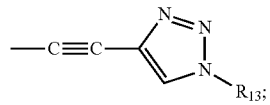

wherein $R_{13}$ and $R_{14}$ are independently selected from the group consisting of one or more amino acids, one or more sugars, polymeric ethers, PAMAM (Poly(amido amine)) Dendrimers, PLGA (poly(lactic-co-glycolic acid)), -triazol-$R_{15}$, $C_{1-6}$alkylene-phenyl-NH—C(O)—$R_{15}$, folic acid, fatty acids, PUFAs, $\alpha_v\beta_3$ integrin RGD binding peptide, tamoxifen, endoxifen, EGFR (epidermal growth factor receptor) antibody conjugates, kinase inhibitors, diazoles, triazoles, oxazoles, erlotinib, and mixtures thereof wherein $R_{15}$ is a peptide.

In an embodiment, when $R_{12}$ is not hydrogen, in addition to the above moieties a-h, $R_{11}$ may also be NH$_3$, NH$_2$($R_{13}$), NH($R_{13}$)$_2$, or N($R_{13}$)$_3$ wherein $R_{13}$ is independently $C_1$-$C_6$alkyl.

In a variation of this embodiment, the following variables may independently be represented as follows:

$R_3$ may be —N($R_6$)—,

Y may be —CH$_2$—, $R_1$ and $R_2$ may be amino groups or together with the platinum atom to which $R_1$ and $R_2$ are attached, they may be —NH$_2$—CH$_2$—NH$_2$—, the counter ion Z comprises NO$_3$.

$R_5$ may be —NH— or —CH$_2$—, or $R_5$ and X together with the atoms to which they are attached form a 6- or 7-membered ring, wherein said 6- or 7-membered ring contains a linking group —C(O)O— or —OC(O)—;

$R_7$ is hydrogen, methyl, or —C(O)O—$R_8$; wherein $R_8$ is hydrogen, $C_{1-6}$ alkyl, phenyl, naphthyl, $C_{3-6}$ cycloalkyl, norbornyl, or adamantyl, a natural or unnatural amino acid or a peptide;

$R_9$ is hydrogen, $C_{1-6}$ alkyl, phenyl, naphthyl, $C_{3-6}$ cycloalkyl, norbornyl, or adamantyl; and $R_6$ may be hydrogen or methyl.

In a variation, the general synthetic scheme can be used to generate the compound shown as Example 1 below:

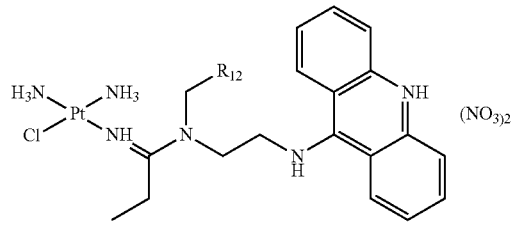

Example 1 wherein $R_{12}$ is as defined above.

In another variation, the general synthetic schemes above can be used to generate the compound that is Example 2:

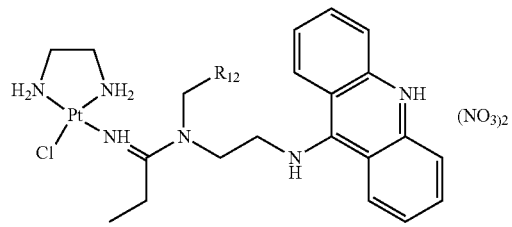

Example 2 wherein $R_{12}$ is as defined above.

In an embodiment, the compounds of the present invention can be used to treat cancer. Thus, in an embodiment, methods of treating cancer comprising administering to a subject in need thereof an effective amount of the compound of Formula I is within the scope of the present invention. In a variation, the methods of treating cancer include leukemia, lung cancer, testicular cancers, ovarian carcinomas, various head and neck cancers, and patients with lymphomas. In a further variation, the methods of treating cancer include leukemia. In a further variation, the methods of treating cancer include non-small cell lung cancer. In a further variation, the methods of treating cancer include cisplatin resistant ovarian cancers.

In an embodiment, the present invention relates to a plurality of different ways that the compounds of the present invention can be used to target various cancers. For example, the compounds of the present invention can have additional moieties attached to them that allow passage of the compounds to the desired area of the cell where the compounds are to work. As shown in FIG. 1, a hydroxyl moiety may be used (as shown in the top two compounds in FIG. 1). Note that the hydroxyl moiety can be present either as a substituent that emanates from the platinum containing ring, or alternatively, the hydroxyl group may be present on the linker region between the platinum atom and the acridine ring. Other possible moieties are azide moieties or carboxylic acid moieties. It should be understood that these various moieties (e.g., the hydroxyl groups, azide and carboxylic acid groups) are reactive functionalities that allow the addition of other groups, for example, peptides, other organic moieties, for example, kinase inhibitors or receptors, other natural products, antibodies, polymers, or combinations thereof. Alternatively, the other moieties that are linked to the warhead in the other figures in this application can also be used.

Figure 2:
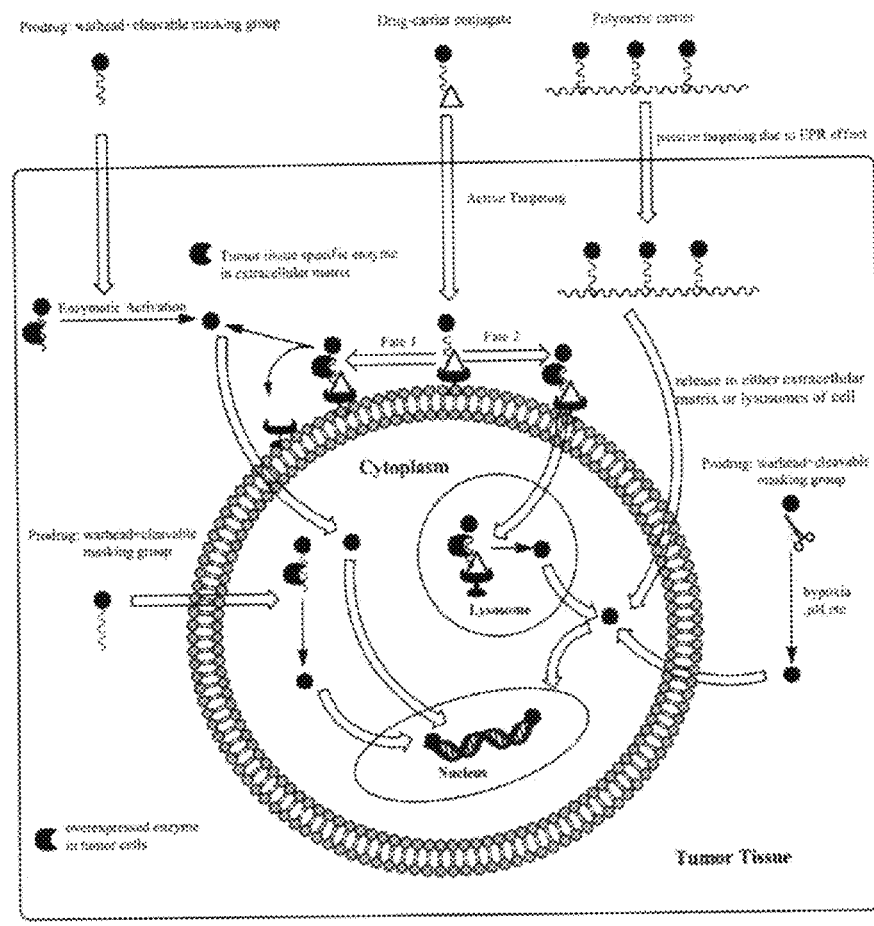
FIG. 2 shows the different ways that the compounds of the present invention can be used to target various cancers. For example, and as shown in the figure, the compounds of the present invention can have additional moieties attached to them that allow passage of the compounds to the desired area of the cell where the compounds are to work.

FIG. 2 provides an overview of the present invention and shows the many different ways that the compounds of the present invention can be used to target cancer. For example, and as shown in the figure, the compounds of the present invention can have additional moieties attached to them that allow passage of the compounds to the desired area of the cell where the compounds are to work. It is contemplated and therefore within the scope of the invention that combinations of these disclosed ways can be used allowing the compounds of the present invention to target cancer cells. For example, active targeting can be employed in combination with enzymatic activation.

Figure 3:
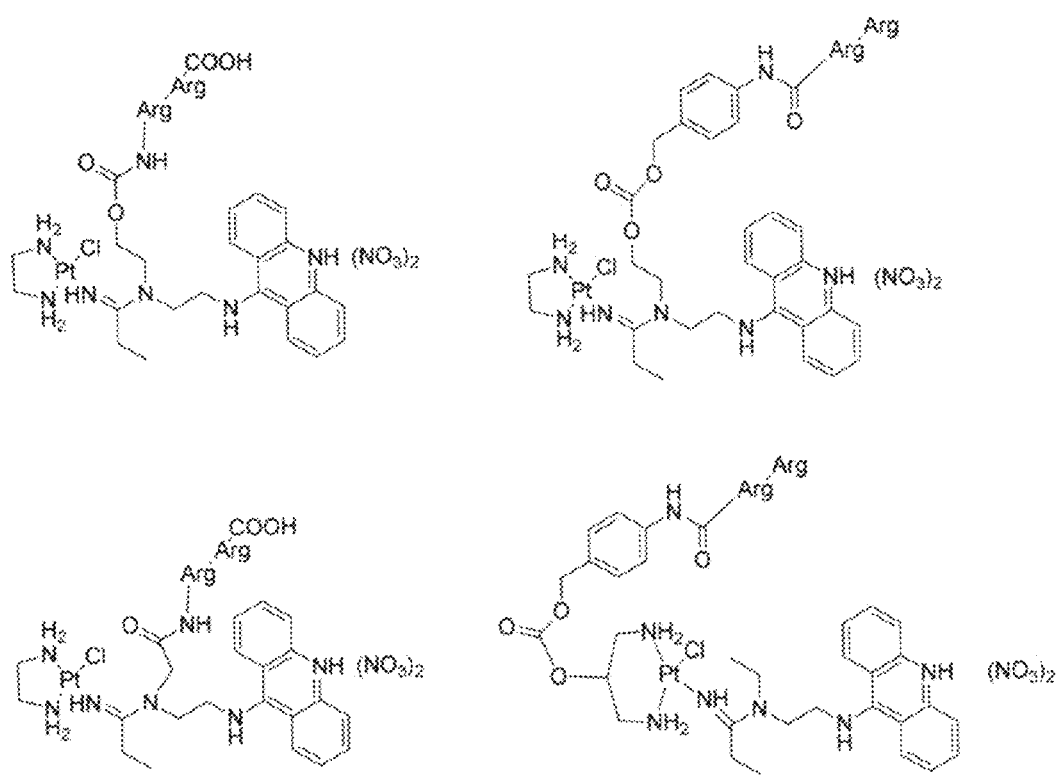
FIG. 3 shows compounds of the present invention with a linker and compound W (compound W is not shown in the figure but compound W in this figure and throughout the written description refers to a moiety that can be used to target a particular location in a cell and is usually attached to a linker moiety, wherein the linker is also attached to the warhead compound—i.e., the compound that effectuates the desired biological effect of being cytotoxic) attached to the compound. The additional moieties allow these compounds to pass the cell's defense systems and to arrive at the location(s) where they are to act as cytogenic compounds.

FIG. 3 shows some examples of the various functionalities that can be added to the compounds of the present invention. The upper left compound in FIG. 3 can be generated from a hydroxyl functionality that can be reacted with an isocyanate functionality to generate compounds similar to the carbamate compound (e.g., the upper left compound) in FIG. 3. Alternatively, an ester can be reacted with a carbonic acid derivative to generate the carbonate compound as shown as the upper right and lower right compound in FIG. 3. Alternatively, phosgene (ClC(O)Cl) can be reacted with one equivalent of an alcohol and reacted with one equivalent of a different alcohol to generate similar carbonate compounds to that shown on the upper right or lower right in FIG. 3.

A carboxylic acid (or acid halide) can be reacted with an amine to generate the amide shown on the bottom left of FIG. 3.

In the manufacture of these compounds, different moieties can be added that allow the compounds to serve a particular purpose, such as possessing a moiety that binds a particular receptor that allow the passage of the compound across a cell membrane. Although the compounds in FIG. 3 all possess the peptide Arg-Arg, it should be understood that any moiety can be present that allows it to achieve the desired purpose. The warhead part of the compound however continues to act as a cytogenic compound.

Figure 4:
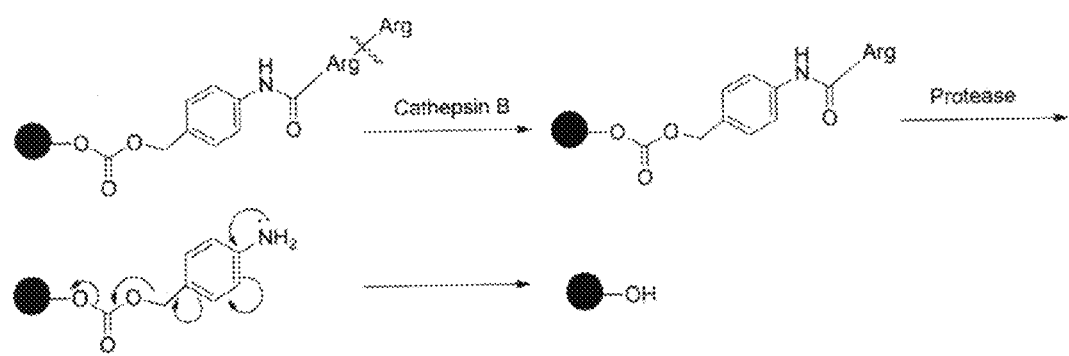
FIG. 4 shows a method by which the compounds containing both linkers and compound W may work to become active cytogenic compounds. In this proposed mechanism, cathepsin B selectively cleaves the Arg-Arg bond and a protease may remove the residual Arginine, whereupon when it is removed, an internal rearrangement will allow the carbonic acid ester to decompose to generate the active compound as one product.

FIG. 4 shows a method by which the compounds containing both linkers and the warhead compound (indicated by the circle attached to the carbonic acid ester) may work to become simply an active cytogenic compound. In this proposed mechanism, cathepsin B selectively cleaves the Arg-Arg bond and subsequently, a protease may remove the residual Arginine, whereupon when the Arg is removed, an internal rearrangement will allow the carbonic acid ester to decompose to generate the active compound as one product. The product is now available to be the cytogenic compound that it was designed to be. The Arg-Arg peptide may allow the warhead compound to arrive at a position in the body (or in a cell) that it would not normally be able to reach (similar to a Trojan horse). Removal of the peptide and linker region (by decomposition) will allow the isolated warhead compound to achieve it desired cytogenic effect.

Figure 5:
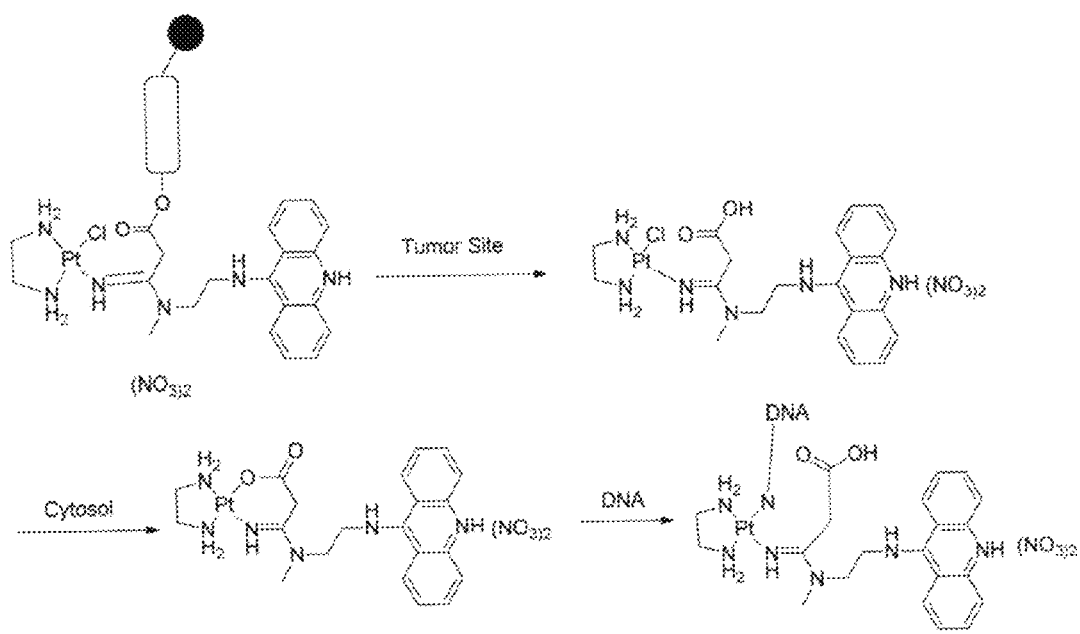
FIG. 5 shows another mechanism in which a compound of the present invention has a linker (a tumor specific cleavable bond) and compound W (caged group or targeting moiety) that are removed when the compound reaches the tumor site. Moreover, there may be a brief formation of a six-membered ring (with the platinum), which upon encountering the DNA at the tumor site may open up wherein the compound attaches to the DNA allowing the compound to act as an anticancer agent.

FIG. 5 shows another mechanism in which a compound of the present invention has a linker (a tumor specific cleavable bond) attached to another moiety (such as a caged group or targeting moiety) that are removed when the warhead compound reaches the tumor site. Note that because the platinum containing moiety has a chloride atom, which serves as a leaving group, and a carboxylic acid (which serves as a nucleophile), there may be the brief formation of a six-membered ring (with the platinum), which upon encountering DNA at the tumor site may open up whereupon the compound attaches to the DNA allowing the warhead compound to act as an anticancer agent (which it is designed to do).

Figure 6:
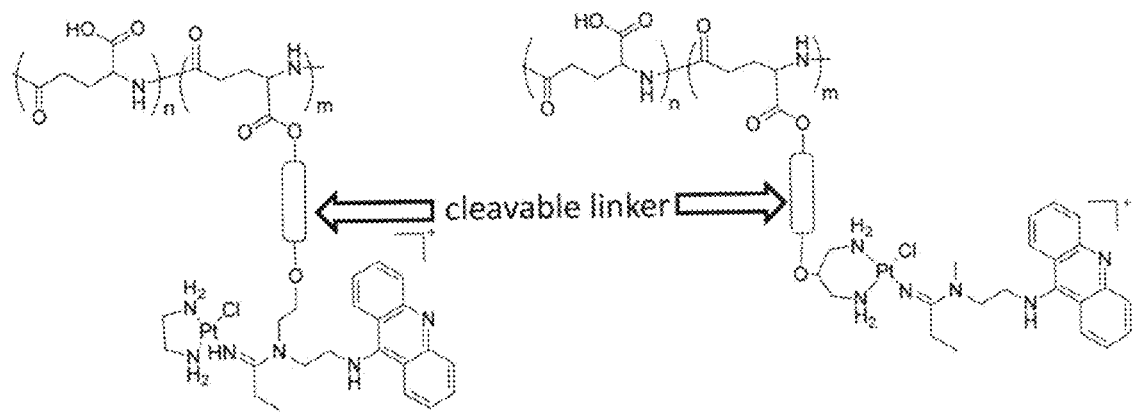
FIG. 6 shows a compound similar to FIG. 5 except the compound is shown with a bit more detail in that compound W is polyglutamic acid.

FIG. 6 shows a mechanism similar to FIG. 5 except the mechanism is shown with a bit more detail (in that compound W is polyglutamic acid). Note that the cleavable linker can be attached at several positions. The compound on the left has an oxygen attached to the amine functionality in the linker region between the platinum containing moiety and the acridine containing moiety. The compound on the right has the linker and the polyglutamate attached to an oxygen on the six membered ring (which includes the platinum atom).

Figure 7:
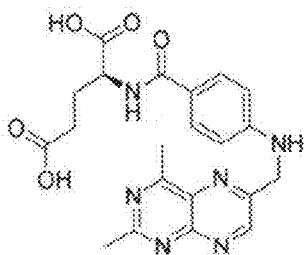
FIG. 7A shows folic acid and FIG. 7B shows the introduction of a drug (e.g., the compounds of the present invention) into a cell by endocytosis wherein the drug forms a complex with folic acid. The terminal carboxylic acid group (i.e., the carboxylic acid wherein the carbon adjacent to the carbonyl has two hydrogens attached to it) on folic acid provides a covalent binding avenue by which the drugs of the present invention may bind folic acid. Because there are folate receptors on the cell surface of a tumor cell (shown in 7B), the folic acid complex containing the warhead drug gets incorporated into the cell as an endosome whereupon the warhead compound can be released in the cell allowing the warhead compound to perform its cytotoxic function of binding the DNA in the cell, thereby providing cancer treatment.
Figure 7:
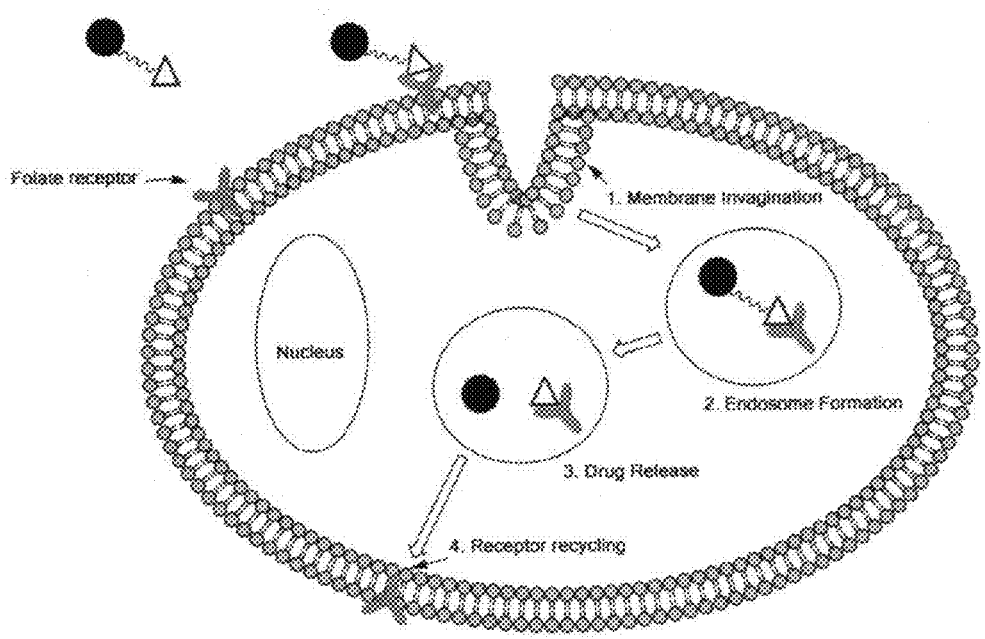

FIG. 7A shows folic acid and FIG. 7B shows the introduction of a drug (e.g., the compounds of the present invention) into a cell by endocytosis wherein the drug forms a complex with folic acid. The terminal carboxylic acid group (i.e., the carboxylic acid wherein the carbon adjacent to the carbonyl has two hydrogens attached to it) on folic acid provides a covalent binding avenue by which the drugs of the present invention may bind folic acid. Because there are folate receptors on the cell surface of a tumor cell (shown in 7B), the folic acid complex containing the warhead drug gets incorporated into the cell as an endosome whereupon the warhead compound can be released in the cell allowing the warhead compound to perform its cytotoxic function of binding the DNA in the cell (in the nucleus as shown in the figure, or alternatively, in the mitochondria where mitochondrial DNA exists), thereby providing cancer treatment. Note that the cell may recycle the folate receptor making it available to bind further folic acid moieties, which may have the warhead compound attached to it.

Figure 8:
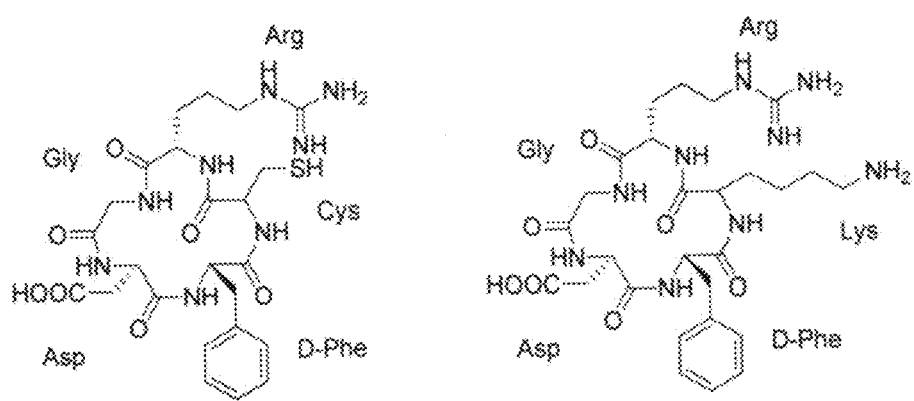
FIGS. 8A and 8B show two $\alpha_v\beta_3$ integrin binding RGD peptides, which can be bonded to the compounds of the present invention (i.e., the warhead compound) allowing the warhead compound to preferentially target cells that have a receptor for these tumor targeting peptides. With regards to 8A, the thiol group on the cysteine is a point of attachment. In 8B, the terminal amino group on the lysine moiety is a point of attachment for the warhead compound.

FIGS. 8A and 8B show two $\alpha_v\beta_3$ integrin binding RGD peptides, which can be bonded to the compounds of the present invention (i.e., the warhead compound) allowing the warhead compound to preferentially target cells that have a receptor for these tumor targeting peptides. With regards to 8A, the thiol group on the cysteine is a potential point of attachment. Alternatively, the carboxylic acid on the Aspartic acid moiety or the terminal amino (or imino) functionality on the Arg can be used. In 8B, the terminal amino group on the lysine moiety is a point of attachment for the warhead compound. Alternatively, the carboxylic acid on the Aspartic acid moiety or the terminal amino (or imino) functionality on the Arg can be used.

Figure 9:
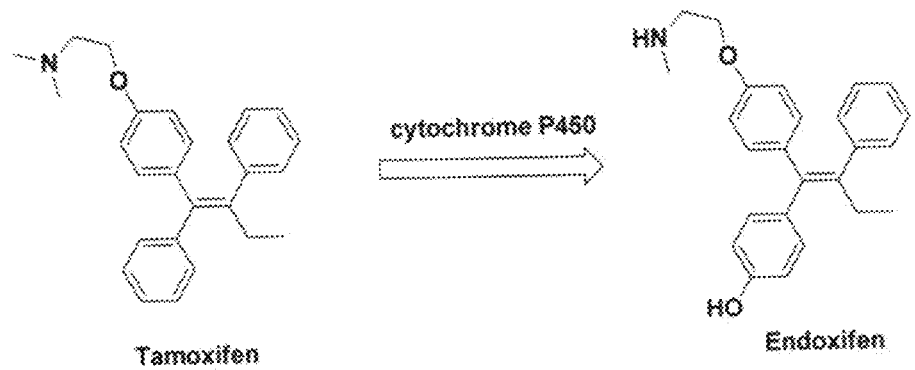
FIG. 9A shows the conversion of tamoxifen to endoxifen by cytochrome P450 in the liver.
FIG. 9B shows the warhead compound attached to tamoxifen.
FIG. 9C shows a warhead compound covalently attached to endoxifen via the secondary amine in tamoxifen. A linker region consisting of an amide group with two arginine amino acids provides the linkage between the warhead compound and the endoxifen. Endoxifen is the active metabolite that binds the estrogen receptor and is known to bind 30-100 times more efficiently than tamoxifen. Accordingly, the warhead compound can be attached to endoxifen and be used against breast cancer. The warhead compound can be freed by cleavage with cathepsin B (or some other protease).
Figure 9:
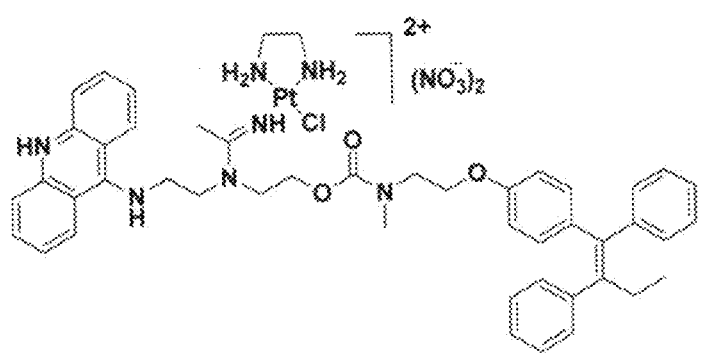
Figure 9:
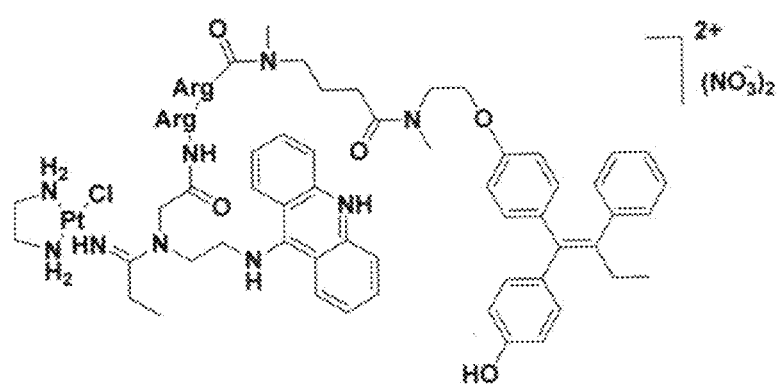

FIG. 9A shows the conversion of tamoxifen to endoxifen by cytochrome P450 in the liver. FIG. 9 B shows the warhead compound covalently attached to the secondary amine from tamoxifen (with a linker region). FIG. 9C shows a warhead compound covalently attached to endoxifen via the secondary amine in tamoxifen. A linker region consisting of an amide group with an alkylene linker and another amide group attached to two arginine amino acids provides the linkage between the warhead compound and the endoxifen. Endoxifen is the active metabolite that binds the estrogen receptor and is known to bind 30-100 times more efficiently than tamoxifen (presumably a result of the additional hydroxyl group). Accordingly, the warhead compound can be attached to endoxifen and be used against breast cancer. The warhead compound can be freed by cleavage with cathepsin B (or some other protease) allowing the warhead compound to provide its cytotoxic effect.

Figure 10:
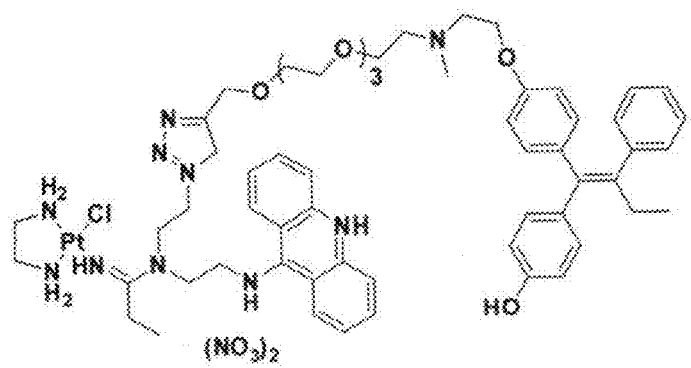
FIGS. 10A and 10B show a Trojan horse strategy wherein the warhead compound is attached via a polyether linkage to endoxifen (see 10A). In this instance, the polyether linkage is not easily cleavable but the endoxifen binds the estrogen receptor allowing passage of the warhead compound into the cytosol (see 10B) of a breast cancer tumor cell. Because estrogen receptor is also present in the cytosol (10B), the presence of estrogen receptor will also allow passage of the warhead compound into the nucleus wherein it can bind DNA (see 10B).
Figure 10:
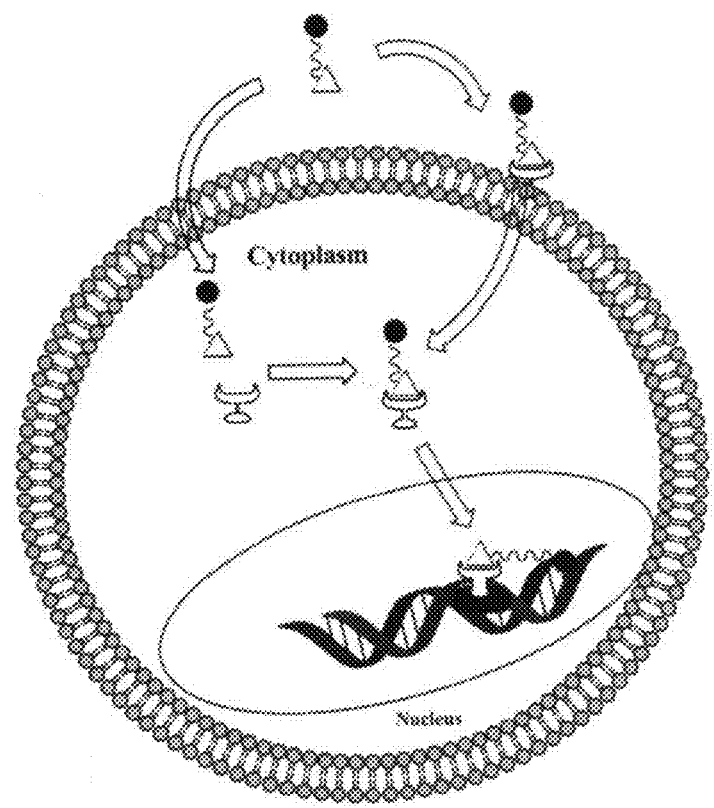

FIGS. 10A and 10B show a Trojan horse strategy wherein the warhead compound is attached via a polyether linkage to endoxifen (see 10A). In this instance, the polyether linkage is not easily cleavable but the endoxifen binds the estrogen receptor allowing passage of the warhead compound into the cytosol (see 10B) of a breast cancer tumor cell. Because the estrogen receptor is ubiquitous throughout the cell and its ability to cross many of the membranes in a cell (10B) will allow the passage of the estrogen receptor attached to the warhead compound into the nucleus wherein the warhead compound can bind DNA (see 10B) and perform its cytotoxic effect. The estrogen receptor also binds a nuclear receptor which in turn binds DNA allowing the warhead compound to come into close proximity to DNA and allowing the warhead compound to perform its cytotoxic function.

Figure 11:
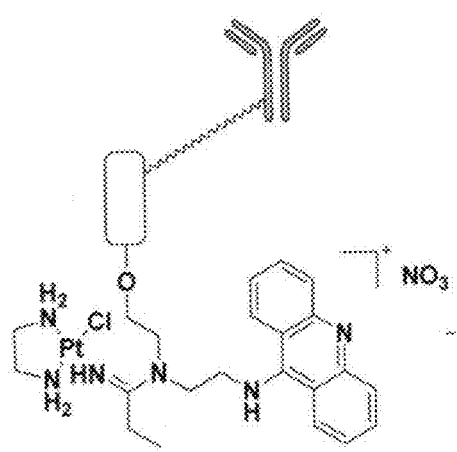
FIG. 11A shows antibodies that allow the identification of targeted tumor cells.

FIG. 11A shows antibodies that allow the identification of targeted tumor cells. In FIG. 11A, the warhead compound is attached to an antibody that recognizes an epitope on the cell surface of a tumor cell. Note that the linker region between the antibody and the warhead compound is enzymatically cleavable so that the warhead compound is free to perform its cytotoxic function. Although not shown, it is contemplated that an antibody may be attached to a monocyte, which allows the targeting and the lysis of the tumor cell. Thus, this mechanism in an embodiment provides an avenue for employing a dual methodology of attacking cancer cells (e.g., having the antibody attached to both the warhead compound as well as a monocyte).

Figure 12:
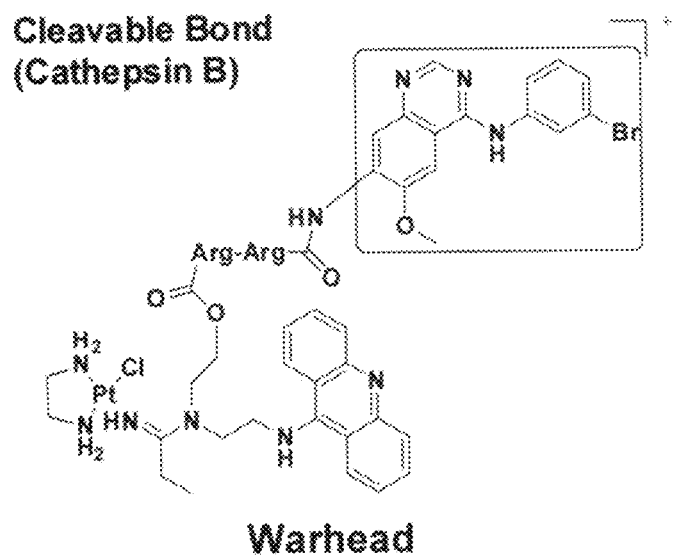
FIGS. 12A, 12B, and 12C show a dual action therapy.
Figure 12:
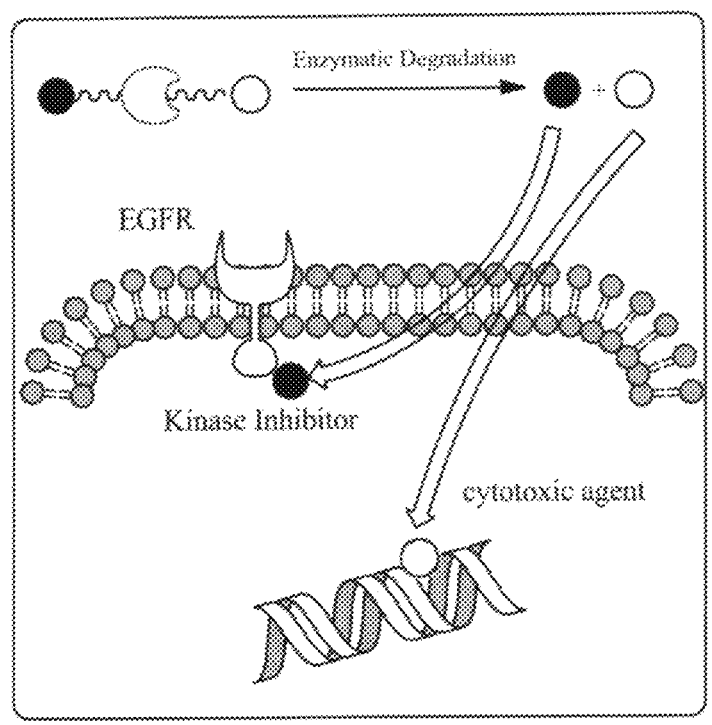
Figure 12C:
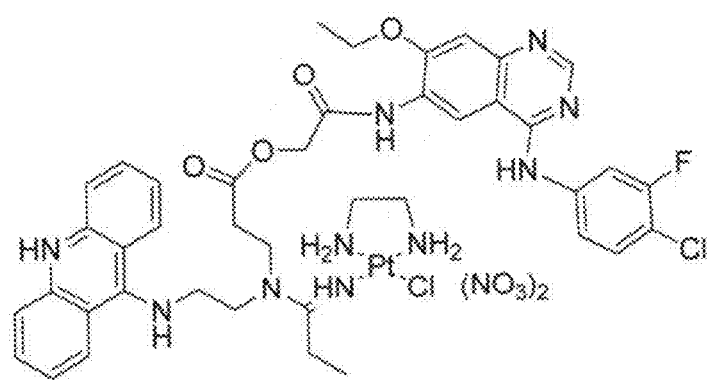

FIGS. 12A and 12B show dual action therapy. FIG. 12A shows a kinase inhibitor compound linked to the warhead compound with a linker region that comprises a cleavable bond such as by a protease such as cathepsin B. FIG. 12B provides a schematic of the dual action therapy. Once the linker region between the kinase inhibitor and the warhead compound has been broken, the kinase inhibitor is free to impede the phosphorylation of a protein in a necessary cell process (such as signal transduction). The warhead at the same time is able to bind DNA providing two avenues for effectively targeting and killing a tumor cell. In lieu of a kinase inhibitor, it should be understood that other compounds that inhibit necessary cellular processes can be used. It should also be understood that either of both of these compounds or other compounds that adversely affect cellular processes may be linked to any of the other compounds that are shown in the various figures that allow entry into the cell or allow passage of any cell membrane.

Figure 13:
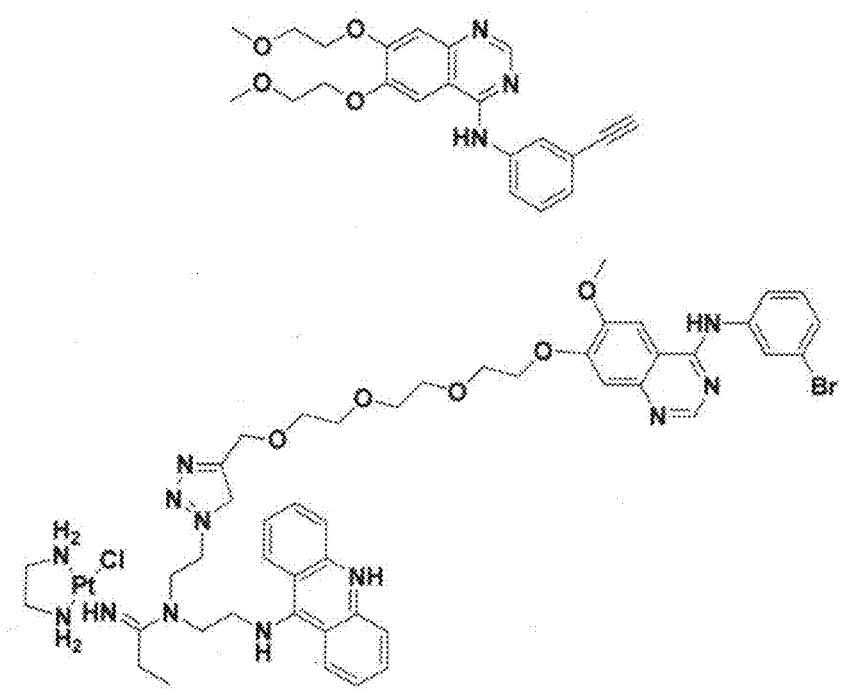
FIG. 13A shows erlotinib, which is known to be effective in treating various types of cancer including small cell lung cancer, pancreatic cancer, and several other types of cancer. The mechanism of action is that erlotinib is known to target the epidermal growth factor receptor (EGFR) tyrosine kinase, which is highly expressed and occasionally mutated in various forms of cancer.
FIG. 13B shows another quinazoline compound, which has structural similarities to erlotinib, with a polyether linker, which is attached to the warhead compound. This compound may be doubly effective against certain cancers as it has the quinazoline moiety, which likely mimics the action of erlotinib acting on EGFR tyrosine kinase, and it also has the warhead compound, which binds DNA.

FIG. 13A shows erlotinib, which is known to be effective in treating various types of cancer including small cell lung cancer, pancreatic cancer, and several other types of cancer. The mechanism of action is that erlotinib is known to be target the epidermal growth factor receptor (EGFR) tyrosine kinase, which is highly expressed and occasionally mutated in various forms of cancer. FIG. 13B shows another quinazoline compound, which has structural similarities to erlotinib, with a polyether linker, which is attached to the warhead compound. This compound may be doubly effective against certain cancers as it has the quinazoline moiety, which likely mimics the action of erlotinib acting on EGFR tyrosine kinase, and it also has the warhead compound, which binds DNA. It should be understood that erlotinib may also be used in conjunction with the warhead compound to affect dual action therapy on cancer cells. The acetylenyl moiety provides a potential place of attachment. Alternatively, the secondary amine also provides a potential place of attachment for a linker that may be attached to the warhead compound.

Figure 14:
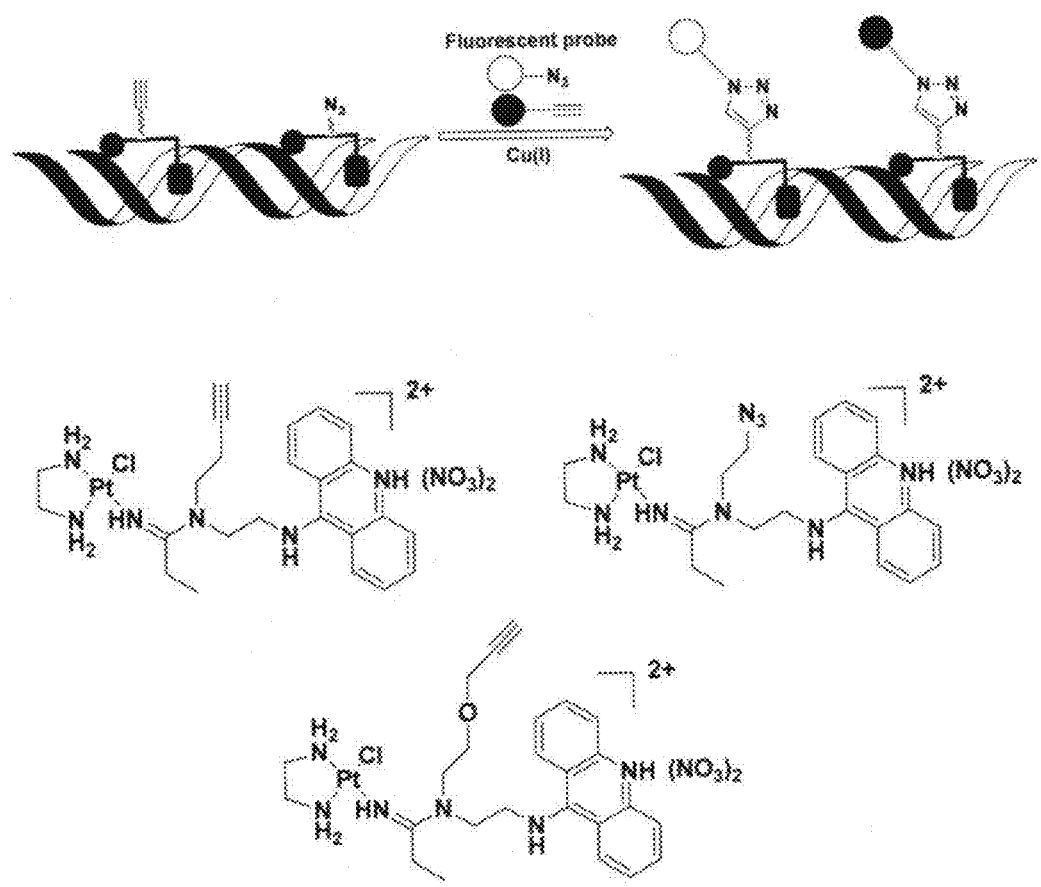
FIGS. 14A and 14B show how one might be able to visualize the compounds of the present invention using fluorescent probes.

FIGS. 14A and 14B show how one might be able to visualize the compounds of the present invention using fluorescent probes. FIG. 14A shows click activated chemistry of a 3+2 cycloaddition reaction wherein an alkyne group on the warhead compound (as shown by two of the compounds in FIG. 14B) reacts with an azide group that is attached to a fluorescent moiety to generate the 1,2,3 triazole 4-yl containing compound with the fluorescent probe. Alternatively, an azide group on the warhead compound (as shown by one of the compounds in 14B), which is attached to DNA (as shown in 14A) reacts with an alkyne-containing compound that has a fluorescent moiety attached to it to generate a 1,2,3-triazole-1-yl compound that still has the fluorescent moiety attached to it. A column or some other purification means might be used to isolate DNA, and the attached fluorescent probe containing the triazole containing compound will allow vizualization of the warhead compound as it is attached to DNA. This can potentially be used to quantitate the amount of warhead compound that is attached to DNA as unattached fluorescent compounds can be separated from that which is attached to DNA.

Figure 15:
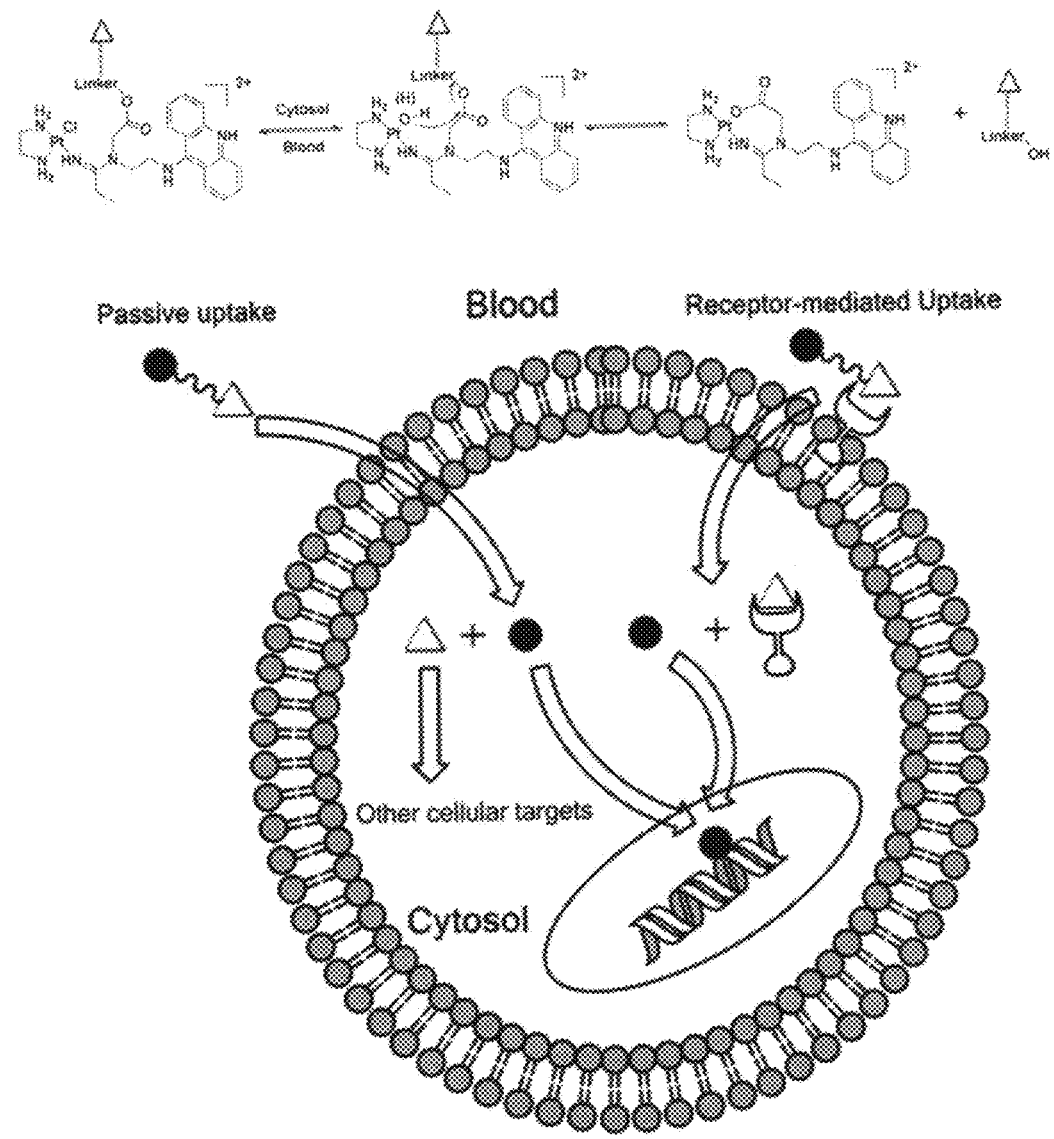
FIG. 15 shows a platinum (Lewis acid)-catalyzed release mechanism by which the platinum-amidine warhead is able to detach from the caged group (e.g., a targeting moiety or a synergistically acting agent with different pharmacological mechanism) in response to the low concentration of chloride ions in the cytosol. The Pt complex in an embodiment, is stable enough to persist in its intact form (chloride form) in circulation due to the high concentration of NaCl (~150 mM) in the blood. After entering the low-chloride environment of the cytosol (~3-5 mM), the platinum moiety rapidly transforms to the aquated ($H_2O$) form. Platinum-bound water is a strong nucleophile that is able to hydrolyze the ester under physiological conditions (pH 6-8, 37° C.), which releases the warhead from the targeting moiety (e.g., the linker) and allows it to bind with DNA to form cytotoxic adducts. This chloride-sensitive and enzyme-independent release mechanism can be used in the design of multifunctional platinum-acridine conjugates, such as targeted warhead and combination therapies.
Figure 16:
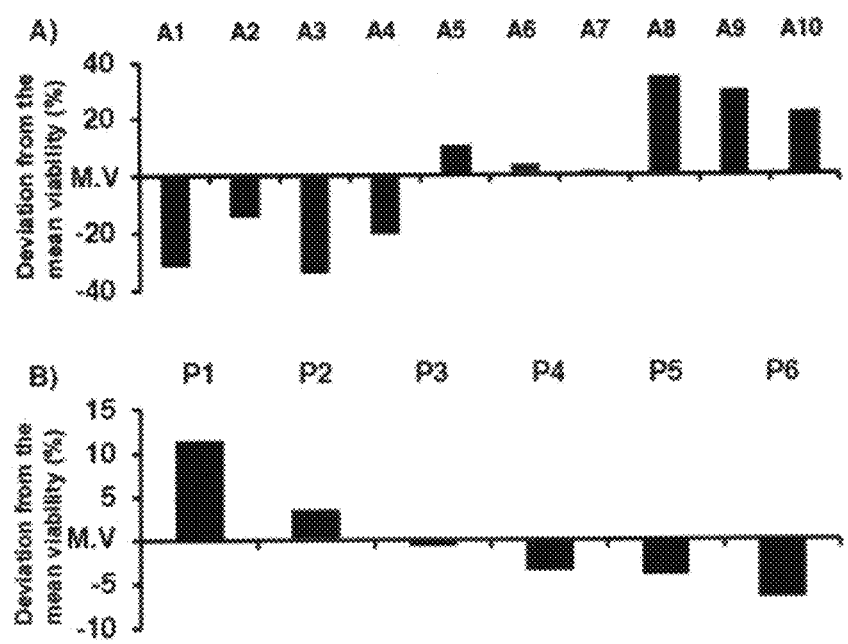
FIG. 16 shows the relative potencies of acridine (A) and platinum (B) fragments as building blocks in hybrid agents expressed as ±% deviations from the mean cell viability (M.V.) determined across the entire set of 60 library members.
Figure 17:
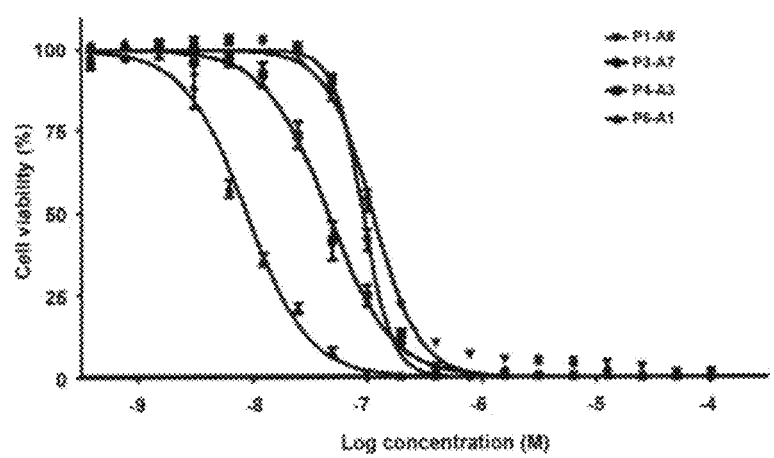
FIG. 17 shows the drug-response curves for cell proliferation assays in NCI-H460 cells treated with selected compounds. Error bars indicate ±standard deviations from the mean for two independent experiments performed in triplicate.
Figure 18:
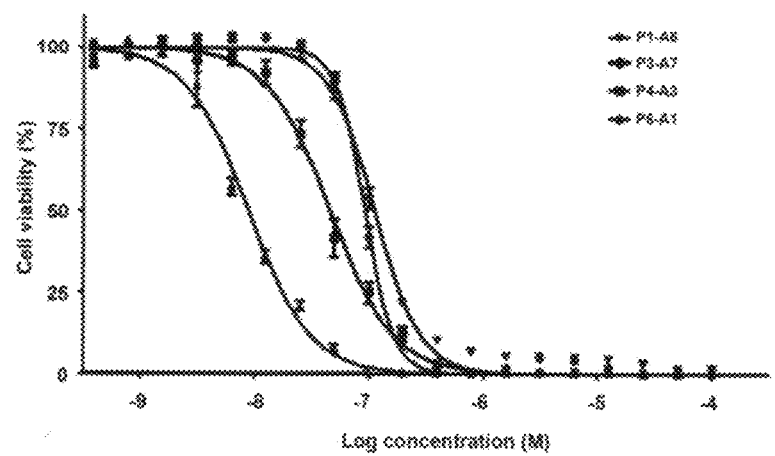
FIG. 18 shows the drug-response curves for cell proliferation assays in NCI-H460 cells treated with P3-A7 and the corresponding acridine ligand A7. Error bars indicate ±standard deviations from the mean for two independent experiments performed in triplicate.

FIG. 15 shows a platinum (Lewis acid)-catalyzed release mechanism by which the platinum-amidine warhead is able to detach from the caged group (e.g., a targeting moiety or a synergistically acting agent with different pharmacological mechanism) in response to the low concentration of chloride ions in the cytosol. The Pt complex, in an embodiment, is stable enough to persist in its intact form (chloride form) in circulation due to the high concentration of NaCl (~150 mM) in the blood. After entering the low-chloride environment of the cytosol (~3-5 mM), the platinum moiety rapidly transforms to the aquated ($H_2O$) form. Platinum-bound water is a strong nucleophile that is able to hydrolyze the ester under physiological conditions (pH 6-8, 37° C.), which releases the warhead from the targeting moiety (e.g., the linker) and allows it to bind with DNA to form cytotoxic adducts. This chloride-sensitive and enzyme-independent release mechanism can be used in the design of multifunctional platinum-acridine conjugates, such as targeted warhead and combination therapies.

SYNTHESIS AND CHARACTERIZATION OF EXAMPLES

The synthetic procedure to make exemplary compounds of the present invention (compounds 14b and 14a) are shown below in scheme 11 and are described in further detail below.

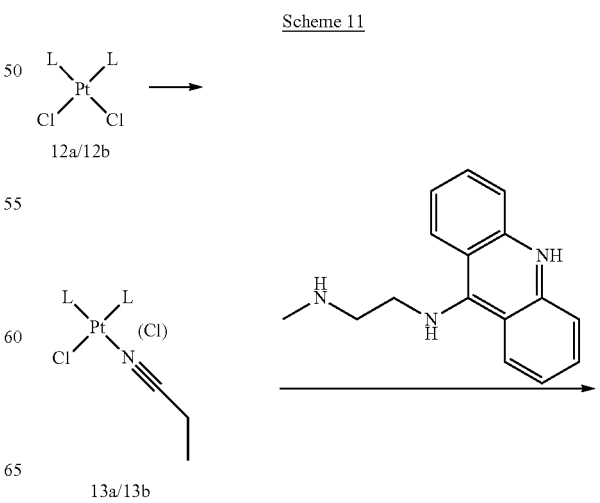

Scheme 11

31

-continued

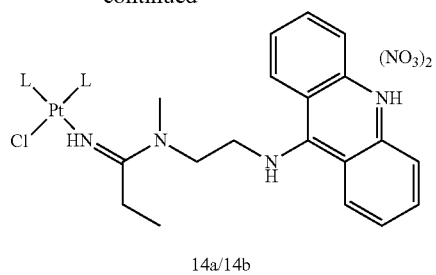

14a/14b a: L2 = en; b = NH$_3$

32

-continued

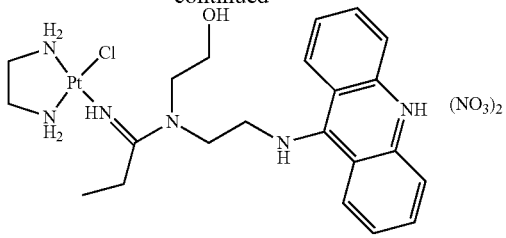

9-2

Note that the acridine moiety that appears above the arrow in scheme 11 has a methyl functionality attached to the amino group that is not adjacent to the acridine ring structure (i.e., the nitrogen that is four atoms away from the acridine ring). It is contemplated that this methyl group may contain a reactive functionality attached directly or indirectly to the methyl group such as a hydroxyl, an azide functionality, an amino, a cyano, a carboxylic acid or some other functionality that is more reactive than the methyl group (see the similar means of generated similar compounds in schemes 1-8). Note that if this reactive functionality is present, it may have to be protected so that the reaction that generates compounds 14a/14b proceeds as shown. The reactive functionality can then be de-protected and it can be used as a reactive functionality to join another moiety (such as compound W as described supra). Moreover, the ligands (i.e., the Ls that are on compounds 12a/12b and 13a/13b) may also possess reactive functionalities that can be used to join other moieties (such as compound W). These ligands may also have to undergo protection/deprotection to generate the compounds of the present invention.

Schemes 12 and 13 exemplify some reactions showing how the platinum containing moiety can be linked to the acridine moiety with hydroxyl or carboxylic acid linker moieties (corresponding to R$_{12}$ in many of the above schemes/compounds).

Scheme 12

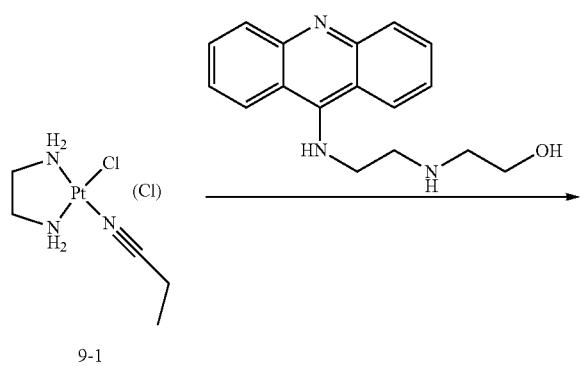

9-1

Scheme 13

10-1

10-2

Synthesis of Platinum-Acridine Complex 9-2 (from Scheme 12). Precursor complex 13a (170 mg, 0.45 mmol) from scheme 11 was converted to its nitrate salt by reaction with AgNO$_3$ (75 mg, 0.44 mmol) in 10 mL of anhydrous DMF. AgCl was filtered off, and the filtrate was cooled to −10° C. 2-((2-(Acridin-9-ylamino)ethyl)amino)ethanol (2-2, n=1, m=1) (132 mg, 0.47 mmol) was added to the solution, and the suspension was stirred until it turned into an orange-red solution (~7 h). The reaction mixture was added dropwise into 200 mL of cold ethyl ether, and the resulting yellow slurry was vigorously stirred for 30 min. The precipitate was recovered by membrane filtration, dried in a vacuum overnight, and re-dissolved in 40 mL of methanol containing 1 mol equivalent of HNO$_3$. After removal of the solvent by rotary evaporation, the crude product was recrystallized from hot ethanol, affording 14a as a microcrystalline solid. Yield 185 mg (54%). $^1$H NMR (DMF-d$_7$) δ 13.93 (1H, s), 9.97 (1H, s), 8.74 (2H, d, J=8.6 Hz), 8.03 (4H, overl m), 7.67 (2H, t, J=6.8 Hz), 6.55 (1H, s), 5.88 (2H, s), 5.57 (2H, s), 5.22 (1H, s), 4.55 (2H, s), 4.14 (21H, s), 3.68 (41-1, d), 3.14 (2H, s), 2.75 (6H, s), 1.38 (3H, s) Anal. (C$_{22}$H$_{31}$ClN$_7$O$_7$Pt.2H$_2$O) C, H, N.

Synthesis of Platinum-Acridine Complex 10-2 (from Scheme 13): This analogue was prepared as described for 9-2 with minor modification. Briefly, precursor complex 13a (170 mg, 0.45 mmol) from scheme 11 was converted to its nitrate salt by reaction with AgNO$_3$ (75 mg, 0.44 mmol) in 10 mL of anhydrous DMF. AgCl was filtered off, and the filtrate was cooled to −10° C. 2-((2-(acridin-9-ylamino)ethyl)amino) ethanol (4-4, n=1, m=1) (132 mg, 0.45 mmol) and TEA (91 mg, 0.9 mmol) was added to the solution, and the suspension was stirred during which yellow precipitation formed (~12 h). The precipitate was recovered by membrane filtration, recrystallized from hot ethanol and dried in a vacuum overnight affording 10-2 as a yellow solid (201 mg, 71%). $^1$H NMR (D$_2$O) δ 7.93 (2H, d, J=8.62 Hz), 7.72 (2H, t, J=7.73 Hz), 7.35 (4H, overl m), 4.02 (2H, t, J=4.8 Hz), 3.82 (2H, s), 3.68 (4H, s), 2.54 (6H, m), 0.74 (3H, s).

Synthesis and Product Characterization. $^1$H NMR spectra of the target compounds and intermediates were recorded on Bruker Advance 300 and DRX-500 instruments operating at 500 and 300 MHz, respectively. $^{13}$C NMR spectra were recorded on a Bruker Advance 300 instrument operating at 75.5 MHz. Chemical shifts (δ) are given in parts per million (ppm) relative to internal standards trimethylsilane (TMS), or 3-(trimethylsilyl)-1-propanesulfonic acid sodium salt (DSS) for samples in D$_2$O. $^{195}$Pt NMR spectra were recorded on a Bruker DRX-500 MHz spectrometer at 107.5 MHz. Aqueous K$_2$[PtCl$_4$] was used as an external standard, and $^{195}$Pt chemical shifts are reported vs [PtCl$_6$]$^{2-}$. The target compounds (Example 1 and Example 2) were fully characterized by gradient COSY and $^1$H-detected gradient HMQC and HMBC spectra recorded on a Bruker DRX-500 MHz spectrometer. Elemental analyses were performed by Quantitative Technologies Inc., Madison, N.J. All reagents were used as obtained from commercial sources without further purification unless indicated otherwise. Solvents were dried and distilled prior to use.

Synthesis of Complex 13a (from Scheme 11). The complex [PtCl$_2$(en)] (200 mg, 0.613 mmol) was heated under reflux in dilute HCl (pH 4) with propionitrile (2.7 mL, excess) until the yellow suspension turned into a colorless solution (~2 h). Solvent was removed by rotary evaporation, and the pale yellow residue was dissolved in 7 mL of dry methanol. The solution was passed through a syringe filter, and the colorless filtrate was added directly into 140 mL of vigorously stirred dry diethyl ether, affording 13a as an off-white microcrystalline precipitate, which was filtered off and dried in a vacuum. Yield 210 mg (90%). $^1$H NMR (D$_2$O) δ 2.88 (2H, q, J=7.5 Hz), 2.64 (4H, m), 1.30 (3H, t, J=7.5 Hz). $^{13}$C-{H} NMR (D$_2$O) δ 122.9, 48.7, 48.4, 12.3, 9.2. $^{195}$Pt NMR (D$_2$O) δ −2711. Anal. (C$_5$H$_{13}$Cl$_2$N$_3$Pt) C, H, N.

Synthesis of Complex 13b (from Scheme 11). This precursor was synthesized analogously to 13a starting from [PtCl$_2$(NH$_3$)$_2$] (300 mg, 1 mmol) and propionitrile (4.2 mL). Yield: 295 mg (83%). $^1$H NMR (D$_2$O) δ 2.89 (2H, q, J=7.5 Hz), 1.31 (3H, t, J=7.5 Hz). $^{13}$C-{H} NMR (D$_2$O) δ 121.9, 12.3, 9.2. $^{195}$Pt NMR (D$_2$O) δ −2467. Anal. (C$_3$H$_{11}$Cl$_2$N$_3$Pt) C, H, N.

Complexes 13' and 14' (isotopically enriched 13a and 14a) containing $^{15}$N-en were synthesized accordingly starting from [PtCl$_2$($^{15}$N-en)]. 13a': $^1$H NMR (MeOH-d$_4$): δ 6.11 and 5.86 (2H, d of t, NH$_2$ trans to Cl, $^1$J($^1$H-$^{15}$N)=75 Hz, $^3$J($^1$H-$^1$H)=5.3 Hz), 6.01 and 5.76 (2H, d of t, NH$_2$ trans to N, $^1$J($^1$H-$^{15}$N)=75 Hz, $^3$J($^1$H-$^1$H)=5.2 Hz), 2.93 (2H, q, J=7.6 Hz), 2.57 (4H, m), 1.33 (3H, t, J=7.5 Hz). 14a': $^1$H NMR (DMF-d$_7$) δ 13.92 (1H, s), 9.90 (1H, s), 8.70 (2H, d, J=8.6 Hz), 8.07 (4H, m, overlap), 7.63 (2H, t, J=6.8 Hz), 6.26 (NH, 1H, s), 5.82 and 5.53 (2H, d of t, NH$_2$ trans to Cl, $^1$J($^1$H-$^{15}$N)=74.5 Hz, $^3$J($^1$H-$^1$H)=5.0 Hz and 5.1 Hz), 5.47 (2H, d of t, NH$_2$ trans to N, $^1$J($^1$H-$^{15}$N)=75 Hz, $^3$J($^1$H-$^1$H)=5.1 Hz), 4.51 (2H, t, J=6.3 Hz), 4.10 (2H, t, J=6.7 Hz), 3.21 (3H, s), 3.12 (2H, q, J=7.4 Hz), 2.68 (4H, s), 1.33 (3H, t, J=7.5 Hz).

Synthesis of Complex 14a (from Scheme 11). Precursor complex 13a (170 mg, 0.45 mmol) was converted to its nitrate salt by reaction with AgNO$_3$ (75 mg, 0.44 mmol) in 10 mL of anhydrous DMF. AgCl was filtered off, and the filtrate was cooled to −10° C. N-(acridin-9-yl)-N'-methylethane-1,2-diamine (117 mg, 0.47 mmol) was added to the solution, and the suspension was stirred until it turned into an orange-red solution (~7 h). The reaction mixture was added dropwise into 200 mL of cold dichloromethane, and the resulting yellow slurry was vigorously stirred for 30 min. The precipitate was recovered by membrane filtration, dried in a vacuum overnight, and dissolved in 40 mL of methanol containing 1 mol equiv of HNO$_3$. After removal of the solvent by rotary evaporation, the crude product was recrystallized from hot ethanol, affording 14a as a microcrystalline solid. Yield 169 mg (52%). $^1$H NMR (DMF-d$_7$) δ 13.92 (1H, s), 9.90 (1H, s), 8.70 (2H, d, J=8.6 Hz), 8.07 (4H, overl m), 7.63 (2H, t, J=6.8 Hz), 5.78 (2H, s), 5.48 (2H, s), 4.51 2H, t, J=6.3 Hz), 4.10 (2H, t, J=6.7 Hz), 3.21 (3H, s), 3.12 (2H, q, J=7.4 Hz), 2.68 (4H, s), 1.33 (3H, t, J=7.5 Hz). $^{13}$C-{H} NMR (DMF-d$_7$) δ 170.4, 159.0, 140.6, 135.7, 128.2, 124.3, 119.4, 113.5, 50.1, 49.4, 49.2, 47.5, 28.0, 11.4. $^{195}$Pt NMR (DMF-d$_7$) δ −2494. UV/Vis (H$_2$O): λ$_{max}$ 413, ϵ=10571. Anal. (C$_{21}$H$_{31}$ClN$_8$O$_6$Pt.H$_2$O) C, H, N.

Synthesis of Complex 14b (from Scheme 11): This analogue was prepared as described for 14a starting from 293 mg (0.83 mmol) of 13b, 132 mg (0.79 mmol) of AgNO$_3$, and 197 mg (0.79 mmol) of N-(acridin-9-yl)-N'-methylethane-1,2-diamine. Yield: 315 mg (57%). $^1$H NMR (DMF-d$_7$) δ 13.93 (1H, s), 9.92 (1H, s), 8.68 (2H, d, J=8.6 Hz), 8.03 (4H, overl m), 7.62 (t, J=7.2 Hz), 6.27 (1H, s), 4.53 (3H, s), 4.49 (2H, t, J=6.8 Hz), 4.16 (3H, s), 4.10 (2H, t, J=6.3 Hz), 3.20 (3H, s), 3.15 (2H, q, J=7.6 Hz), 1.33 (3H, t, J=7.5 Hz). $^{13}$C-{H} NMR (DMF-d$_7$) δ 170.3, 159.3, 140.8, 135.9, 126.5, 124.5, 119.6, 113.6, 50.8, 47.8, 28.3, 11.5. $^{195}$Pt NMR (DMF-d$_7$) δ −2264. UV/Vis (H$_2$O): λ$_{max}$ 413, ϵ=9224. Anal. (C$_{19}$H$_{29}$ClN$_8$O$_6$Pt.2.5H$_2$O) C, H, N.

Synthesis of tert-butyl(2-(prop-2-yn-1-ylamino) ethyl)carbamate (1-2; n,m=1, Scheme 1)

A mixture of tert-butyl(2-aminoethyl)carbamate (1-1, 1.5 eq) and 3-chloroprop-1-yne (1 eq) in 30 mL of dry THF was refluxed for 24 h. The solvent was evaporated off and the residue was purified by flash chromatography to afford 1-2 as a colorless oil. (Yield: 62%). $^1$H NMR (D$_2$O) δ 4.07 (2H, d, J=2.5 Hz), 3.58 (2H, t, J=6.7 Hz), 3.46 (2H, t, J=6.7 Hz), 3.10 (1H, t, J=2.4 Hz).

Synthesis of N$^1$-(prop-2-yn-1-yl)ethane-1,2-diamine (1-3; n,m=1, Scheme 1)

Compound 1-2 (1.98 g, 0.01 mol) was dissolved in 40 mL of a 1:1 mixture of 4 M HCl and MeOH. The mixture was stirred at 0° C. for 2 h. The solvent was evaporated off to afford 1.67 g of the product as a white solid (Yield: 98%). $^1$H NMR (CDCl$_3$) δ 3.37 (2H, d, J=2.4 Hz), 3.18 (2H, t, J=5.7 Hz), 2.77 (2H, t, J=5.7 Hz), 2.17 (1H, d, J=2.4 Hz), 1.39 (9H, s)

Synthesis of N$^1$-(acridin-9-yl)-N$^2$-(prop-2-yn-1-yl) ethane-1,2-diamine (1-4; n,m=1, Scheme 1)

A mixture of phenoxyacridine (1.35 g, 0.005 mol), 1-3 (0.94 g, 0.0055 mol) and triethylamine (TEA) (2.52 g, 0.025 mol) in 20 mL of dry THF was refluxed for 24 h. The solvent was evaporated off and the residue was dissolved in 30 mL of ethanol. To this solution were added 5 mL of concentrated HCl and the mixture was stored at 4° C. for 12 h. A yellow precipitate formed which was recovered by filtration, re-suspended in 50 mL of 2 M ammonium hydroxide, and stirred at room temperature for 30 min. The aqueous phase was extracted with CH$_2$Cl$_2$ and the organic phase was collected, dried over Na$_2$SO$_4$, and concentrated using rotary evaporation, affording 2.4 g of the free base as an orange oil (Yield: 87%). $^1$H NMR (CDCl$_3$) δ 3.37 (2H, d, J=2.4 Hz), 3.18 (2H, t, J=5.7 Hz), 2.77 (2H, t, J=5.7 Hz), 2.17 (1H, d, J=2.4 Hz), 1.39 (9H, s)

Synthesis of 2-((2-(acridin-9-ylamino)ethyl)amino) ethanol (2-2; n,m=1, Scheme 2)

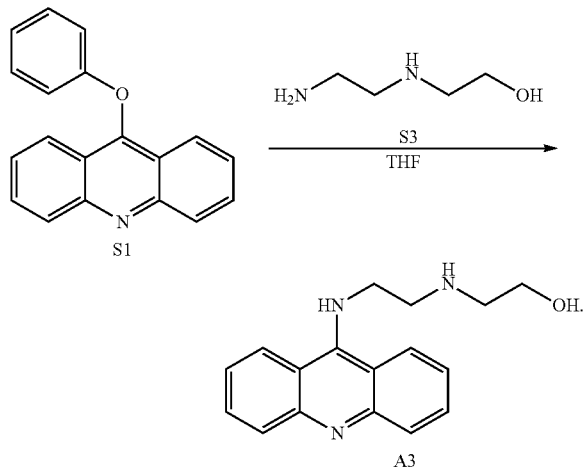

A mixture of phenoxyacridine (S1) (2.71 g, 0.01 mol) and 2-(2-aminoethylamino)ethanol (S3)

(1.14 g, 0.011 mol) in 15 mL of anhydrous THF was refluxed for 16 h. The solvent was evaporated off and the residue was dissolved in 30 mL of acetone. To this solution were added 5 mL of concentrated HCl and the mixture was stirred at 4° C. for 3 hours. A yellow precipitate formed which was recovered by filtration, re-suspended in 50 mL of 2 M ammonium hydroxide, and stirred at room temperature for 30 min. The aqueous phase was extracted with CH$_2$Cl$_2$ and the organic phase was collected, dried over Na$_2$SO$_4$, and concentrated using rotary evaporation, affording 2.57 g of the free base as an yellow solid (Yield: 92%). This derivative was synthesized in complete analogy to compound 1-4. The procedure afforded 2.3 g of the free base as an orange oil (Yield: 82%). $^1$H NMR (d-DMSO) δ 8.32 (1H, s), 8.29 (2H, d, J=8.5 Hz), 7.69 (2H, s), 7.59 (2H, t, J=7.3 Hz), 7.28 (2H, t, J=7.2 Hz), 4.53 (1H, s), 3.87 (2H, t, J=6.19 Hz), 3.47 (2H, 1, J=5.7 Hz), 2.91 (2H, t, J=6.15 Hz), 2.64 (2H, t, J=5.70 Hz).

Synthesis of N$^1$-(acridin-9-yl)-N$^2$-(2-azidoethyl) ethane-1,2-diamine (3-4; n,m=1, Scheme 3)

N$^1$-(2-Azidoethyl)ethane-1,2-diamine (3-3) was synthesized according to the method described by Carboni. A mixture of phenoxyacridine (1.35 g, 0.005 mol) and 3-3 (0.71 g, 0.0055 mol) was then refluxed in 20 mL of dry THF for 36 h. The solvent was evaporated off and the residue was dissolved in 30 mL ethanol, 5 mL of concentrated HCl were added, and the mixture was stored in the refrigerator overnight for crystallization to afford the corresponding hydrochloride salt. The yellow solid was recovered by filtration, suspended in 50 mL of 2M ammonium hydroxide and stirred at room temperature for 30 min. The mixture was extracted with CH$_2$Cl$_2$ and the organic phase was collected, dried by Na$_2$SO$_4$, and concentrated by rotary evaporation, affording 2.5 g of the free base as an orange oil (Yield: 84%). $^1$H NMR (CDCl$_3$) δ 8.20 (2H, d, J=8.1 Hz), 7.93 (2H, t, J=7.5 Hz), 7.62 (2H, d, J=8.6 Hz), 7.57 (2H, t, J=7.7 Hz), 4.43 (2H, t, J=6.2 Hz), 3.77 (2H, 1, J=5.5 Hz), 3.63 (2H, t, J=6.1 Hz), 3.31 (2H, t, J=5.5 Hz).

Synthesis of Precursor A2

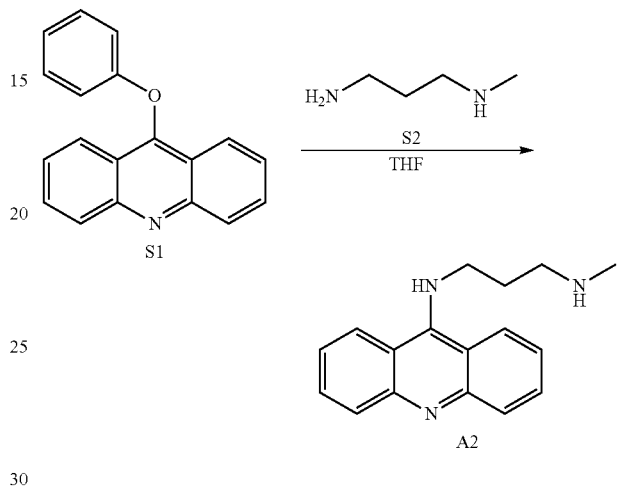

A2 was prepared using the procedure described for A3 above. Yield: 94%. $^1$H NMR (300 MHz, CDCl$_3$) δ 8.12 (d, J=8.7, 2H), 8.02 (d, J=8.7, 2H), 7.61 (t, J=6.7 Hz, 2H), 7.25 (t, J=7.5, 2H), 4.01 (t, J=5.9 Hz, 2H), 2.96-2.75 (m, 2H), 2.53 (s, 3H), 1.94-1.68 (p, J=5.9 Hz, 2H). MS (ESI, positive-ion mode): calculated for C$_{17}$H$_{20}$N$_3$ ([M+H]+), 266.36. found: 266.2.

Synthesis of Precursor A4

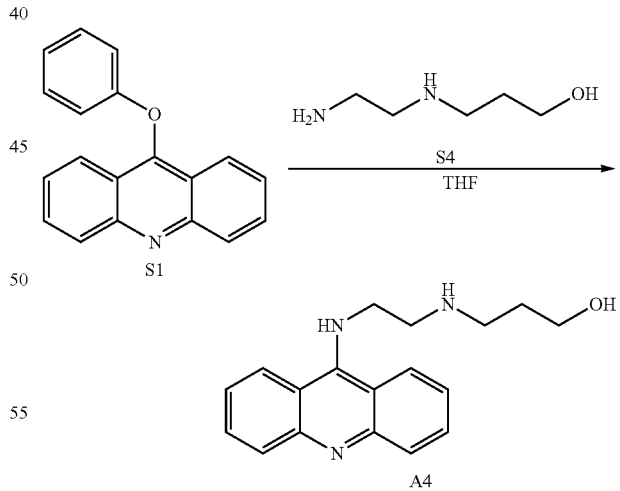

A4 was prepared using the procedure described for A3 above. Yield: 86%. $^1$H NMR (CDCl$_3$) δ 8.11 (d, J==8.5 Hz, 2H), 8.02 (d, J=8.6 Hz, 2H), 7.72-7.54 (m, 2H), 7.35-7.29 (m, 2H), 3.87-3.82 (m, 4H), 3.16-2.64 (m, 4H), 1.79 (p, J=6.5 Hz, 2H). $_{13}$C-NMR (CDCl$_3$) 151.97, 147.93, 130.25, 127.65, 123.25, 122.70, 116.33, 62.15, 49.48, 48.91, 47.68, 31.98. MS (ESI, positive-ion mode): calculated for C$_{18}$H$_{22}$N$_3$O ([M+H]+), 296.38. found: 296.3.

Synthesis of Precursor A5

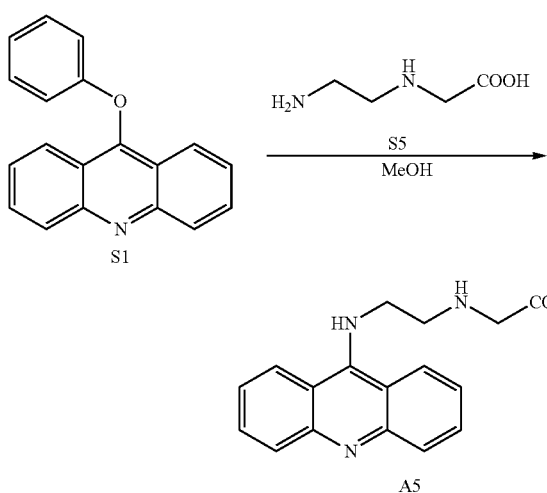

A mixture of phenoxyacridine (S1) (2.71 g, 0.01 mol) and 2-((2-aminoethyl)glycine (S5) (1.3 g, 0.011 mol) in 20 mL of dry MeOH was refluxed for 3 h. The yellow solid that precipitated during the reaction was collected by filtration, washed with hot THF and ether, and dried in a vacuum, affording 2.55 g of the product as a yellow solid (Yield: 86%). $^1$H NMR ((CD$_3$)$_2$SO) 8.22 (m, 2H), 7.55 (t, J=7.6 Hz, 2H), 7.43 (m, 2H), 7.15 (t, J=7.6 Hz, 2H), 4.08 (d, J=6.0 Hz, 2H), 3.22 (s, 2H), 3.16 (t, J=5.9 Hz, 2H). A $_{13}$C NMR spectrum of this compound was not obtained due to limited solubility of the compound. MS (ESI, positive-ion mode): calculated for C$_{17}$H$_{18}$N$_3$O$_2$([M+H]+), 296.34; found: 296.3.

Synthesis of Precursor A6

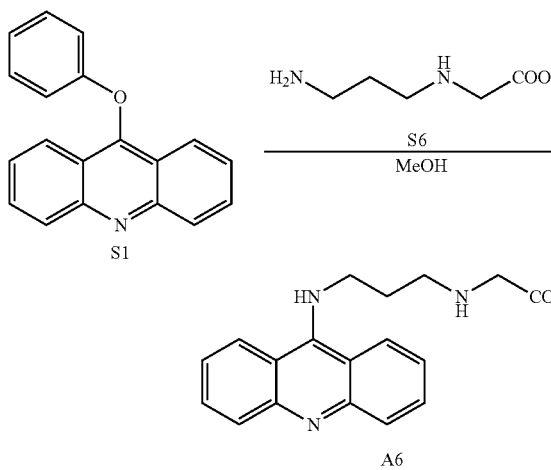

A6 was prepared using the procedure described for A5. Yield: 91%. $^1$H NMR ((CD$_3$)$_2$SO) δ 8.21 (d, J=8.4 Hz, 2H), 7.54 (m, 3H), 7.12-7.18 (m, 4H), 6.93-6.62 (m, 2H), 3.91 (t, J=6.4 Hz, 2H), 3.21 (s, 2H), 3.01 (t, J=7.2 Hz, 2H), 2.03 (p, J=6.5 Hz, 2H). $_{13}$C NMR ((CD$_3$)$_2$SO) δ 166.95, 157.31, 152.15, 130.13, 129.21, 125.84, 120.79, 118.56, 115.13, 49.87, 48.74, 45.42, 27.92. MS (ESI, positive-ion mode): calculated for C$_{18}$H$_{20}$N$_3$O$_2$ ([M+H]+), 310.37; found: 310.2.

Synthesis of Precursor A7

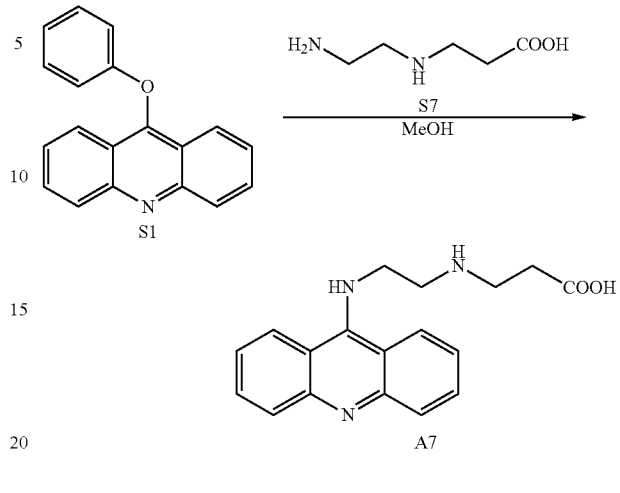

A7 was prepared using the procedure described for A5. Yield: 84%. $^1$H NMR (D$_2$O) δ 8.04 (d, J=8.7 Hz, 2H), 7.83 (dd, J=8.4, 7.0 Hz, 2H), 7.58-7.34 (m, 4H), 4.33 (t, J=6.1 Hz, 2H), 3.60 (t, J=5.8 Hz, 1H), 3.33 (t, J=6.3 Hz, 2H), 3.33 (t, J=6.3 Hz, 2H). $_{13}$C NMR (D$_2$O) δ 166.95, 157.31, 152.15, 130.13, 129.21, 125.84, 118.56, 115.13, 49.87, 48.80, 45.42, 27.92. MS (ESI, positive-ion mode): calculated for C$_{18}$H$_{20}$N$_3$O$_2$ ([M+H]+), 310.37; found: 310.3.

Synthesis of Precursor A8

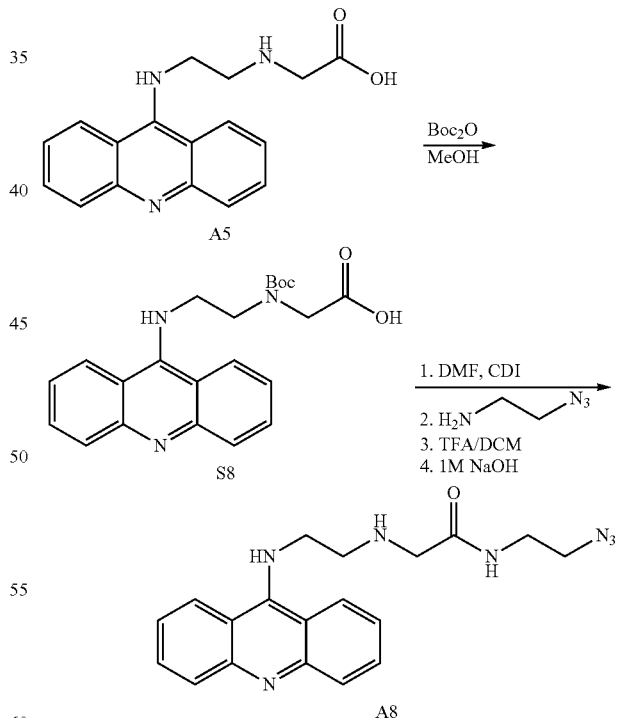

The Boc-protected acridine derivative (S8) (1.36 g, 4.6 mmol) was synthesized as follows. A5 was suspended in 30 mL of anhydrous methanol, to which was added Boc$_2$O (1.3 g, 6 mmol) in 5 mL of anhydrous MeOH at 0-5° C. maintained with an ice bath. The mixture was then stirred at room temperature for 4 h. The solvent was removed by rotary evaporation and residue was dissolved in 10 mL of dichloromethane and precipitated with 200 mL of anhydrous diethyl ether. The solid was recovered by filtration and dried in a vacuum affording 1.79 g (99%) of the product as a yellow solid, which was used in the next step without further purification. Compound S8 (1 g, 2.52 mmol) and 1,1'-carbonyldiimidazole (CDI, 533 mg, 3.28 mmol) were combined in 20 mL of anhydrous DMF. The mixture was heated to 40-50° C. and stirred for 6 h. Then the solution was cooled to 0-5° C. in an ice bath and 264 mg of 2-azidoethanamine dissolved in 3 mL of anhydrous DMF were added. The mixture was stirred at 0-5° C. for 4 h. DMF was removed by vacuum distillation at 35-40° C., and the residue was redissolved in 40 mL of dichloromethane and washed with 1 M HCl (3×20 mL). The organic phase was collected, dried with anhydrous $Na_2SO_4$, and concentrated to afford an orange oil. To remove the Boc group, the residue was dissolved in 6 mL of a 1:1 mixture of anhydrous dichloromethane and trifluoroacetic acid and stirred at room temperature for 3 h. The reaction was quenched by adding 10 mL of 1 M NaOH solution. The crude product was extracted from NaOH solution with DCM, dried over anhydrous $Na_2SO_4$, and concentrated. The product was purified by flash chromatography ($Al_2O_3$, DCM:MeOH, 30:1). Yield: 0.59 g (64%). $^1$H NMR ($CDCl_3$) δ 8.10 (d, J=8.7 Hz, 2H), 7.97 (d, J=8.6 Hz, 2H), 7.60 (t, J=8.3, 6.8 Hz, 2H), 7.40-7.14 (m, 3H), 3.89 (t, J=5.6 Hz, 2H), 3.50-3.23 (m, 6H), 2.99 (t, J=5.6 Hz, 2H). $_{13}$C NMR ($CDCl_3$) δ172.56, 152.98, 146.04, 131.21, 125.75, 123.56, 122.97, 115.48, 50.72, 48.69, 48.47, 44.85, 38.82, 36.22. MS (ESI, positive-ion mode): calculated for $C_{19}H_{22}N_7O$ ([M+H]+), 364.42; found: 364.3.

Synthesis of Precursor A9

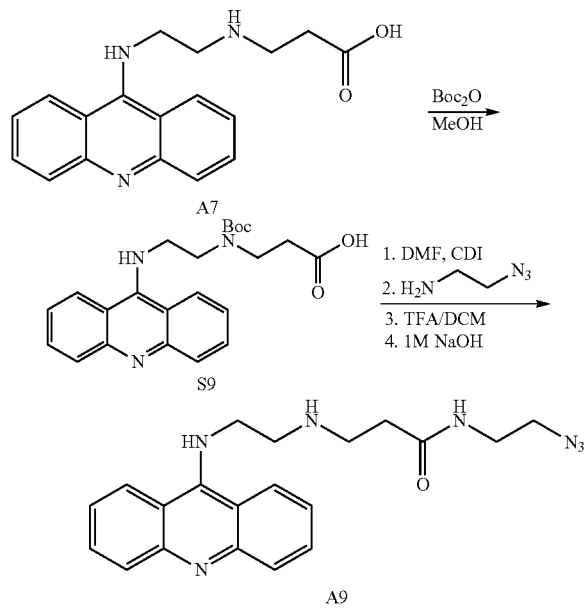

A9 was prepared using the procedure described for A8. Yield: 64%. $^1$H NMR ($CDCl_3$) δ 8.09 (d, J=8.7 Hz, 2H), 8.02 (d, J=8.7 Hz, 2H), 7.59 (t, J=7.6 Hz, 2H), 7.41 (s, 1H), 7.27 (t, J=7.5 Hz, 2H), 4.95 (brs, 2H), 3.92 (t, J=5.6 Hz, 2H), 3.44 (s, 4H), 2.91-3.14 (m, 4H), 2.53 (t, J=6.0 Hz, 2H). $_{13}$C NMR ($CDCl_3$) 152.09, 149.60, 129.65, 129.23, 123.60, 121.91, 115.75, 51.37, 51.32, 36.51, 29.15. MS (ESI, positive-ion mode): calculated for $C_{20}H_{24}N_7O$ ([M+H]+), 378.45; found: 378.3.

Synthesis of Precursor A10

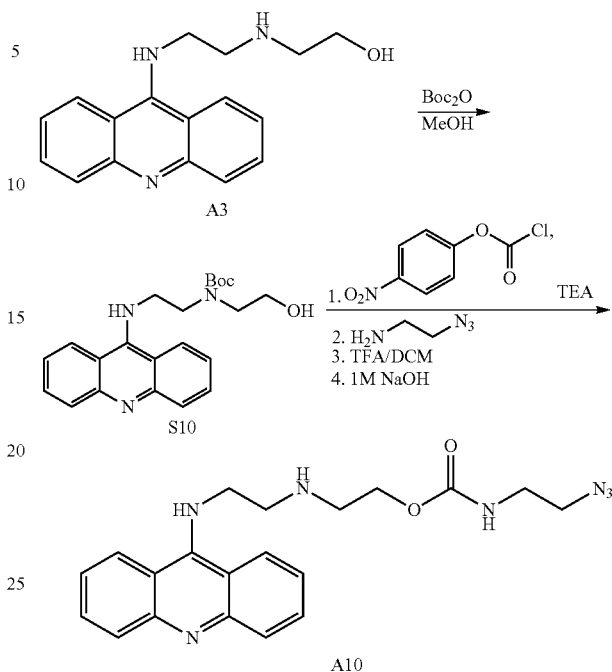

The Boc-protected acridine derivative (S10) was prepared as described for S8 starting with compound A3. Compound S10 (1 g, 2.62 mmol), TEA (793 mg, 7.85 mmol) and 4-nitrobenzyl chloroformate (732 mg, 3.4 mmol) were dissolved in 20 mL of anhydrous DCM. The mixture was stirred at room temperature for 16 h. Then 271 mg of 2-azidoethanamine dissolved in 5 mL of anhydrous DCM was added and the reaction was stirred for another 8 h. The solvent was removed using vacuum distillation and the residue was redissolved in 40 mL of DCM and washed with 1 M HCl (3×20 mL). The organic phase was collected, dried with anhydrous $Na_2SO_4$, and concentrated to afford an orange oil. To remove the Boc group, the orange oil was dissolved in 6 mL of a 1:1 mixture of anhydrous dichloromethane and trifluoroacetic acid and stirred at room temperature for 3 h. The reaction was quenched by adding 10 mL of 1 M NaOH solution. The crude product was extracted from NaOH solution with DCM, dried over anhydrous $Na_2SO_4$, and concentrated. The product was further purified by flash chromatography ($Al_2O_3$, DCM:MeOH, 30:1). Yield: 0.73 g (71%). $^1$H NMR ($CDCl_3$) δ 8.12-7.96 (m, 4H), 7.59 (t, J=7.8 Hz, 2H), 7.23 (t, J=7.6 Hz, 2H), 5.65 (brs, 1H), 4.27 (t, J=4.8 Hz, 2H), 3.92 (t, J=5.7 Hz, 1H), 3.61-3.20 (m, 4H), 3.01 (t, J=5.7 Hz, 2H), 2.96 (t, J=4.9 Hz, 2H). $_{13}$C NMR ($CDCl_3$) δ 156.53, 152.69, 145.93, 131.22, 125.98, 123.3, 123.00, 115.07, 64.48, 50.97, 48.35, 48.17, 47.83, 40.45. MS (ESI, positive-ion mode): calculated for $C_{20}H_{24}N_7O_2$ ([M+H]+), 394.45; found: 394.3.

Synthesis of Precursor P1

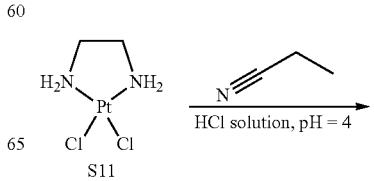

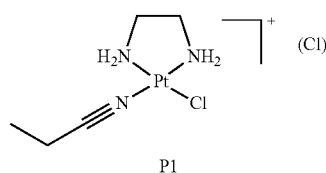

P1

The complex [PtCl$_2$(en)](S11) (0.50 g, 1.54 mmol) was heated under reflux in 25 mL of dilute HCl (pH 4) with propionitrile (6.85 mL, 98.5 mmol) until the yellow suspension turned into a colorless solution (~2 h). Solvent was removed by rotary evaporation, and the pale-yellow residue was redissolved in 10 mL of dry methanol. A small amount of an insoluble yellow solid was removed by membrane filtration and the colorless filtrate was added directly into 250 mL of vigorously stirred dry diethyl ether, affording Pt as an off-white, extremely hygroscopic microcrystalline precipitate. Yield: 0.48 g (83%). $^1$H NMR (D$_2$O) δ 5.72, 5.64 (2 br s, 0.7H, HD exchange), 2.87 (q, J=7.5 Hz, 2H), 2.48-2.75 (m, Pt satellites, 4H), 1.3 (t, J=7.5 Hz, 3H).

Synthesis of Precursor P2

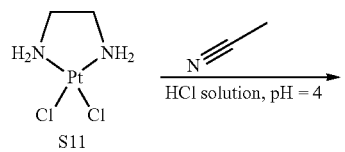

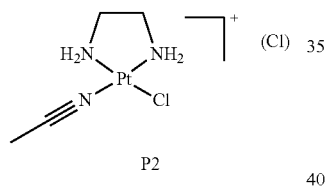

P2

P2 was prepared using the similar procedure as described for P1 as the white solid with the yield 89%. $^1$H NMR (D$_2$O) δ 5.80, 5.65 (2 brs, 1H, HD exchange), 2.87 (q, J=7.5 Hz, 2H), 2.55-2.65 (m, Pt satellites, 4H), 2.53 (s, 3H).

Synthesis of Precursor P3

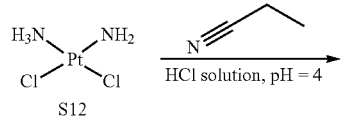

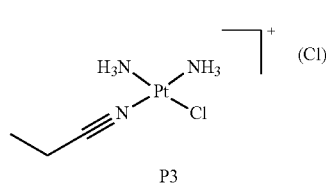

P3

P3 was prepared using the procedure described for P1. Yield: 74%. $^1$H NMR (D$_2$O) δ 2.89 (t, J=7.6, 2H), 1.30 (t, J=7.5, 3H).

Synthesis of Precursor P4

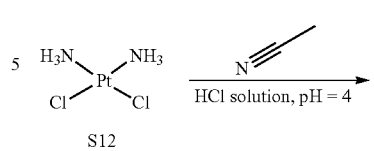

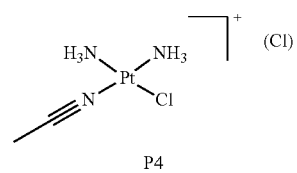

P4

P4 was prepared using the procedure described for P1. Yield: 63%. $^1$H NMR (D$_2$O) δ 2.53 (3H, m, Pt satellites), 4.35, 4.48 (4 H, HD exchange, 2 br s).

Synthesis of Precursor P5

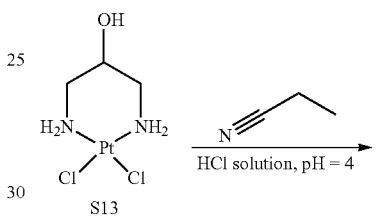

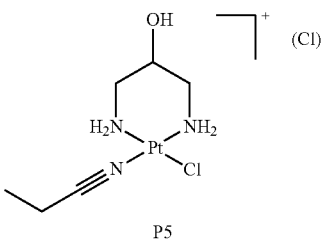

P5

P5 was prepared using the procedure described for P1. Yield: 91%. $^1$H NMR (D$_2$O) δ 4.26 (m, 1H), 2.99-2.54 (m, 6H), 1.39-0.96 (t, J=7.5 Hz, 3H).

Synthesis of Precursor P6

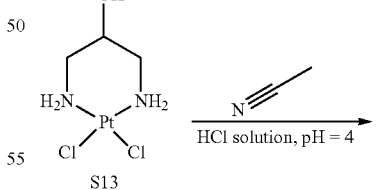

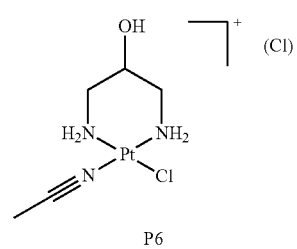

P6

P6 was prepared using the procedure described for P1. Yield: 77%. $^1$H NMR (D$_2$O) δ 4.28 (m, 1H), 2.85-2.53 (m, 4H), 2.53 (s, 3H).

Resynthesis of Compound P1-A3

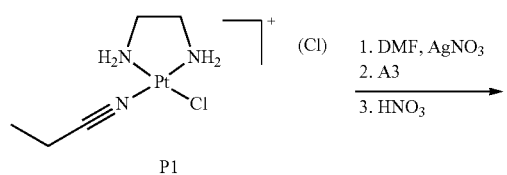

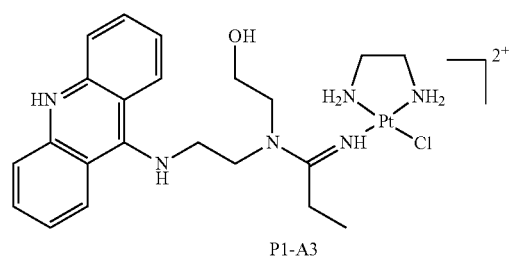

Platinum complex P1 (381 mg, 1 mmol) was converted to its nitrate salt by reaction with AgNO$_3$ (162 mg, 0.95 mmol) in 7 mL of anhydrous DMF. AgCl was removed by syringe filtration, and the filtrate was cooled to −10° C. Acridine precursor A3 (282 mg, 0.1 mmol) was added to the solution, and the suspension was stirred at −10° C. for 24 h. After treatment with activated carbon, the reaction mixture was added into 300 mL of stirred diethyl ether. The yellow precipitate was stirred for approximately 30 min and then recovered by membrane filtration and dried in a vacuum overnight. The solid was dissolved in anhydrous methanol containing 1 equivalent HNO$_3$, stirred at room temperature for 30 minutes and precipitated by 300 mL anhydrous diethyl ether. The product was further purified by recrystallization from hot ethanol to give 605.8 mg of the dinitrate salt as a yellow microcrystalline solid (Yield 82%). $^1$H NMR (MeOD) δ 8.42 (d, J=8.4 Hz, 2H), 7.88 (td, J=6.9, 1.2 Hz, 2H), 7.74 (d, J=8.4 Hz, 2H), 7.51 (td, J=7.2, 1.2 Hz, 2H 1H), 6.12 (brs, 1H), 5.32 (s, 2H), 5.11 (s, 2H), 4.32 (t, J=6.7 Hz, 2H), 3.89 (t, J=6.7 Hz, 2H), 3.63 (t, J=5.0 Hz, 2H), 3.47 (t, J=5.1 Hz, 2H), 2.94 (q, J=7.2 Hz, 1H), 2.47 (m, 4H), 1.18 (t, J=7.2 Hz, 3H). $_{13}$C NMR (MeOD) 171.73, 160.21, 141.38, 136.63, 126.48, 125.35, 119.73, 114.13, 60.70, 29.26, 11.85. MS (ESI, positive-ion mode): for C$_{22}$H$_{32}$ClN$_6$OPt ([M]+), 627.06; found: 627.3.

Resynthesis of Compound P4-A3.

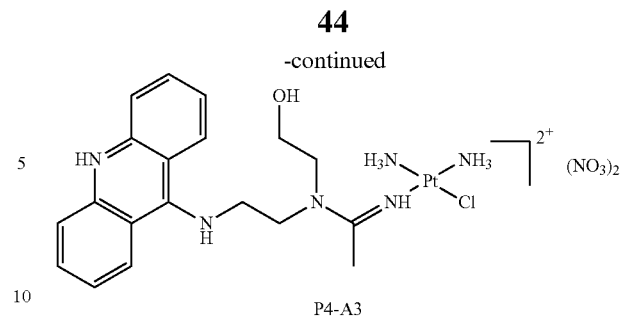

P4-A3 was prepared using the same procedure as described for P1-A3 and was recovered with a yield of 87%. $^1$H NMR (MeOD) δ 8.40 (d, J=8.8 Hz, 2H), 7.87 (t, J=6.8, 2H), 7.72 (dd, J=8.7, S12 1.2 Hz, 1H), 7.49 (d, J=8.4 Hz, 2H), 4.31 (t, J=7.0 Hz, 2H), 4.10 (brs, 2H), 3.91 (t, J=6.8 Hz, 1H), 3.75 (s, 2H), 3.65 (t, J=4.9 Hz, 2H), 3.49 (t, J=4.9 Hz, 2H), 2.58 (s, 3H). $_{13}$C NMR (MeOD) δ 167.49, 160.02, 141.40, 136.55, 126.49, 125.30, 119.77, 114.14, 60.73, 49.86, 48.16, 47.39, 23.02. MS (ESI, positive-ion mode): for C$_{19}$H$_{28}$ClN$_6$OPt ([M]+), 587.00; found: 585.2.

Resynthesis of Compound P6-A1.

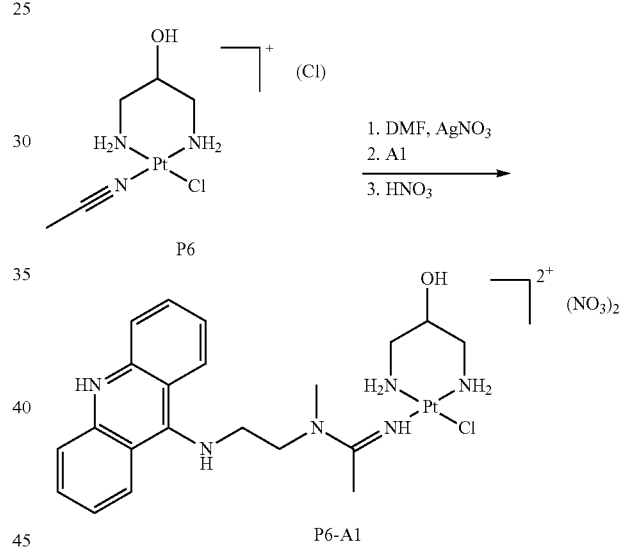

P6-A1 was prepared using the same procedure as described for P1-A3 and was recovered with a yield of 92%. $^1$H NMR (DMF-d7) δ 13.92 (s, 1H), 9.89 (s, 1H), 8.68 (d, J=8.7 Hz, 2H), 7.9-8.11 (m, 4H), 7.62 (td, J=6.4, 3.1 Hz, 2H), 6.21 (s, 1H), 5.65 (s, 1H), 5.60 (s, 1H), 5.13 (s, 2H), 4.87 (s, 1H), 4.50 (s, 2H), 4.12 (t, J=6.3 Hz 2H), 4.06 (s, 1H), 3.50 (s, 4H), 3.18 (s, 3H), 2.59-2.97 (m, 4H). $_{13}$C NMR (DMF) δ 165.94, 158.64, 139.96, 135.33, 125.29, 123.91, 118.98, 112.80, 65.84, 48.38, 47.80, 33.79, 28.66. MS (ESI, positive-ion mode): for C$_{21}$H$_{30}$ClN$_6$Opt ([M]+), 613.04; found: 612.3.

Resynthesis of Compound P1-A8.

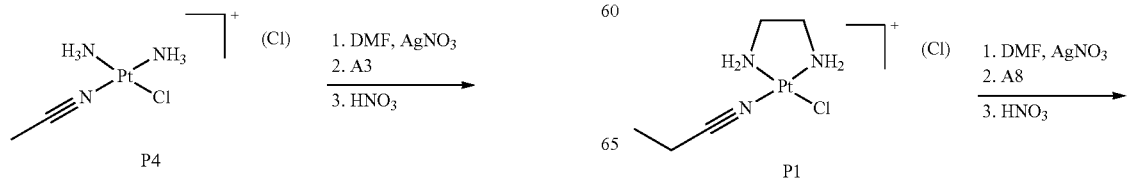

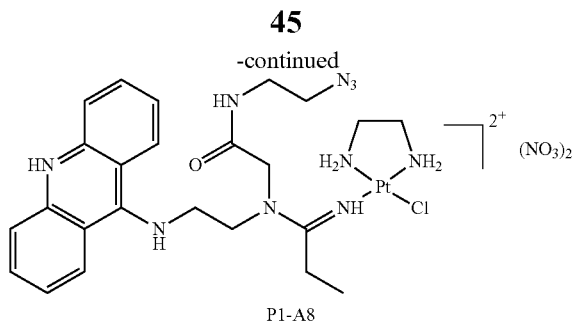

P1-A8

P1-A8 was prepared using the same procedure as described for P1-A3 and was recovered with a yield of 81%. $^1$H NMR (DMF-d7) δ 13.90 (s, 1H), 9.99 (s, 1H), 8.83-8.52 (m, 3H), 8.28-7.92 (m, 4H), 7.62 (td, J=6.6, 1.5 Hz 2H), 6.73 (s, 1H), 5.84 (s, 2H), 5.51 (s, 2H), 4.54 (q, J=5.7 Hz, 2H), 4.44 (s, 2H), 4.15 (t, J=5.9 Hz, 2H), 3.44-3.52 (m, 4H), 3.06 (q, J=7.9 Hz, 2H), 2.67 (s, 4H), 1.33 (t, J=7.5 Hz, 3H). $_{13}$C NMR (DMF-d7) δ 170.37, 169.56, 158.62, 140.17, 135.27, S13 125.92, 123.80, 118.90, 112.94, 50.32, 48.97, 48.79, 46.34, 38.78, 28.67, 11.00. MS (ESI, positive-ion mode): for $C_{24}H_{34}ClN_{10}OPt$ ([M]+), 709.13; found: 708.5.

Resynthesis of Compound P3-A7.

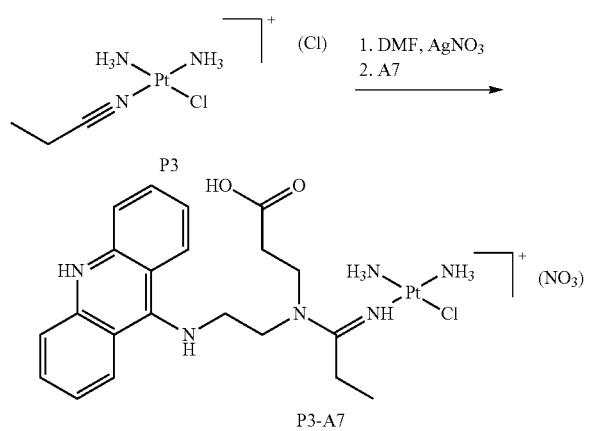

P3-A7

Platinum complex P3 (354 mg, 1 mmol) was converted to its nitrate salt by reaction with AgNO$_3$ (162 mg, 0.95 mmol) in 7 mL of anhydrous DMF. AgCl was removed by syringe filtration, and the filtrate was cooled to −10° C. Acridine precursor A7 (310 mg, 0.1 mmol) was added to the solution, and the suspension was stirred at 4° C. for 5 days. The mixture was poured into 300 mL of vigorously stirred diethyl ether, and the precipitate was recovered by membrane filtration and dried in a vacuum overnight. The product was further purified by recrystallization from hot methanol to give 461.7 mg of the product as a yellow solid (Yield: 67%). $^1$H NMR (MeOD) δ 8.29 (d, J=8.6 Hz, 2H), 7.92-7.58 (m, 4H), 7.41 (t, J=7.7 Hz, 2H), 4.06 (t, J=6.5 Hz, 2H), 3.74 (t, J=6.4 Hz, 2H), 3.63 (t, J=6.5 Hz, 2H), 3.02 (t, J=7.9 Hz, 2H), 2.35 (t, J=6.4 Hz, 2H), 1.23 (t, J=8.0 Hz, 2H). MS (ESI, positive-ion mode): for $C_{21}H_{30}ClN_6O2Pt$ ([M]+), 629.04; found: 629.2.

Synthesis of 2-((2-(acridin-9-ylamino)ethyl)glycine (4-4; n=1, m=0, Scheme 4)

2-((2-Aminoethyl)glycine (4-3) was synthesized following the method reported by Gilon. 2-((2-(Acridin-9-ylamino)ethyl)glycine was synthesized as follows. A mixture of phenoxyacridine (1.35 g, 0.005 mol) and 4-3 (0.65 g, 0.0055 mol) in 20 mL of dry MeOH was refluxed for 36 h. The yellow solid that precipitated during the reaction was collected by filtration, and washed with ethanol and ether, then dried in a vacuum, affording 2.2 g of the product as a yellow solid (Yield: 75%). The structural identity of this compound was confirmed by ESI-MS rather than by NMR spectroscopy due to limited solubility of the compound in common NMR solvents. ESI-MS, +ve mode, m/z [(M+H]$^+$=296.

Synthesis of 2-((2-((2-(acridin-9-ylamino)ethyl)(tert-butoxycarbonyl)glycine (5-2; n=1, m=1, R=NHCH$_2$CH$_2$N$_3$, Scheme 5)

2-((2-(Acridin-9-ylamino)ethyl)amino)acetic acid (5-1, 296 mg, 0.001 mol) was suspended in 30 mL of anhydrous CH$_2$Cl$_2$ containing triethylamine (121 mg, 0.0012 mol), followed by dropwise addition of Boc$_2$O (283 mg, 0.0013 mol) dissolved in 5 mL of anhydrous CH$_2$Cl$_2$ at 0° C. When addition was complete, the temperature was increased to room temperature and the mixture was stirred for 16 h. The reaction mixture was washed with 3×30 mL of 0.01 M HCl and 20 mL of water to remove unreacted precursors and triethylamine base. The organic phase was collected, dried over Na$_2$SO$_4$ and concentrated by rotary evaporation. The residue was recrystallized from MeOH and ether (v:v=1:1) to afford 300 mg of the final product as a yellow solid (Yield: 76%). Intermediate 5-2 was characterized by ESI-MS and used in the next step without further purification.

Synthesis and deprotection of tert-butyl(2-(acridin-9-ylamino)ethyl)(2-((2-azldoethyl)amino)-2-oxoethyl) carbamate (5-3; n=1, m=1, R=NHCH$_2$CH$_2$N$_3$, Scheme 5)

Acridine derivative 5-2 (198 mg, 0.0005 mol) was dissolved in 10 mL of anhydrous DMF, to which was added 1,1'-carbonyldiimidazole (CDI) (123 mg, 0.00075 mol). The mixture was stirred at 40° C. for 1 h. The mixture was cooled to room temperature, and 2-azidoethanamine (43 mg, 0.0005 mol) was added dropwise, and stirring was continued at room temperature for another 2 h. The solvent was removed in a vacuum and the residue was re-dissolved in 30 mL of CH$_2$Cl$_2$. The solution was washed with 3×30 mL of 0.01 M HCl and water. The organic phase was dried over Na$_2$SO$_4$ and the solvent removed by rotary evaporation to afford 135 mg of the protected amine (5-3) as an orange oil (58%). To remove the Boc protecting group, the oil was dissolved in 8 mL of a mixture (V/V=1:1) of anhydrous CH$_2$Cl$_2$ and trifluoroacetic acid (TFA), and the mixture was stirred at 25° C. for 1 h. The CH$_2$Cl$_2$/TFA mixture was removed by rotary evaporation and the residue was re-dissolved in 30 mL of CH$_2$Cl$_2$. The solution was washed with 15 mL of 2 M ammonium hydroxide, and the organic layer was dried over Na$_2$SO$_4$ and concentrated to yield 101 mg of the free acridine amine 5-4 as an orange oil in 95% yield. $^1$H NMR (CDCl$_3$) δ 8.13 (2H, d, J=8.6 Hz), 7.99 (2H, s), 7.66 (2H, t, J=7.5 Hz), 7.36 (2H, t, J=7.7 Hz), 7.12 (1H, s), 3.88 (2H, t, J=5.5 Hz), 3.36 (6H, m), 2.97 (2H, t, J=5.6 Hz).

Synthesis of methyl-2-((2-(acridin-9-ylamino)ethyl) amino)acetate (7-2, n, m=1, R=CH$_3$, Scheme 7)

To a suspension of 2-((2-(acridin-9-ylamino)ethyl)glycine (2.96 g, 0.01 mol) in 150 mL of dry methanol was added dropwise SOCl$_2$ (11.9 g, 0.1 mol) at 0-5° C. After the addition was complete, the temperature was slowly increased to 25° C.

and stirring was continued for 1 h. The mixture was then refluxed for additional 16 h. The solvent was removed by rotary evaporation and the residue was recrystallized from cold methanol. Yellow crystals of the hydrochloride salt were recovered by filtration and treated with a mixture of 100 mL of 2 M ammonium hydroxide and 100 mL of $CH_2Cl_2$ for 1 h. The aqueous phase was extracted with $CH_2Cl_2$, and the organic phases were combined and dried over anhydrous $Na_2SO_4$. Removal of the solvent resulted in 2.17 g of compound 7-2 as an orange oil (Yield: 69%). $^1H$ NMR ($CDCl_3$) δ 68.19 (2H, d, J=8.7 Hz), 8.65 (2H d, J=8.6 Hz), 7.6 (2H, t, J=7.6 Hz), 7.37 (2H, t, J=7.6 Hz), 6.35 (1H, s), 3.87 (2H, t, J=5.3 Hz), 3.77 (3H, s), 3.53 (2H, s), 2.91 (2H, t, J=5.6 Hz), 2.97 (2H, t, J=5.70 Hz).

Experimental Procedure for Click Reactions

Stock solutions of the platinum-nitrile complexes P1-P6 (20 mM) and acridine derivatives A1-A10 were prepared in anhydrous DMF. Concentrations of A1-A10 were determined spectrophotometrically ($\lambda_{max}$=413 nm, ε=10,000 $M_{-1}$ $cm_{-1}$). The reactions between platinum complexes and acridine derivatives were carried out in 1.5-mL Eppendorf tubes by mixing equal volumes (100 μL) of platinum-nitrile complex and acridine derivative. The reaction mixtures were placed in a shaker and incubated at 4° C. for 5 days. To detect and characterize the hybrid agents and to determine conversion yields, 1-μL samples were removed from each reaction and diluted with 1.000 mL of methanol containing 0.1% formic acid prior to in-line LC-ESMS analysis. Sample injections into the LC unit were accomplished via a thermostatted 4° C.) autosampler. Chromatographic separations were performed with a 4.6 mm×150 mm reversephase Agilent ZORBAX SB-C18 (5 μm) analytical column with the column temperature maintained at 25° C. The binary mobile phase consisted of: solvent A, optima water, and solvent B, methanol/0.1% formic acid delivered at a gradient of 95% A to 5% A over 12 minutes and a flow rate of 0.5 mL/min. The formation and the extent of conversion of the "Pt-Acridine" were determine from the corresponding chromatograms using the LC/MSD Trap Control 4.0 data analysis software.

The modular click approach in conjunction with the facile preparation of building blocks provides a powerful tool for efficient screening of second-generation derivatives of these promising cytotoxics. The use of metal-based coupling chemistry as an efficient screening tool for the discovery of metal-containing (hybrid) pharmacophores is a previously unexplored approach. Here, we provided proof-of-concept data by generating 60 hybrid agents and testing them in one cancer cell line. We envision that this assay can easily be extended to multi-step library synthesis, for instance by combining the platinum-mediated additions with other forms of click chemistry. Likewise, parallel testing in multiple cell lines would add another dimension to this assay. Such an approach would ultimately lend itself to cluster analysis of extended databases with the ultimate goal of designing personalized oncology drugs that can be targeted to specific cancer types.

NMR Spectroscopy. NMR spectra in arrayed experiments were collected at 37° C. on a Bruker 500 DRX spectrometer equipped with a triple-resonance broadband inverse probe and a variable temperature unit. Reactions were performed in 5-mm NMR tubes containing 2 mM complex and 6 mM 5'-GMP (10 mM phosphate buffer, $D_2O$, pH* 6.8). 1-D $^1H$ kinetics experiments were carried out as a standard Bruker arrayed 2-D experiment using a variable-delay list. Incremented 1-D spectra were processed exactly the same, and suitable signals were integrated. Data were processed with XWINNMR 3.6 (Bruker, Ettlingen, Germany). The concentrations of platinum complex at each time point were deduced from relative peak intensities, averaged over multiple signals to account for differences in proton relaxation, and the data were fitted to the equation, $y=A_0 \times e^{-x/t}$ (where $A_0$=1 and $t^{-1}=k_{obs}$), using Origin 7 (OriginLab, Northampton, Mass.). 2-D HMQC experiments were also performed.

In vitro Studies

Restriction Enzyme Cleavage Assay. The top and bottom strands of a 40-base-pair DNA fragment were synthesized and HPLC-purified by IDT Inc. (Coralville, Iowa). The top strand was radioactively labeled using T4 polynucleotide kinase (EPICENTRE Biotechnologies. Madison, Wis.) and [γ-$^{32}$P]ATP (Amersham Biosciences, Piscataway, N.J.) prior to annealing with the complementary strand in reaction buffer (10 mM Tris-HCl, pH 7.5, 50 mM NaCl). Conjugates 11 and 14a were incubated with labeled probe at 37° C. at a drug-to-nucleotide ratio of 0.1, and the samples withdrawn at various time points from the mixtures were treated with thiourea (5-fold the concentration of drug) at 4° C. for 30 min. Unmodified and drug-modified DNA samples were reacted with 60 units of EcoRI (New England Biolabs, Beverly, Mass.) at 37° C. for 40 min in enzyme buffer provided by the vendor. Digested and undigested fragments were separated on polyacrylamide gels (12% acrylamide, 8 M urea) and quantified on a BioRad FX-Pro Plus phosphorimager (Hercules, Calif.) using the BioRad Quantity One software (version 4.4.1).

DNA Polymerase Inhibition Assay. A 221-base-pair NdeI/HpaI restriction fragment from plasmid pSP73 was generated by PCR amplification and purified according to a published protocol. (Guddneppanavar et al. 2007). Appropriate amounts of DNA (10 μg/50 μL) were incubated with complexes 11, 14a, and cisplatin at a drug-to-nucleotide ratio of 0.0075 in 10 mM Tris-HCl (pH 8.0) at 37° C. for 24 h. All other manipulations and experimental conditions of this assay were adopted from previously optimized protocols (Guddneppanavar et al. 2007), including 5' end-labeling of primer, PCR protocols for dideoxy sequencing and footprinting reactions using Taq polymerase (Promega, Madison, Wis.), and details of the gel electrophoresis and documentation.

Cytotoxicity Assay. Cytotoxicity studies were carried out according to a standard protocol (Guddneppanavar et al. 2006) using the Celltiter 96 Aqueous Non-Radioactive Cell Proliferation Assay kit (Promega, Madison, Wis.). Stock solutions of 11, 14a, and 14b were prepared in phosphate-buffered saline (PBS) and serially diluted with media prior to incubation with cancer cells. $IC_{50}$ values were calculated from non-linear curve fits using a sigmoidal dose-response equation in GraphPad Prism (GraphPad Software, La Jolla, Calif.).

Cell Culture.

The human non-small cell lung cancer cell line, NCI-H460, was obtained from the American Type Culture Collection (Rockville, Md., USA) and was cultured in RPMI-1640 media (HyClone) containing 4.5 g/L glucose, 1.5 g/L sodium bicarbonate, 10 mM HEPES, and 110 mg/L sodium pyruvate supplemented with 10% fetal bovine serum (FBS), 10% pen-strep (P&S), and 10% L-glutamine. Cells were incubated at a constant temperature at 37° C. in a humidified atmosphere containing 5% $CO_2$ and were subcultured every 2 to 3 days in order to maintain cells in logarithmic growth.

Cell Proliferation Assay. Cell viability was assessed using the CellTiter 96 Aqueous Non-Radioactive Cell Proliferation Assay (Promega, Madison. Wis., USA) as described previously. Briefly, NCI-H460 cell suspensions were harvested and seeded into 96-well microplates at a density of 750 cells/well. The cells were preincubated at 37° C. overnight and then treated with 50 nM compound from the library reactions or serial dilutions of selected purified compounds (the DMF content in the mixtures was less than 1% at the highest incubation concentration), as well as control samples containing platinum and acridine precursors and samples containing media/DMF. After an incubation period of 72 h, 20 µL of MTS/PMS solution was added to each well and incubated at 37° C. for 4 h. The absorbance of tetrazolium dye was measured at 490) nm using a plate reader. The fraction of viable cells was calculated as a percentage of untreated control and is reported as the mean±standard deviation for 3 incubations of each compound. $IC_{50}$ values were calculated from non-linear curve fits using a sigmoidal dose-response equation in GraphPad Prism (GraphPad Software, La Jolla, Calif.) and are averages of two individual experiments performed in triplicate.

Treatment of Cancer/In Vivo Studies

Xenograft Study. H460 xenografts were established in nude athymic female mice via bilateral subcutaneous injections. Treatment began when the average tumor volume was approximately 100 mm³. The tumor-bearing mice were randomized depending on tumor volume into three groups of five test animals each: one control group receiving vehicle only, one group treated at 0.1 mg/kg 5d/w×2 (A), and one group treated at 0.5 mg/kg q4d×3 (B). Animal weights and tumor volumes were measured and recorded for 17 days after the first dose was administered. Tumor volumes were determined using the formula: $V (mm^3) = d^2 \times D/2$, where d and D are the shortest and longest dimension of the tumor, respectively, and are reported as the sum of both tumors for each test animal. At the end of the study, all animals were euthanized and disposed of according to Standard Operating Procedures (SOPs). Statistical analysis of the growth curves was done using a non-linear polynomial random-coefficient model in SAS Proc Mixed (SAS Institute Inc., Cary, N.C.).

The compounds of the present invention were studied for their cytotoxic effect in the human leukemia cell line, HL-60, and the NSCLC cell line, NCI-H460. The results of the cell proliferation assay are summarized below in Table I.

TABLE 1

Cytotoxicity Data

| Compound | $IC_{50}$ (µM) ± SEM* | |
|---|---|---|
| | HL-60 | NCI-H460 |
| 11 | 3.95 ± 0.24 | 0.35 ± 0.017 |
| 14a (scheme 3) | 2.97 ± 0.11 | 0.028 ± 0.0024 |
| 14b (scheme 3) | 0.47 ± 0.06 | 0.026 ± 0.0022 |

*Concentrations of compound that reduce cell viability by 50%, determined by cell proliferation assays. Cells were incubated with drug for 72 h. Values are means of four experiments ± the standard error of the mean.

As can be seen from Table 1, in HL-60, the compounds of the present invention showed activity based on IC50 values that were in the micromolar range. All of the compounds of the present invention showed very good activity against the H460 cell line. Compound 11 is shown below.

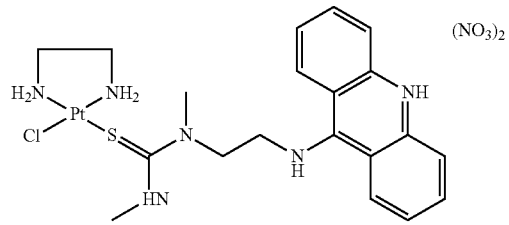

The antitumor activity of compound 14b was evaluated against H460 bilateral tumors implanted into athymic nude mice. Complex 14b was selected for this study, because it was slightly more soluble in biological media than 14a. Complex 14b was administered intraperitonealy (i.p.) according to the following dosing schedules: (A) 0.1 mg/kg, five days per week for two consecutive weeks (5d/w×2), and (B) 0.5 mg/kg, three doses given at 4-day intervals (q4d×3). The tumor volumes recorded in both treatment groups and in untreated control animals are plotted vs. days of treatment in FIG. 1. At the end of the study, the tumors measured 1834±160, 1798±309, and 1102±319 mm³ (means±S.E.M.) for the control animals and animals treated according to schedules A and B, respectively. Based on these data, the low-dose treatment (A) had no effect on tumor growth. However, treatment at the higher dose (B), which is close to the maximum tolerated dose (MTD) of compound 14b, slowed the tumor growth rate significantly (P<0.01) compared to the control group, which led to a reduction in the mean terminal tumor volume by 40%.

Complexes 14a and 14b are remarkably cytotoxic in H460 NSCLC cells. These are two of a very limited number of drugs known to inhibit H460 cell growth with similar potency in the nanomolar concentration range. Cisplatin is at least 20-fold less potent than the non-classical compounds of the present invention in H460 cells with $IC_{50}$ values typically in the micromolar range. The high cell kill potential of the compounds of the present invention in H460 cells translates into pronounced antitumor activity. This was demonstrated for compound 14b in the corresponding tumor xenograft, in which the drug slowed tumor growth at a sub-lethal dose close to the MTD. The high cytotoxic potency of compound 14b is documented by the fact that it is tolerated at doses an order of magnitude lower than those commonly applied for cisplatin when administered i.p. The new compounds of the present invention show significantly improved cytotoxic potential compared to the 'classical' monofunctional, complex, cis-[Pt(NH$_3$)$_2$(pyridine)Cl]$^+$, which requires high drug doses to produce an appreciable antitumor effect in vivo.

In an embodiment, the compounds of the present invention display cytotoxic effects against several different types of cancer, that are in general more effective than cisplatin. The following Table II illustrates the efficacy of the compounds of the present invention against these various types of cancers.

| compound | NCI-H460 (NSCLC) | OVCAR-3 (ovarian) | MDA-MB-231 (triple-negative breast) | MCF-7 (ER + breast) | PANC-1 (pancreatic) |
|---|---|---|---|---|---|
| cisplatin | 1.2 ± 0.2 | 3.3 ± 0.4 | 60 ± 7 | 12 ± 2 | 6.6 ± 0.7 |
| WFU-001 | 0.008 ± 0.001 | 1.1 ± 0.1 | 15 ± 2 | 2.5 ± 0.1 | 0.092 ± 0.012 |

| compound | NCI-H460 (NSCLC) | OVCAR-3 (ovarian) | MDA-MB-231 (triple-negative breast) | MCF-7 (ER+ breast) | PANC-1 (pancreatic) |
| --- | --- | --- | --- | --- | --- |
| WFU-002 | 0.036 ± 0.006 | Not tested | Not tested | Not Tested | Not tested |
| WFU-003 | 0.011 ± 0.001 | 1.7 ± 0.1 | 9.9 ± 1.4 | 3.6 ± 0.3 | 0.086 ± 0.009 |
| WFU-004 | 0.052 ± 0.006 | 33 ± 9 | 12 ± 2 | 11 ± 1 | 4.4 ± 0.6 |
| WFU-005 | 0.065 ± 0.008 | 150 ± 40 | 36 ± 2 | 19 ± 1 | 2.2 ± 0.6 | shows Cytotoxicity Data ($IC_{50}$ values [μM] for 72-h incubations performed in triplicate) for WFU001-WFU005 and Cisplatin in Colorimetric Cell Proliferation Assays The structures of the above indicated compounds WFU-001-005 from Table II are shown below:

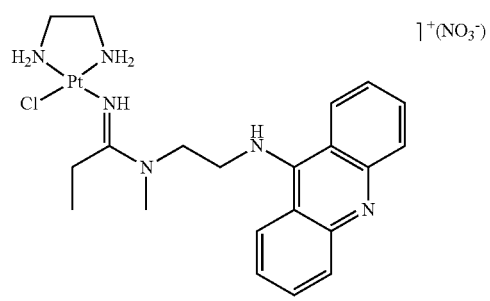

WFU-001

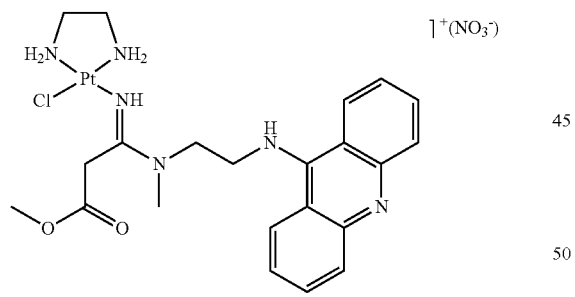

WFU-002

WFU-003

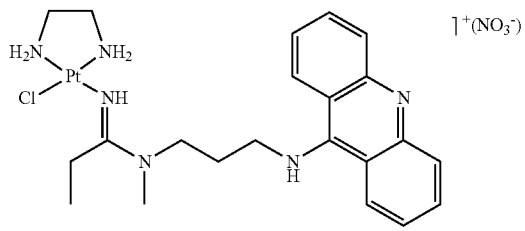

WFU-004

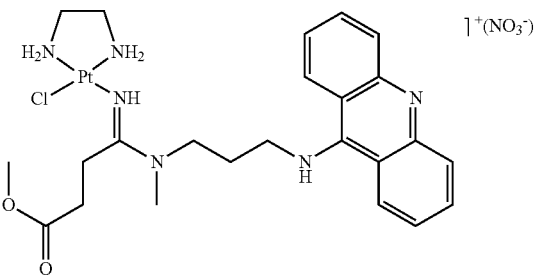

WFU-005

One additional compound that shows promise and has an IC50 (NCI-H460) of 2.8 nM is compound WFU-001a, which is shown below.

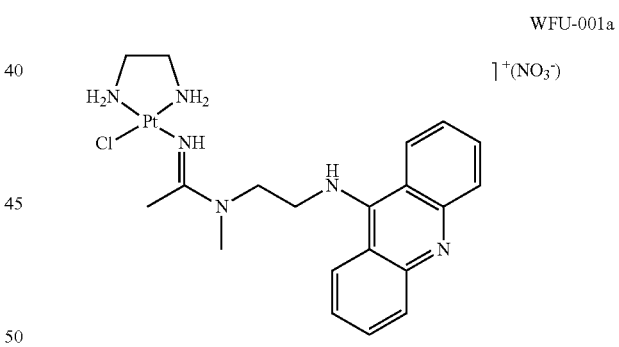

WFU-001a

Figure 19:
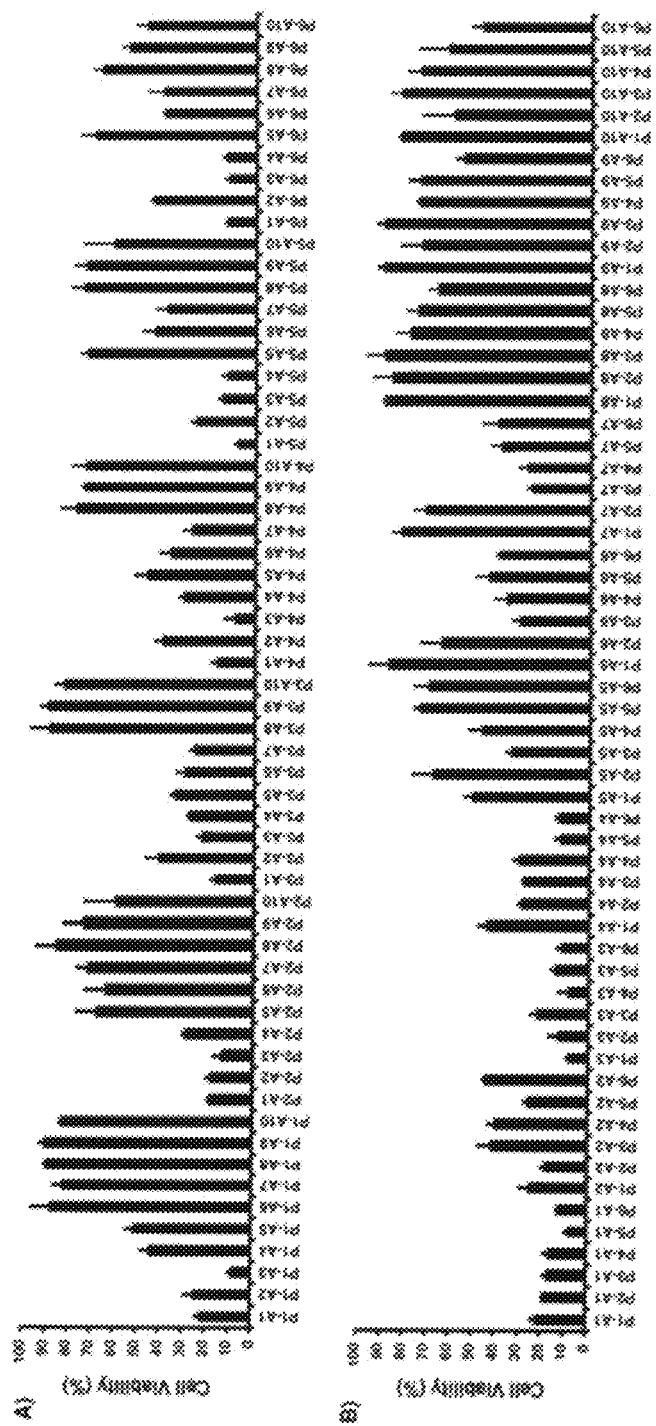
FIG. 19 shows the biological activity profiles for 60 compounds based on the viabilities of treated cells relative to untreated control determined in a colorimetric cell proliferation assay. The test compounds are sorted by common platinum moieties in (A) and by common acridine moieties in (B). Error bars indicate ±standard deviations for sets of three data points for each compound.

On the basis of the mean cell viabilities calculated across the entire set of 60 library members (see FIG. 19), the various hybrids were quite effective. To assess the utility of the library screen as a tool for target compound identification, a structurally diverse subset of four analogues of interest were resynthesized and tested in NCI-H460 cells. $IC_{50}$ values were calculated from the corresponding dose-response curves and gave $IC_{50}$ values of between about 2.8 and 110 nM. Synergistic effects between multiple components, which might lead to enhanced cell kill, cannot be completely ruled out.

Thus, in an embodiment of the present invention, compounds and methods of Formula I and compositions containing Formula I are contemplated.

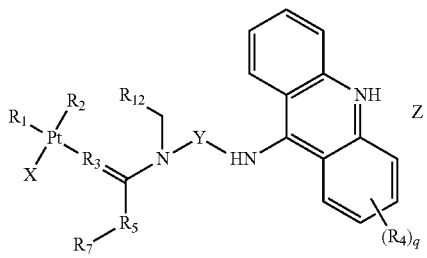

Formula I wherein X is halo, —OC(O)R$_9$, nitrate or sulfate;

R$_1$ and R$_2$ are amino groups or together with the platinum atom to which they are attached, R$_1$ and R$_2$ form the ring —NH$_2$—(CH$_2$)$_v$—NH$_2$— wherein v is 1, 2, 3, or 4;

R$_3$ is —N(R$_6$)—; wherein R$_6$ is hydrogen or C$_1$-C$_6$alkyl;

R$_4$ is independently an amino, a nitro, —NHC(O)(R$_{10}$), —NHC(O)O(R$_{10}$), —C(O)NHR$_{10}$, —OC(O)NHR$_{10}$, or halo;

R$_{10}$ is hydrogen, C$_{1-6}$ alkyl, phenyl, naphthyl, C$_{3-6}$ cycloalkyl, norbornyl, or adamantyl;

q is 0, 1, or 2;

R$_5$ is a direct bond, —NH— or C$_1$-C$_6$alkylene;

or R$_5$ and X together with the atoms to which they are attached form a 6- or 7-membered ring, wherein said 6- or 7-membered ring contains a linking group —C(O)O— or —OC(O)—;

R$_7$ is hydrogen, methyl, or —C(O)O—R$_8$; wherein

R$_8$ is hydrogen, C$_{1-6}$ alkyl, phenyl, naphthyl, C$_{3-6}$ cycloalkyl, norbornyl, or adamantyl, a natural or unnatural amino acid or a peptide;

R$_9$ is hydrogen, C$_{1-6}$ alkyl, phenyl, naphthyl, C$_{3-6}$ cycloalkyl, norbornyl, or adamantyl;

R$_{12}$ is as defined above;

Y is C$_1$-C$_6$alkyl; and

Z is one or more counterions sufficient to balance the charge of the compound.

In an embodiment, the present invention discloses methods of treating cancer in an individual in need thereof by the use of a compound of Formula I.

In a variation, the compounds of the present invention can be used for treating diseases of abnormal cell growth and/or dysregulated apoptosis, such as cancer, mesothioloma, bladder cancer, pancreatic cancer, skin cancer, cancer of the head or neck, cutaneous or intraocular melanoma, ovarian cancer, breast cancer, uterine cancer, carcinoma of the fallopian tubes, carcinoma of the endometrium, carcinoma of the cervix, carcinoma of the vagina, carcinoma of the vulva, bone cancer, ovarian cancer, cervical cancer, colon cancer, rectal cancer, cancer of the anal region, stomach cancer, gastrointestinal (gastric, colorectal, and duodenal), chronic lymphocytic leukemia, esophageal cancer, cancer of the small intestine, cancer of the endocrine system, cancer of the thyroid gland, cancer of the parathyroid gland, cancer of the adrenal gland, sarcoma of soft tissue, cancer of the urethra, cancer of the penis, testicular cancer, hepatocellular cancer (hepatic and billiary duct), primary or secondary central nervous system tumors, primary or secondary brain tumors, Hodgkin's disease, chronic or acute leukemias, chronic myeloid leukemia, lymphocytic lymphomas, lymphoblastic leukemia, follicular lymphoma, lymphoid malignancies of T-cell or B-cell origin, melanoma, multiple myeloma, oral cancer, ovarian cancer, non-small cell lung cancer, prostate cancer, small cell lung cancer, cancer of the kidney and ureter, renal cell carcinoma, carcinoma of the renal pelvis, neoplasms of the central nervous system, primary central nervous system lymphoma, non-Hodgkin's lymphoma, spinal axis tumors, brains stem glioma, pituitary adenoma, adrenocortical cancer, gall bladder cancer, cancer of the spleen, cholangiocarcinoma, fibrosarcoma, neuroblastoma, retinoblastoma, or a combination thereof.

In a variation, the compounds of the present invention can be used in the treatment of non-small cell lung cancer, pancreatic cancer, breast cancer, and ovarian cancer. Alternatively, the compounds of the present invention can be used in the treatment of non-small cell lung cancer, pancreatic, and ovarian cancer.

In a further variation, the compounds of the present invention can be used in methods of treating mesothioloma, bladder cancer, pancreatic cancer, skin cancer, cancer of the head or neck, cutaneous or intraocular melanoma, ovarian cancer, breast cancer, uterine cancer, carcinoma of the fallopian tubes, carcinoma of the endometrium, carcinoma of the cervix, carcinoma of the vagina, carcinoma of the vulva, bone cancer, ovarian cancer, cervical cancer, colon cancer, rectal cancer, cancer of the anal region, stomach cancer, gastrointestinal (gastric, colorectal, and duodenal), chronic lymphocytic leukemia, esophageal cancer, cancer of the small intestine, cancer of the endocrine system, cancer of the thyroid gland, cancer of the parathyroid gland, cancer of the adrenal gland, sarcoma of soft tissue, cancer of the urethra, cancer of the penis, testicular cancer, hepatocellular cancer (hepatic and billiary duct), primary or secondary central nervous system tumor, primary or secondary brain tumor, Hodgkin's disease, chronic or acute leukemia, chronic myeloid leukemia, lymphocytic lymphomas, lymphoblastic leukemia, follicular lymphoma, lymphoid malignancies of T-cell or B-cell origin, melanoma, multiple myeloma, oral cancer, ovarian cancer, non-small cell lung cancer, prostate cancer, small cell lung cancer, cancer of the kidney and ureter, renal cell carcinoma, carcinoma of the renal pelvis, neoplasms of the central nervous system, primary central nervous system lymphoma, non-Hodgkin's lymphoma, spinal axis tumors, brains stem glioma, pituitary adenoma, adrenocortical cancer, gall bladder cancer, cancer of the spleen, cholangiocarcinoma, fibrosarcoma, neuroblastoma, retinoblastoma, or a combination of one or more of the above cancers in a patient, said methods comprising administering thereto a therapeutically effective amount of a compound having formula (II).

In a variation, the compounds of the present invention can be used in methods in the treatment of non-small cell lung cancer, pancreatic cancer, breast cancer, and ovarian cancer. Alternatively, the compounds of the present invention can be used in methods in the treatment of non-small cell lung cancer, pancreatic, and ovarian cancer.

In a further variation, the compounds of the present invention can be used for treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer and spleen cancer.

In a variation of the method, the cancer may alternatively be selected from the group consisting of lung cancer, genitourinal cancers, bladder cancers, testicular cancers, ovarian carcinomas, various head and neck cancers, colon cancers, various leukemias, and various lymphomas.

In another variation of the method, the variables of formula I may be any of the follows:

$R_3$ may be —N($R_6$)—, wherein $R_6$ is $C_{1-6}$alkyl or hydrogen. In a variation, Y may be —$CH_2$—. In a variation, $R_1$ and $R_2$ may be amino groups or together with the platinum atom to which $R_1$ and $R_2$ are attached are —$NH_2$—$CH_2$—$NH_2$—. In a variation, the counter ion Z comprises $NO_3$. In a further variation, $R_5$ may be —NH— or —$CH_2$—. In a further variation, $R_6$ may be hydrogen or methyl.

In another embodiment, the present invention is directed to a pharmaceutical composition comprising the compound of Formula I:

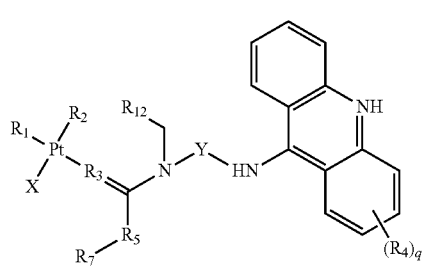

Formula I wherein X is halo, —OC(O)$R_9$, nitrate or sulfate;

$R_1$ and $R_2$ are amino groups or together with the platinum atom to which they are attached, $R_1$ and $R_2$ form the ring —$NH_2$—($CH_2$)$_v$—$NH_2$— wherein v is 1, 2, 3, or 4;

$R_3$ is —N($R_6$)—, wherein $R_1$ is hydrogen or $C_1$-$C_6$alkyl;

$R_4$ is independently an amino, a nitro, —NHC(O)($R_{10}$), —NHC(O)O($R_{10}$), —C(O)NH$R_{10}$, —OC(O)NH$R_{10}$, or halo;

$R_{10}$ is hydrogen, $C_{1-6}$ alkyl, phenyl, naphthyl, $C_{3-6}$ cycloalkyl, norbornyl, or adamantyl;

q is 0, 1, or 2;

$R_5$ is a direct bond, —NH— or $C_1$-$C_6$alkylene;

or $R_5$ and X together with the atoms to which they are attached form a 6- or 7-membered ring, wherein said 6- or 7-membered ring contains a linking group —C(O)O— or —OC(O)—;

$R_7$ is hydrogen, methyl, or —C(O)O—$R_8$; wherein $R_8$ is hydrogen, $C_{1-6}$ alkyl, phenyl, naphthyl, $C_{3-6}$ cycloalkyl, norbornyl, or adamantyl, a natural or unnatural amino acid or a peptide;

$R_9$ is hydrogen, $C_{1-6}$ alkyl, phenyl, naphthyl, $C_{3-6}$ cycloalkyl, norbornyl, or adamantyl;

$R_{12}$ is as defined above;

Y is $C_1$-$C_6$alkyl; and

Z is one or more counterions sufficient to balance the charge of the compound; and pharmaceutically acceptable diluents, carriers, or excipients.

In a variation, the pharmaceutical composition may have variables that are defined as follows: Y may be —$CH_2$—, $R_1$ and $R_2$ may be amino groups or together with the platinum atom to which $R_1$ and $R_2$ are attached may be —$NH_2$—$CH_2$—$NH_2$—, and wherein the counter ion Z comprises $NO_3$.

In a variation, the pharmaceutical composition optionally has the variables defined as follows: $R_5$ is —NH— or —$CH_2$— and $R_6$ is hydrogen or methyl.

The pharmaceutical composition may contain pharmaceutically acceptable salts, solvates, and prodrugs thereof, and may contain diluents, excipients, carriers, or other substances necessary to increase the bioavailability or extend the lifetime of the compounds of the present invention.

Subjects that may be treated by the compounds and compositions of the present invention include, but are not limited to, horses, cows, sheep, pigs, mice, dogs, cats, primates such as chimpanzees, gorillas, rhesus monkeys, and, humans. In an embodiment, a subject is a human in need of cancer treatment.

The pharmaceutical compositions containing a compound of the invention may be in a form suitable for injection either by itself or alternatively, using liposomes, micelles, and/or nanospheres.

Figure 21:
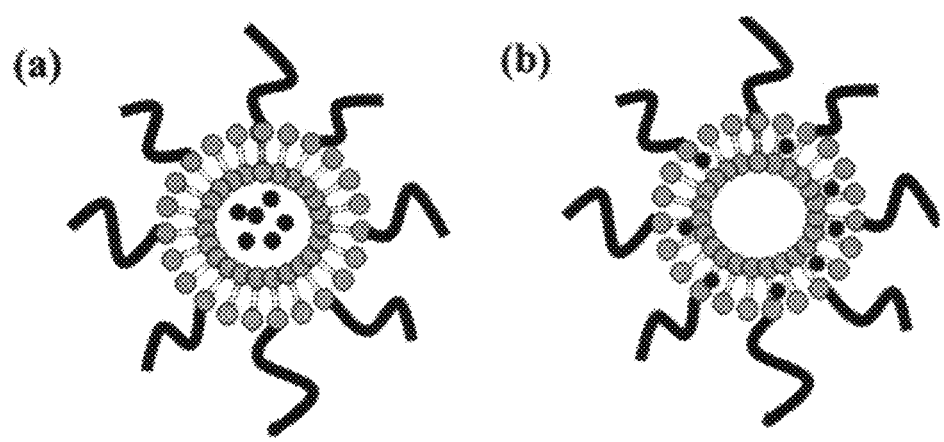
FIG. 21 shows liposomes for passive delivery of platinum-acridines.

FIG. 21 shows stealth mPEG-modified liposomal formulations containing (a) unmodified platinum-acridines (small circles) encapsulated as hydrophilic warheads in the core of an liposome, and (b) hydrophobic platinum-acridine conjugates (small circles) (for example, fatty acid-modified) incorporated into the bilayers. The pharmaceutical composition suitable for injection can be made as disclosed in Lammers, T. et al., J. Controlled Release, 161, 175-187 (2012), or in Barenholz, Y., J. Controlled Release, 160, 117-134, (2012), both of which are incorporated by reference in their entireties. Alternatively, compositions intended for injection may be prepared according to any known method, and such compositions may contain one or more agents selected from the group consisting of solvents, co-solvents, solubilizing agents, wetting agents, suspending agents, emulsifying agents, thickening agents, chelating agents, antioxidants, reducing agents, antimicrobial preservatives, buffers, pH adjusting agents, bulking agents, protectants, tonicity adjustors, and special additives. Moreover, other non-toxic pharmaceutically-acceptable excipients which are suitable for the manufacture of injectables may be used.

Aqueous suspensions may contain the active compounds in an admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyleneoxycethanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more coloring agents.

Oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents may also be present.

The pharmaceutical compositions of the invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The pharmaceutical compositions may be in the form of a sterile injectable aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, sterile water for injection (SWFI), Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

Thus, in another embodiment, the present invention provides a pharmaceutical formulation solution comprising a compound of Formula I or a salt thereof.

A solution of the invention may be provided in a sealed container, especially one made of glass, either in a unit dosage form or in a multiple dosage form.

Any pharmaceutically acceptable salt of a compound of Formula I may be used for preparing a solution of the invention. Examples of suitable salts may be, for instance, the salts with mineral inorganic acids such as hydrochloric, hydrobromic, sulfuric, phosphoric, nitric and the like, and the salts with certain organic acids such as acetic, succinic, tartaric, ascorbic, citric, glutamic, benzoic, methanesulfonic, ethanesulfonic and the like. In an embodiment, the compound of Formula I is a hydrochloric acid salt including a mono, di, or trihydrochloride.

Any solvent which is pharmaceutically acceptable and which is able to dissolve the compounds of Formula I or a pharmaceutically acceptable salt thereof may be used. The solution of the invention may also contain one or more additional components such as a co-solubilizing agent (which may be the same as a solvent), a tonicity adjustment agent, a stabilizing agent, a preservative, or mixtures thereof. Examples of solvents, co-solubilizing agents, tonicity adjustment agents, stabilizing agents and preservatives which may be suitable for a solution formulation are described below.

Suitable solvents and co-solubilizing agents may include, but are not limited to, water; sterile water for injection (SWFI); physiological saline; alcohols, e.g. ethanol, benzyl alcohol and the like; glycols and polyalcohols, e.g. propyleneglycol, glycerin and the like; esters of polyalcohols, e.g. diacetine, triacetine and the like; polyglycols and polyethers, e.g. polyethyleneglycol 400, propyleneglycol methylethers and the like; dioxolanes, e.g. isopropylidenglycerin and the like; dimethylisosorbide; pyrrolidone derivatives, e.g. 2-pyrrolidone, N-methyl-2-pyrrolidone, polyvinylpyrrolidone (co-solubilizing agent only) and the like; polyoxyethylenated fatty alcohols; esters of polyoxyethylenated fatty acids; polysorbates, e.g., Tween™, polyoxyethylene derivatives of polypropyleneglycols, e.g., Pluronics™.

Suitable tonicity adjustment agents may include, but are not limited to, pharmaceutically acceptable inorganic chlorides, e.g. sodium chloride; dextrose; lactose; mannitol; sorbitol and the like.

Preservatives suitable for physiological administration may be, for instance, esters of parahydroxybenzoic acid (e.g., methyl, ethyl, propyl and butyl esters, or mixtures of them), chlorocresol and the like.

Suitable stabilizing agents include, but are not limited to, monosaccharides (e.g., galactose, fructose, and fucose), disaccharides (e.g., lactose), polysaccharides (e.g., dextran), cyclic oligosaccharides (e.g., alpha-, beta-, gamma-cyclodextrin), aliphatic polyols (e.g., mannitol, sorbitol, and thioglycerol), cyclic polyols (e.g. inositol) and organic solvents (e.g., ethyl alcohol and glycerol).

The above mentioned solvents and co-solubilizing agents, tonicity adjustment agents, stabilizing agents and preservatives can be used alone or as a mixture of two or more of them in a solution formulation.

In an embodiment, a pharmaceutical solution formulation may comprise a compound of Formula I or a pharmaceutically acceptable salt thereof, and an agent selected from the group consisting of sodium chloride solution (i.e., physiological saline), dextrose, mannitol, or sorbitol, wherein the agent is in an amount of less than or equal to 5%. The pH of such a formulation may also be adjusted to improve the storage stability using a pharmaceutically acceptable acid or base.

In the solutions of the invention the concentration of the compound of Formula I or a pharmaceutically acceptable salt thereof may be less than 100 mg/mL, or less than 50 mg/mL, or less than 10 mg mL, or less than 10 mg/mL and greater than 0.01 mg/mL, or between 0.5 m mL and 5 mg/mL, or between 1 mg/mL and 3 mg/mL. In an embodiment, the concentration that is used is the ideal concentration to be sufficiently cytotoxic to the cancer cells yet limit the toxicity on other cells.

Suitable packaging for the pharmaceutical solution formulations may be all approved containers intended for parenteral use, such as plastic and glass containers, ready-to-use syringes and the like. In an embodiment, the container is a sealed glass container, e.g. a vial or an ampoule. A hermetically sealed glass vial is particularly preferred.

According to an embodiment of the present invention, there is provided, in a sealed glass container, a sterile, injectable solution comprising a compound of Formula I or a pharmaceutically acceptable salt thereof in a physiologically acceptable solvent, and which has a pH of from 2.5 to 3.5. For solution formulations, various compounds of the present invention may be more soluble or stable for longer periods in solutions at a pH lower than 6. Further, acid salts of the compounds of the present invention may be more soluble in aqueous solutions than their free base counter parts, but when the acid salts are added to aqueous solutions the pH of the solution may be too low to be suitable for administration. Thus, solution formulations having a pH above pH 4.5 may be combined prior to administration with a diluent solution of pH greater than 7 such that the pH of the combination formulation administered is pH 4.5 or higher. In one embodiment, the diluent solution comprises a pharmaceutically acceptable base such as sodium hydroxide. In another embodiment, the diluent solution is at pH of between 10 and 12. In another embodiment, the pH of the combined formulation administered is greater than 5.0. In another embodiment, the pH of the combined formulation administered is between pH 5.0 and 7.0.

The invention also provides a process for producing a sterile solution with a pH of from 2.5 to 3.5 which process comprises dissolving a compound of Formula I or a pharmaceutically acceptable salt thereof in a pharmaceutically acceptable solvent. Where a pharmaceutically acceptable acid salt of a compound of Formula I is used the pH of the solution may be adjusted using a pharmaceutically acceptable base or basic solution adding a physiologically acceptable acid or buffer to adjust the pH within a desired range. The method may further comprise passing the resulting solution through a sterilizing filter.

Figure 20:
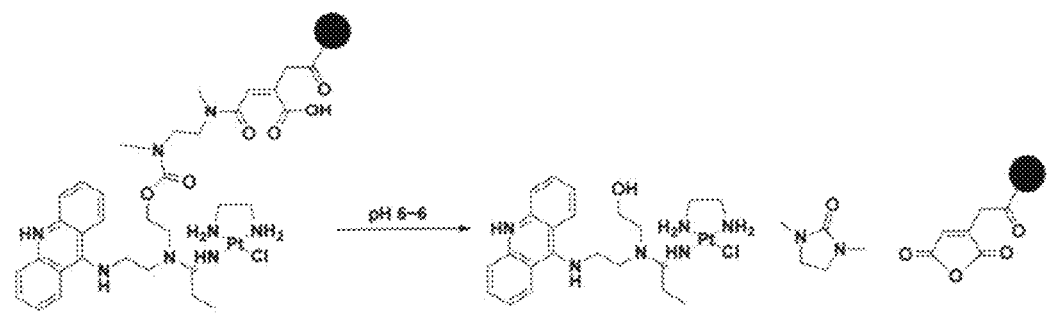
FIG. 20 shows a mechanism of pH-sensitive release for conjugates based on carbamate linkages.

In an embodiment, there may be the release of conjugates based upon pH-sensitivity. This is illustrated in FIG. 20 wherein the pH sensitive release for conjugates based on carbamate linkages is shown. FIG. 20 shows the pH-sensitive release mechanism specifically for warheads containing carrier groups (here folic acid was chosen as an example) coupled via carbamate linkages. In this setup, the group cis-aconic acid is linked to the hydroxyl-modified platinum-acridine agent by using a self-immolative spacer N,N'-dimethyl-ethylenediamine to form an amide bond. The resulting amide is readily cleaved at slightly acidic pH encountered in for example, endosomes and lysosomes.

One or more additional components such as co-solubilizing agents, tonicity adjustment agents, stabilizing agents and preservatives, for instance of the kind previously specified, may be added to the solution prior to passing the solution through the sterilizing filter.

In a further variation, the present invention contemplates combination therapies in which the compounds of the present invention can be used in conjunction with other cisplatin compounds. The efficacy of this combination therapy is likely to be enhanced because of the different mechanisms and modes of action that first generation cisplatin compounds exhibit relative to the compounds of the present invention. It is also contemplated and therefore within the scope of the invention that other anti-neoplastic agents/compounds can be used in conjunction with the compounds of the present invention. The anti-neoplastic agents/compounds that can be used with the compounds of the present invention include cytotoxic compounds as well as non-cytotoxic compounds.

Examples include anti-tumor agents such as HERCEPTIN™ (trastuzumab), RITUXAN™ (rituximab), ZEVALIN™ (ibritumomab tiuxetan), LYMPHOCIDE™ (epratuzumab), GLEEVAC™ and BEXXAR™ (iodine 131 tositumomab).

Other anti-neoplastic agents/compounds that can be used in conjunction with the compounds of the present invention include anti-angiogenic compounds such as ERBITUX™ (IMC-C225), KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF, or soluble VEGF receptors or a ligand binding region thereof) such as AVASTIN™ or VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as ABX-EGF (panitumumab), IRESSA™ (gefitinib), TARCEVA™ (erlotinib), anti-Ang1 and anti-Ang2 agents (e.g., antibodies or antigen binding regions specifically binding thereto or to their receptors, e.g., Tie2/Tek), and anti-Tie2 kinase inhibitory agents (e.g., antibodies or antigen binding regions that specifically bind thereto).

Other anti-angiogenic compounds/agents that can be used in conjunction with the compounds of the present invention include Campath, IL-8, B-FGF, Tek antagonists, anti-TWEAK agents (e.g., specifically binding antibodies or antigen binding regions, or soluble TWEAK receptor antagonists, ADAM distintegrin domain to antagonize the binding of integrin to its ligands, specifically binding anti-eph receptor and/or anti-ephrin antibodies or antigen binding regions, and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto).

Other anti-angiogenic/anti-tumor agents that can be used in conjunction with the compounds of the present invention include: SD-7784 (Pfizer, USA); cilengitide. (Merck KGaA, Germany, EPO 770622); pegaptanib octasodium, (Gilead Sciences, USA); Alphastatin, (BioActa, UK); M-PGA, (Celgene, USA); ilomastat, (Arriva, USA); emaxanib, (Pfizer. USA); vatalanib, (Novartis, Switzerland); 2-methoxyestradiol, (EntreMed, USA); TLC ELL-12, (Elan, Ireland); anecortave acetate, (Alcon, USA); alpha-D148 Mab, (Amgen, USA); CEP-7055, (Cephalon, USA); anti-Vn Mab, (Crucell, Netherlands) DAC:antiangiogenic, (ConjuChem, Canada); Angiocidin, (InKine Pharmaceutical, USA); KM-2550, (Kyowa Hakko, Japan); SU-0879, (Pfizer, USA); GCP-79787, (Novartis, Switzerland); the ARGENT technology of Ariad, USA; YIGSR-Stealth, (Johnson & Johnson, USA); fibrinogen-E fragment, (BioActa, UK); the angiogenesis inhibitors of Trigen, UK; TBC-1635, (Encysive Pharmaceuticals, USA); SC-236, (Pfizer, USA); ABT-567, (Abbott, USA); Metastatin, (EntreMed, USA); angiogenesis inhibitor, (Tripep, Sweden); maspin, (Sosei, Japan); 2-methoxyestradiol, (Oncology Sciences Corporation, USA); ER-68203-00, (WVAX, USA); Benefin, (Lane Labs, USA); Tz-93, (Tsumura, Japan); TAN-1120, (Takeda, Japan); FR-111142, (Fujisawa, Japan); platelet factor 4, (RepliGen, USA); vascular endothelial growth factor antagonist, (Borean, Denmark); bevacizumab (pINN), (Genentech, USA); XL 784, (Exelixis, USA); XL 647, (Exelixis, USA); MAb, alpha5beta3 integrin, second generation, (Applied Molecular Evolution, USA and MedImmune, USA); gene therapy, retinopathy, (Oxford BioMedica, UK); enzastaurin hydrochloride (USAN), (Lilly, USA); CEP 7055, (Cephalon, USA and Sanofi-Synthelabo, France); BC 1, (Genoa Institute of Cancer Research, Italy); angiogenesis inhibitor, (Alchemia, Australia); VEGF antagonist, (Regeneron, USA); rBPI 21 and BPI-derived antiangiogenic, (XOMA, USA); PI 88, (Progen, Australia); cilengitide (pINN), (Merck KGaA, German; Munich Technical University, Germany, Scripps Clinic and Research Foundation, USA); cetuximab (INN), (Aventis, France); AVE 8062, (Ajinomoto, Japan); AS 1404, (Cancer Research Laboratory, New Zealand); SG 292, (Telios, USA); Endostatin, (Boston Children's Hospital, USA); ATN 161, (Attenuon, USA); ANGIOSTATIN, (Boston Children's Hospital, USA); 2-methoxyestradiol, (Boston Children's Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca, UK); vatalanib (pINN), (Novanis, Switzerland and Schering AG, Germany); tissue factor pathway inhibitors, (EntreMed, USA); pegaptanib (Pinn), (Gilead Sciences, USA); xanthorrhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX 478, (ProIX, USA); METASTATIN, (EntreMed, USA); troponin I, (Harvard University, USA); SU 6668, (SUGEN, USA); OXI 4503, (OXiGENE, USA); o-guanidines, (Dimensional Pharmaceuticals, USA); motuporamine C, (British Columbia University, Canada); CDP 791, (Celltech Group, UK); atiprimod (pINN), (GlaxoSmith- Kline, UK); E 7820, (Eisai, Japan); CYC 381, (Harvard University, USA); AE 941, (Aetema, Canada); vaccine, angiogenesis, (EntreMed, USA); urokinase plasminogen activator inhibitor, (Dendreon, USA); oglufanide (pINN), (Melmotte, USA); HIF-lalfa inhibitors, (Xenova, UK); CEP 5214, (Cephalon, USA); BAY RES 2622, (Bayer, Germany); Angiocidin, (InKine, USA); A6, (Angstrom, USA); KR 31372, (Korea Research Institute of Chemical Technology, South Korea); GW 2286, (GlaxoSmithKline, UK); EHT 0101, (ExonHit, France); CP 868596, (Pfizer, USA); CP 564959, (OSI, USA); CP 547632, (Pfizer. USA); 786034, (GlaxoSmithKline, UK); KRN 633, (Kirin Brewery, Japan); drug delivery system, intraocular, 2-methoxyestradiol, (EntreMed, USA); anginex, (Maastricht University, Netherlands, and Minnesota University, USA); ABT 510, (Abbott, USA); AAL 993, (Novartis, Switzerland); VEGI, (ProteomTech, USA); tumor necrosis factor-alpha inhibitors, (National Institute on Aging, USA); SU 11248, (Pfizer, USA and SUGEN USA); ABT 518, (Abbott, USA); YH16, (Yantai Rongchang, China); S-3APG, (Boston Children's Hospital, USA and EntreMed, USA); MAb, KDR, (ImClone Systems, USA); MAb, alpha5 beta1, (Protein Design, USA); KDR kinase inhibitor, (Celltech Group, UK, and Johnson & Johnson, USA); GFB 116, (South Florida University, USA and Yale University, USA); CS 706, (Sankyo, Japan); combretastatin A4 prodrugs, (Arizona State University, USA); chondroitinase AC, (IBEX, Canada); BAY RES 2690, (Bayer, Germany); AGM 1470, (Harvard University, USA, Takeda, Japan, and TAP, USA); AG 13925, (Agouron, USA); Tetrathiomolybdate, (University of Michigan, USA); GCS 100, (Wayne State University, USA) CV 247, (Ivy Medical, UK); CKD 732, (Chong Kun Dang, South Korea); MAb, vascular endothelium growth factor, (Xenova, UK); irsogladine (INN), (Nippon Shinyaku, Japan); RG 13577, (Aventis, France); WX 360, (Wilex, Germany); squalamine (pIN), (Genaera, USA); RPI 4610, (Sima, USA); heparanase inhibitors, (InSight, Israel); KL 3106, (Kolon, South Korea); Honokiol, (Emory University, USA); ZK CDK, (Schering AG, Germany); ZK Angio, (Schering AG, Germany); ZK 229561, (Novartis, Switzerland, and Schering AG, Germany); XMP 300, (XOMA, USA); VGA 1102, (Taisho, Japan); VEGF receptor modulators, (Pharmacopeia, USA); VE-cadherin-2 antagonists, (ImClone Systems, USA); Vasostatin, (National Institutes of Health. USA); vaccine, Flk-1, (ImClone Systems, USA); TZ 93, (Tsumura, Japan); TumStatin, (Beth Israel Hospital, USA); truncated soluble FLT 1 (vascular endothelial growth factor receptor 1), (Merck & Co, USA); Tie-2 ligands, (Regeneron, USA); and, thrombospondin 1 inhibitor, (Allegheny Health, Education and Research Foundation, USA).

It is contemplated and therefore within the scope of the invention that the compounds of the present invention can be modified to target specific receptors or cancer cells or can be modified so that they can survive various in vivo environments. As examples, when X is a carboxylate functionality, X can be modified so that it is combined with dendrimers or other cyclic sugars to form carboxylate dendrimers or other sugars. It may be combined with steroids such as estrogen to form carboxylate steroids like carboxylate estrogen. X or other carboxylate functionalities on these compounds may be modified so that they contain folic acid. Those of skill in the art will recognize that there are other modifications that can be made to the compounds of the present invention so that they can target specific receptors, cells or provide stability to the compounds. It is contemplated that the compounds of the present invention can have modifications made that are covalent modifications, ionic modifications, modified so that they chelate to other compounds, or other undergo some other type of interaction that allows the compounds of the present invention to suit their use (such as hydrophobic or Van der Waals type interactions).

Figure 22:
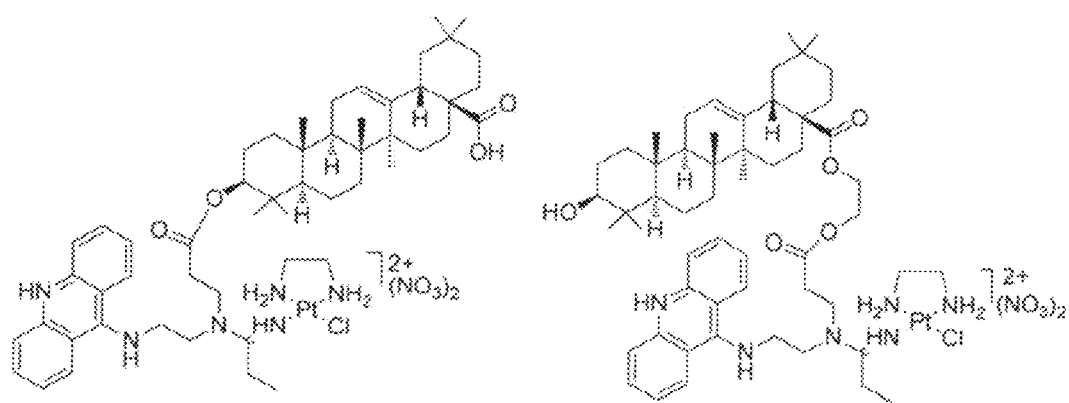
FIG. 22 shows the sensitizing strategy using oleanolic acid attached to a platinum-acridine warhead. Left: hydroxo-linked form, right: carboxylate-linked form. Other natural triterpenoids of interest include Litocholic acid, Betulinic acid, Ursolic acid, Lupenone, Betulin, Uvaol, Arjunolic acid, Asiatic acid.

FIG. 22 shows the sensitizing strategy using steroid type derivatives. In this instance, oleanolic acid is attached to a platinum-acridine warhead. On the left figure, the hydroxo-linked form is shown and on the right, the carboxylate-linked form is shown. Other natural triterpenoids that may be of interest and are within the scope of the present invention include Litocholic acid, Betulinic acid, Ursolic acid. Lupenone, Betulin, Uvaol, Arjunolic acid, Asiatic acid.

In a further variation, the compounds of the present invention can be used against solid tumors, cell lines, and cell line tissue that demonstrate upregulated nucleotide excision repair and other upregulated resistance mechanisms.

The following references are incorporated by reference in their entireties:

1. Kelland, L., The resurgence of platinum-based cancer chemotherapy. *Nat. Rev. Cancer* 2007, 7, 573-584.
2. Rabik, C. A.; Dolan, M. E., Molecular mechanisms of resistance and toxicity associated with platinating agents. *Cancer Treat. Rev.* 2007, 33, 9-23.
3. Cosaert, J.; Quoix, E., Platinum drugs in the treatment of non-small-cell lung cancer. *Br. J. Cancer* 2002, 87, 825-833.
4. Wakelee, H.; Dubey, S.; Gandara, D., Optimal adjuvant therapy for non-small cell lung cancer—how to handle stage I disease. *Oncologist* 2007, 12, 331-337.
5. Soria, J. C.; Le Chevalier. T., is cisplatin still the best platinum compound in non-small-cell lung cancer? *Ann. Oncol.* 2002, 13, 1515-1517.
6. Momekov, G.; Bakalova, A.; Karaivanova, M., Novel approaches towards development of non-classical platinum-based antineoplastic agents: design of platinum complexes characterized by an alternative DNA-binding pattern and/or tumor-targeted cytotoxicity. *Curr. Med. Chem.* 2005, 12, 2177-2191.
7. Guddneppanavar, R.; Bierbach, U., Adenine-n3 in the DNA minor groove—an emerging target for platinum containing anticancer pharmacophores. *Anticancer Agents Med. Chem.* 2007, 7, 125-138.
8. Martins. E. T.; Baruah, H.; Kramarczyk, J.; Saluta, G.; Day, C. S.; Kucera, G. L.; Bierbach, U., Design, synthesis, and biological activity of a novel non-cisplatin-type platinum-acridine pharmacophore. *J. Med. Chem.* 2001, 44, 4492-4496.
9. Baruah, H.; Rector, C. L.; Monnier, S. M.; Bierbach, U., Mechanism of action of non-cisplatin type DNA-targeted platinum anticancer agents: DNA interactions of novel acridinylthioureas and their platinum conjugates. *Biochem. Pharmacol.* 2002, 64, 191-200.
10. Barry, C. G.; Baruah, H.; Bierbach, U., Unprecedented monofunctional metalation of adenine nucleobase in guanine- and thymine-containing dinucleotide sequences by a cytotoxic platinum-acridine hybrid agent. *J. Am. Chem. Soc.* 2003, 125, 9629-9637.
11. Barry, C. G.; Day, C. S.; Bierbach, U., Duplex-promoted platination of adenine-N3 in the minor groove of DNA: challenging a longstanding bioinorganic paradigm. *J. Am. Chem. Soc.* 2005, 127, 1160-1169.
12. Baruah, H.; Wright, M. W.; Bierbach, U., Solution structural study of a DNA duplex containing the guanine-N7 adduct formed by a cytotoxic platinum-acridine hybrid agent. *Biochemistry* 2005, 44, 6059-6070.
13. Budiman, M. E.; Alexander, R. W.; Bierbach, U., Unique base-step recognition by a platinum-acridinylthiourea conjugate leads to a DNA damage profile complementary to that of the anticancer drug cisplatin. *Biochemistry* 2004, 43, 8560-8567.

14. Connors, T. A.; Cleare, M. J.; Harrap, K. R., Structure-Activity-Relationships of the Anti-Tumor Platinum Coordination-Complexes. *Cancer Treat. Rep.* 1979, 63, 1499-1502.
15. Hess, S. M.; Mounce, A. M.; Sequeira, R. C.; Augustus, T. M.; Ackley, M. C.; Bierbach, U., Platinum-acridinylthiourea conjugates show cell line-specific cytotoxic enhancement in H460 lung carcinoma cells compared to cisplatin. *Cancer Chemother. Pharmacol.* 2005, 56, 337-343.
16. Guddneppanavar, R.; Choudhury, J. R.; Kheradi, A. R.; Steen, B. D.; Saluta, G.; Kucera, G. L.; Day, C. S.; Bierbach, U., Effect of the diamine nonleaving group in platinum-acridinylthiourea conjugates on DNA damage and cytotoxicity. *J. Med. Chem.* 2007, 50, 2259-2263.
17. Guddneppanavar, R.; Saluta, G.; Kucera, G. L.; Bierbach, U., Synthesis, biological activity, and DNA-damage profile of platinum-threading intercalator conjugates designed to target adenine. *J. Med. Chem.* 2006, 49, 3204-3214.
18. Kukushkin, V. Y.; Pombeiro, A. J., Additions to metal-activated organonitriles. *Chem. Rev.* 2002, 102, 1771-1802.
19. Ackley, M. C.; Barry, C. G.; Mounce, A. M.; Farmer, M. C.; Springer, B. E.; Day, C. S.; Wright, M. W.; Berners-Price, S. J.; Hess, S. M.; Bierbach, U., Structure-activity relationships in platinum-acridinylthiourea conjugates: effect of the thiourea nonleaving group on drug stability, nucleobase affinity, and in vitro cytotoxicity. *J. Biol. Inorg. Chem.* 2004, 9, 453-461.
20. Guddneppanavar, R.; Wright, M. W.; Tomsey, A. K.; Bierbach, U., Guanine binding of a cytotoxic platinum-acridin-9-ylthiourea conjugate monitored by I-D $^1$H and 2-D [$^1$H-$^{15}$N] NMR spectroscopy: Hydrolysis is not the rate-determining step. *J. Inorg. Biochem.* 2006, 100, 972-979.
21. Gelasco, A.; Lippard, S. J., Anticancer activity of cisplatin and related complexes. In: *Topics in Biological Inorganic Chemistry*, Vol 1; Clarke, M. J., Sadler, P. J., Eds.; Springer: New York, 1999, pp 1-43.
22. Baruah, H.; Day, C. S.; Wright, M. W.; Bierbach, U., Metal-intercalator-mediated self-association and one-dimensional aggregation in the structure of the excised major DNA adduct of a platinum-acridine agent. *J. Am. Chem. Soc.* 2004, 126, 4492-4493.
23. Margiotta, N.; Habtemariam, A.; Sadler, P. J., Strong, rapid binding of a platinum complex to thymine and uracil under physiological conditions. *Angew Chem Int. Ed. Engl.* 1997, 36, 1185-1187.
24. Manzotti, C.; Pratesi, G.; Menta, E.; Di Domenico, R.; Cavalletti, E.; Fiebig, H. H.; Kelland, L. R.; Farrell. N.; Polizzi, D.; Supino, R.; Pezzoni, G.; Zunino, F., BBR 3464: A novel triplatinum complex, exhibiting a preclinical profile of antitumor efficacy different from cisplatin. *Clin. Cancer Res.* 2000, 6, 2626-2634.
25. Hollis, L. S.; Amundsen, A. R.; Stem, E. W., Chemical and Biological Properties of a New Series of Cis-Diammineplatinum(II) Antitumor Agents Containing 3 Nitrogen Donors—Cis-[Pt(NH$_3$)$_2$(N-Donor)Cl]$^+$. *J. Med. Chem.* 1989, 32, 128-136.
26. Lovejoy, K. S.; Todd, R. C.; Zhang, S.; McCormick, M. S.; D'Aquino, J. A.; Reardon, J. T.; Sancar, A.; Giacomini, K. M.; Lippard, S. J., cis-Diammine(pyridine)chloroplatinum(II), a monofunctional platinum(II) antitumor agent: Uptake, structure, function, and prospects. *Proc. Natl. Acad. Sci. USA* 2008, 105, 8902-8907.
27. Gray, J.; Simon, G.; Bepler, G., Molecular predictors of chemotherapy response in non-small-cell lung cancer. *Expert Rev. Anticancer Ther.* 2007, 7, 545-549.
28. Weaver, D. A.; Crawford, E. L.; Warner, K. A.; Elkhairi, F.; Khuder, S. A.; Willey, J. C., ABCC5, ERCC2, XPA and XRCC1 transcript abundance levels correlate with cisplatin chemoresistance in non-small cell lung cancer cell lines. *Mol. Cancer* 2005, 4, 18.
29. Fujii, T.; Toyooka, S.; Ichimura, K.; Fujiwara, Y.; Hotta, K.; Soh, J.; Suehisa, H.; Kobayashi, N.; Aoe, M.; Yoshino, T.; Kiura, K.; Date, H., ERCC1 protein expression predicts the response of cisplatin-based neoadjuvant chemotherapy in non-small-cell lung cancer. *Lung Cancer* 2008, 59, 377-384.
30. Soria, J. C., ERCC1-tailored chemotherapy in lung cancer: the first prospective randomized trial. *J. Clin. Oncol.* 2007, 25, 2648-2649.
31. Zamble, D. B.; Mu, D.; Reardon, J. T.; Sancar, A.; Lippard, S. J., Repair of cisplatin-DNA adducts by the mammalian excision nuclease. *Biochemistry* 1996, 35, 10004-10013.
32. Dip, R.; Camenisch, U.; Naegeli, H., Mechanisms of DNA damage recognition and strand discrimination in human nucleotide excision repair. *DNA Repair* 2004, 3, 1409-1423.
33. Poklar, N.; Pilch, D. S.; Lippard, S. J.; Redding, E. A.; Dunham, S. U.; Breslauer, K. J., Influence of cisplatin intrastrand crosslinking on the conformation, thermal stability, and energetics of a 20-mer DNA duplex. *Proc. Natl. Acad. Sci. USA* 1996, 93, 7606-7611.
34. S. C. Dhara, *Indian Journal of Chemistry* 1970, 8, 193-194.
35. T. M. Augustus, J. Anderson, S. M. Hess and U. Bierbach, *Bioorganic & Medicinal Chemistry Letters* 2003, 13, 855-858.
36. Z. Ma, J. R. Choudhury. M. W. Wright. C. S. Day, G. Saluta, G. L. Kucera and U. Bierbach, *Journal of Medicinal Chemistry* 2008, 51, 7574-7580.
37. L. A. Graham, G. M. Wilson, T. K. West, C. S. Day, G. L. Kucera and U. Bierbach, *ACS Medicinal Chemistry Letters* 2011, 2, 687-691.

It is contemplated and therefore within the scope of the present invention that any feature that is described above can be combined with any other feature that is described above. Moreover, it should be understood that the present invention contemplates minor modifications that can be made to the compounds, compositions and methods of the present invention. In any event, the present invention is defined by the below claims.

We claim:
1. A compound of Formula I:

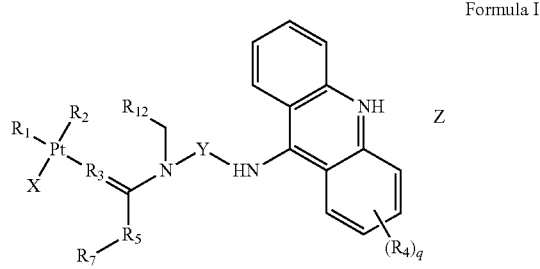

Formula I wherein X is halo, OC(O)R$_9$, nitrate or sulfate;

$R_1$ and $R_2$ are amino groups or together with the platinum atom to which they are attached, $R_1$ and $R_2$ form the ring —$NH_2$—$(CH_2)_v$—$NH_2$— wherein v is 1, 2, 3, or 4 or $R_1$ and $R_2$ together can be any of the following groups a-h;

a
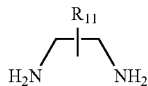

b
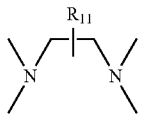

c
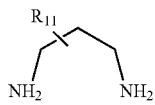

d
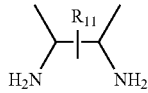

e
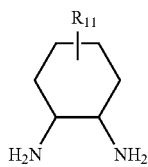

f
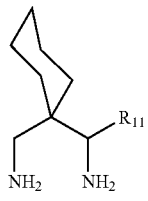

g
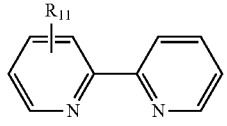

h
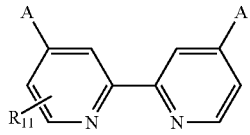

wherein A is H, —$CH_3$, —$OCH_3$, —$CF_3$ or $NO_2$;

$R_3$ is —$N(R_6)$—; wherein $R_6$ is hydrogen or $C_1$-$C_6$alkyl;

$R_4$ is independently an amino, a nitro, —$NHC(O)(R_{10})$, —$NHC(O)O(R_{10})$, —$C(O)NHR_{10}$, —$OC(O)NHR_{10}$, or halo;

$R_{10}$ is hydrogen, $C_{1-6}$ alkyl, phenyl, naphthyl, $C_{3-6}$ cycloalkyl, norbornyl, or adamantyl;

q is 0, 1, or 2;

$R_5$ is a direct bond, —NH— or $C_1$-$C_6$alkylene;

or $R_5$ and X together with the atoms to which they are attached form a 6- or 7-membered ring, wherein said 6- or 7-membered ring contains a linking group —C(O)O— or —OC(O)—;

$R_7$ is hydrogen, methyl, or —C(O)O—$R_8$; wherein $R_8$ is hydrogen, $C_{1-6}$ alkyl, phenyl, naphthyl, $C_{3-6}$ cycloalkyl, norbornyl, adamantyl, a natural or unnatural amino acid or a peptide;

$R_9$ is hydrogen, $C_{1-6}$ alkyl, phenyl, naphthyl, $C_{3-6}$ cycloalkyl, norbornyl, adamantyl, a natural or unnatural amino acid or a peptide;

either or both of $R_{11}$ and $R_{12}$ contain a reactive group on to which a linker and/or one or more of compound W can be added; and if only one of $R_{11}$ and $R_{12}$ contains a reactive group, then the other of $R_{11}$ and $R_{12}$ is hydrogen;

compound W is one or more amino acids, one or more sugars, polymeric ethers, $C_{1-6}$alkylene-phenyl-NH—C(O)—$R_{15}$, folic acid, $\alpha_v\beta_3$ integrin RGD binding peptide, tamoxifen, endoxifen, EGFR (epidermal growth factor receptor) antibody conjugates, kinase inhibitors, diazoles, triazoles, oxazoles, erlotinib, and mixtures thereof;

wherein $R_{15}$ is a peptide;

Y is $C_1$-$C_6$alkyl; and

Z is one or more counterions sufficient to balance the charge of the compound.

2. The compound of claim 1, wherein $R_{11}$ and $R_{12}$ are —OH, —$N_3$, —COOH, —$CONH_2$, —CH=$CH_2$, —C≡CH, —$(CH_2)_{1-6}$—OH, —$(CH_2)_{1-6}$—$N_3$, —$(CH_2)_{1-6}$—COOH, or —$(CH_2)_{1-6}$—CH=$CH_2$, or —$(CH_2)_{1-6}$—C≡CH.

3. The compound of claim 1, wherein $R_{11}$ and $R_{12}$ combined with the linker and compound W are —NH—$R_{13}$,

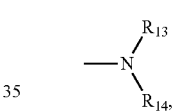

—O—$R_{13}$, —CH=CH—$R_{13}$, —C≡C—$R_{13}$, —$N_3$, —COOH, —$COOR_{14}$, —C(O)NH—$R_{13}$, —NHC(O)—$R_{13}$, —OC(O)NH—$R_{13}$, —OC(O)O—$R_{13}$, —$(CH_2)_{1-6}$—NH—$R_{13}$,

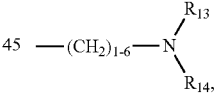

—$(CH_2)_{1-6}$—O—$R_{13}$, —$(CH_2)_{1-6}$—$N_3$, —$(CH_2)_{1-6}$—COOH, —$(CH_2)_{1-6}$—$COOR_{14}$ or —$(CH_2)_{1-6}$—CH=CH—$R_{13}$;

wherein $R_{13}$ and $R_{14}$ are independently selected from the group consisting of one or more amino acids, one or more sugars, polymeric ethers, $C_{1-6}$alkylene-phenyl-NH—C(O)—$R_{15}$, folic acid, $\alpha_v\beta_3$ integrin RGD binding peptide, tamoxifen, endoxifen, EGFR (epidermal growth factor receptor) antibody conjugates, kinase inhibitors, diazoles, triazoles, oxazoles, erlotinib, and mixtures thereof; wherein $R_{15}$ is a peptide.

4. The compound of claim 1, wherein $R_6$ is hydrogen or methyl and $R_1$ and $R_2$ are amino groups or together with the platinum atom to which they are attached, $R_1$ and $R_2$ form the ring —$NH_2$—$(CH_2)_v$—$NH_2$—wherein v is 2 or 3.

5. The compound of claim 4, wherein Y is —$CH_2$—.

6. The compound of claim 5, wherein $R_1$ and $R_2$ are amino groups or together with the platinum atom to which $R_1$ and $R_2$ are attached are —$NH_2$—$CH_2$—$NH_2$—.

7. The compound of claim 6, wherein the one or more counter ions of Z comprise $NO_3$.

8. The compound of claim 7, wherein $R_5$ is —NH— or —$CH_2$—.

9. The compound of claim 8, wherein $R_6$ is hydrogen.

10. The compound of claim 9, wherein the compound is Example 1

Example 1

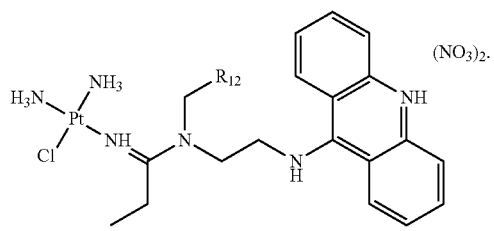

(NO$_3$)$_2$.

11. The compound of claim 7, wherein the compound is Example 2:

Example 2

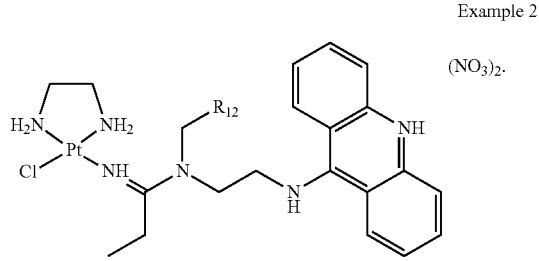

(NO$_3$)$_2$.

12. A method of treating cancer comprising administering to a subject in need thereof an effective amount of the compound of Formula I:

Formula I

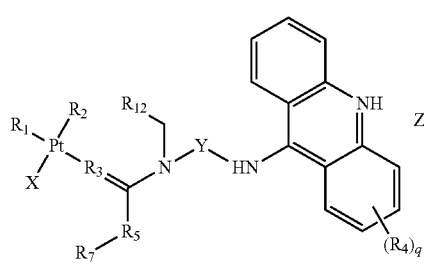

wherein X is halo, OC(O)$R_9$, nitrate or sulfate;

$R_1$ and $R_2$ are amino groups or together with the platinum atom to which they are attached, $R_1$ and $R_2$ form the ring —$NH_2$—$(CH_2)_v$—$NH_2$— wherein v is 1, 2, 3, or 4 or $R_1$ and $R_2$ together can be any of the following groups a-h;

a

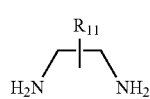

-continued b

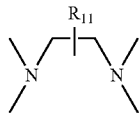

c

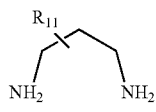

d

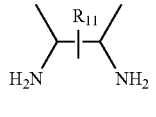

e

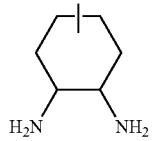

f

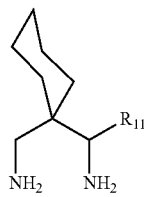

g

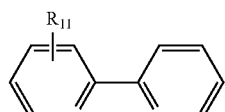

h

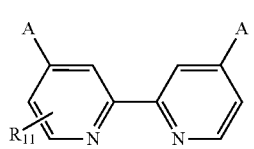

wherein A is H, —$CH_3$, —$OCH_3$, $CF_3$ or $NO_2$;
$R_3$ is —N($R_6$)—; wherein $R_6$ is hydrogen or $C_1$-$C_6$alkyl;
$R_4$ is independently an amino, a nitro, —NHC(O)($R_{10}$), —NHC(O)O($R_{10}$), —C(O)NH$R_{10}$, —OC(O)NH$R_{10}$, or halo;
$R_{10}$ is hydrogen, $C_{1-6}$ alkyl, phenyl, naphthyl, $C_{3-6}$ cycloalkyl, norbornyl, or adamantyl;
q is 0, 1, or 2;
$R_5$ is a direct bond, —NH— or $C_1$-$C_6$alkylene;
or $R_5$ and X together with the atoms to which they are attached form a 6- or 7-membered ring, wherein said 6- or 7-membered ring contains a linking group —C(O)O— or —OC(O)—;
$R_7$ is hydrogen, methyl, or —C(O)O—$R_8$; wherein
$R_8$ is hydrogen, $C_{1-6}$ alkyl, phenyl, naphthyl, $C_{3-6}$ cycloalkyl, norbornyl, adamantyl, a natural or unnatural amino acid or a peptide;
$R_9$ is hydrogen, $C_{1-6}$ alkyl, phenyl, naphthyl, $C_{3-6}$ cycloalkyl, norbornyl, adamantyl, a natural or unnatural amino acid or a peptide;
either or both of $R_{11}$ and $R_{12}$ contain a reactive group on to which a linker and/or one or more of compound W can be added; and if only one of $R_{11}$ and $R_{12}$ contains a reactive group, then the other of $R_{11}$ and $R_{12}$ is hydrogen;

compound W is one or more amino acids, one or more sugars, polymeric ethers, $C_{1-6}$alkylene-phenyl-NH—C(O)—$R_{15}$, folic acid, $\alpha_v\beta_3$ integrin RGD binding peptide, tamoxifen, endoxifen, EGFR (epidermal growth factor receptor) antibody conjugates, kinase inhibitors, diazoles, triazoles, oxazoles, erlotinib, and mixtures thereof;

wherein $R_{15}$ is a peptide;

Y is $C_1$-$C_6$alkyl; and

Z is one or more counterions sufficient to balance the charge of the compound.

13. The method of claim 12, wherein the cancer is selected from the group consisting of lung cancer, testicular cancers, ovarian carcinomas, head and neck cancers, leukemias and lymphomas.

14. The method of claim 13, wherein $R_6$ is hydrogen or methyl and $R_1$ and $R_2$ are amino groups or together with the platinum atom to which they are attached, $R_1$ and $R_2$ form the ring —NH$_2$—(CH$_2$)$_v$—NH$_2$—wherein v is 2 or 3.

15. The method of claim 14, wherein Y is —CH$_2$—.

16. The method of claim 15, wherein $R_1$ and $R_2$ are amino groups or together with the platinum atom to which $R_1$ and $R_2$ are attached are —NH$_2$—CH$_2$—CH$_2$—NH$_2$—.

17. The method of claim 16, wherein the one or more counter ions of Z comprise NO$_3$.

18. The method of claim 17, wherein $R_5$ is —NH— or —CH$_2$—.

19. The method of claim 18, wherein $R_6$ is hydrogen.

20. A pharmaceutical composition comprising the compound of Formula 1:

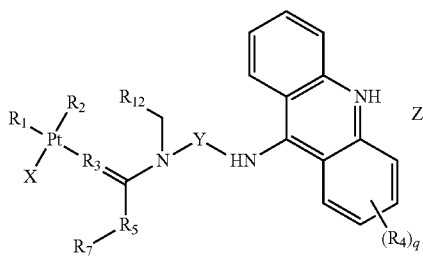

Formula I wherein X is halo, OC(O)$R_9$, nitrate or sulfate;

$R_1$ and $R_2$ are amino groups or together with the platinum atom to which they are attached, $R_1$ and $R_2$ form the ring —NH$_2$—(CH$_2$)$_v$—NH$_2$—wherein v is 1, 2, 3, or 4 or $R_1$ and $R_2$ together can be any of the following groups a-h;

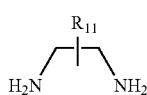
a

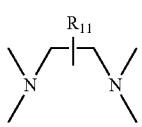
b

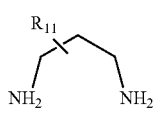
c

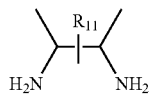
d

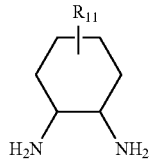
e

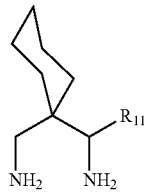
f

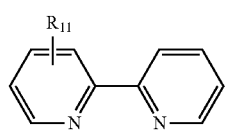
g

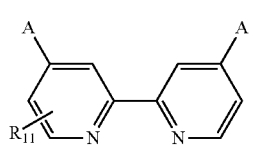
h wherein A is H, —CH$_3$, —OCH$_3$, CF$_3$ or NO$_2$;

$R_3$ is —N($R_6$)—; wherein $R_6$ is hydrogen or $C_1$-$C_6$alkyl;

$R_4$ is independently an amino, a nitro, —NHC(O)($R_{10}$), —NHC(O)O($R_{10}$), —C(O)NHR$_{10}$, —OC(O)NHR$_{10}$, or halo;

$R_{10}$ is hydrogen, $C_{1-6}$ alkyl, phenyl, naphthyl, $C_{3-6}$ cycloalkyl, norbornyl, or adamantyl;

q is 0, 1, or 2;

$R_5$ is a direct bond, —NH— or $C_1$-$C_6$alkylene;

or $R_5$ and X together with the atoms to which they are attached form a 6- or 7-membered ring, wherein said 6- or 7-membered ring contains a linking group —C(O)O— or —OC(O)—;

$R_7$ is hydrogen, methyl, or —C(O)O—$R_8$; wherein $R_8$ is hydrogen, $C_{1-6}$ alkyl, phenyl, naphthyl, $C_{3-6}$ cycloalkyl, norbornyl, adamantyl, a natural or unnatural amino acid or a peptide;

$R_9$ is hydrogen, $C_{1-6}$ alkyl, phenyl, naphthyl, $C_{3-6}$ cycloalkyl, norbornyl, adamantyl, a natural or unnatural amino acid or a peptide;

either or both of $R_{11}$ and $R_{12}$ contain a reactive group on to which a linker and/or one or more of compound W can be added; and if only one of $R_{11}$ and $R_{12}$ contains a reactive group, then the other of $R_{11}$ and $R_{12}$ is hydrogen;

compound W is one or more amino acids, one or more sugars, polymeric ethers, $C_{1-6}$alkylene-phenyl-NH—C(O)—$R_{15}$, folic acid, $\alpha_v\beta_3$ integrin RGD binding peptide, tamoxifen, endoxifen, EGFR (epidermal growth factor receptor) antibody conjugates, kinase inhibitors, diazoles, triazoles, oxazoles, erlotinib, and mixtures thereof;

wherein $R_{15}$ is a peptide;

Y is $C_1$-$C_6$alkyl; and

Z is one or more counterions sufficient to balance the charge of the compound;

and a pharmaceutically acceptable diluent, carrier, or excipient.

21. The pharmaceutical composition of claim 20, wherein Y is —$CH_2$—, wherein $R_1$ and $R_2$ are amino groups or together with the platinum atom to which $R_1$ and $R_2$ are attached are —$NH_2$—$CH_2$—$CH_2$—$NH_2$—, and wherein the one or more counter ions of Z comprise $NO_3$.

22. The pharmaceutical composition of claim 21, wherein $R_5$ is —NH— or —$CH_2$—, wherein $R_6$ is hydrogen or methyl and $R_1$ and $R_2$ are amino groups or together with the platinum atom to which they are attached, $R_1$ and $R_2$ form the ring —$NH_2$—$(CH_2)_v$—$NH_2$— wherein v is 2 or 3.

23. The pharmaceutical composition of claim 20, further comprising one or more compounds selected from the group consisting of HERCEPTIN™ (trastuzumab), RITUXAN™ (rituximab), ZEVALIN™ (ibritumomab tiuxetan), LYMPHOCIDE™ (epratuzumab), GLEEVAC™, BEXXAR™ (iodine 131 tositumomab), ERBITUX™ (IMC-C225), KDR inhibitory agents, AVASTIN™, VEGF-TRAP™, ABX-EGF (panitumumab), IRESSA™ (gefitinib), TARCEVA™ (erlotinib), Campath, IL-8, B-FGF, Tek antagonists, anti-TWEAK agents, anti-PDGF-BB antagonists, SD-7784, cilengitide; pegaptanib octasodium; Alphastatin, M-PGA; ilomastat, emaxanib, vatalanib, 2-methoxyestradiol, TLC ELL-12, anecortave acetate, alpha-D148 Mab, CEP-7055, anti-Vn Mab, DAC:antiangiogenic, Angiocidin, KM-2550, SU-0879, CGP-79787, YIGSR-Stealth, fibrinogen-E fragment, TBC-1635; SC-236, ABT-567, Metastatin, maspin, ER-68203-00, Benefin, Tz-93, TAN-1120, FR-111142, platelet factor 4, vascular endothelial growth factor antagonist, bevacizumab (pINN), XL 784, XL 647, MAb, alpha5beta3 integrin, enzastaurin hydrochloride (USAN), CEP 7055, BC 1, VEGF antagonist, rBPI 21 and BPI-derived antiangiogenic, PI 88, cilengitide (pINN), cetuximab (INN), AVE 8062, AS 1404, SG 292, Endostatin, ATN 161, ANGIOSTATIN, ZD 6474, ZD 6126, PPI 2458, AZD 9935, AZD 2171, vatalanib (pINN), pegaptanib (Pinn), xanthorrhizol, SPV5.2, SDX 103, PX 478, METASTATIN, troponin I, SU 6668, OXI 4503, o-guanidines, motuporamine C, CDP 791, atiprimod (pINN), E 7820, CYC 381, AE 941, urokinase plasminogen activator inhibitor, oglufanide (pINN), HIF-1alfa inhibitors, CEP 5214, BAY RES 2622; Angiocidin, A6, KR 31372, GW 2286, EHT 0101, CP 868596, CP 564959, CP 547632, compound 786034 from GlaxoSmithKline, KRN 633, anginex, ABT 510, AAL 993, VEGI, tumor necrosis factor-alpha inhibitors, SU 11248, ABT 518, YH16, S-3APG, KDR, GEB 116, CS 706, combretastatin A4 prodrugs, chondroitinase AC, BAY RES 2690, AGM 1470, AG 13925, Tetrathiomolybdate, GCS 100, CV 247, CKD 732, irsogladine (INN), RG 13577, WX 360, squalamine (pIN), RPI 4610, heparanase inhibitors, KL 3106, Honokiol, ZK CDK, ZK Angio, ZK 229561, XMP 300, VGA 1102, Vasostatin, Flk-1, TZ 93, TumStatin, truncated soluble FLT 1 Tie-2 ligands and thrombospondin 1 inhibitor.

24. A system of delivering a compound of formula I as claimed in claim 1 to a patient in need thereof, wherein said system employs directly or indirectly binding said compound of formula I to one or more members selected from the group consisting of one or more amino acids, one or more sugars, one or more polymeric ethers, $C_{1-6}$alkylene-phenyl-NH—C(O)—$R_{15}$, folic acid, $\alpha_v\beta_3$ integrin RGD binding peptide, tamoxifen, endoxifen, EGFR (epidermal growth factor receptor) antibody conjugates, kinase inhibitors, diazoles, triazoles, oxazoles, erlotinib, and mixtures thereof; wherein $R_{15}$ is a peptide.

* * * * *